US008822464B2

(12) United States Patent
Grauert et al.

(10) Patent No.: US 8,822,464 B2
(45) Date of Patent: Sep. 2, 2014

(54) N-ARYL-PIPERAZINE DERIVATIVES AND THEIR USE AS POSITIVE ALLOSTERIC MODULATORS OF MGLUR5 RECEPTORS

(71) Applicants: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE)

(72) Inventors: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 24 days.

(21) Appl. No.: 13/684,606

(22) Filed: Nov. 26, 2012

(65) Prior Publication Data
US 2013/0137688 A1 May 30, 2013

(30) Foreign Application Priority Data
Nov. 28, 2011 (EP) ..................................... 11190971

(51) Int. Cl.
| *A61K 31/5377* | (2006.01) |
| *A61K 31/496* | (2006.01) |
| *A61K 31/497* | (2006.01) |
| *A61K 31/501* | (2006.01) |
| *A61K 31/506* | (2006.01) |
| *A61K 31/52* | (2006.01) |
| *C07D 231/12* | (2006.01) |
| *C07D 473/34* | (2006.01) |
| *C07D 401/12* | (2006.01) |
| *C07D 403/12* | (2006.01) |
| *C07D 401/14* | (2006.01) |
| *C07D 403/14* | (2006.01) |
| *A61K 31/53* | (2006.01) |
| *C07D 409/14* | (2006.01) |
| *C07D 401/06* | (2006.01) |
| *C07D 413/14* | (2006.01) |

(52) U.S. Cl.
CPC ............ *C07D 403/14* (2013.01); *C07D 231/12* (2013.01); *C07D 473/34* (2013.01); *C07D 401/14* (2013.01); *C07D 403/12* (2013.01); *C07D 409/14* (2013.01); *C07D 401/06* (2013.01); *C07D 401/12* (2013.01); *C07D 413/14* (2013.01)
USPC .................. 514/235.8; 514/245; 514/252.02; 514/252.11; 514/252.19; 514/253.06; 514/254.05; 514/253.09; 544/121; 544/194; 544/238; 544/277; 544/295; 544/357; 544/363; 544/364; 544/371

(58) Field of Classification Search
None
See application file for complete search history.

(56) References Cited

U.S. PATENT DOCUMENTS

| 6,166,008 | A | 12/2000 | Johnson et al. |
| 7,157,464 | B2 * | 1/2007 | Pennell et al. ........... 514/254.05 |
| 7,582,635 | B2 | 9/2009 | Sun et al. |
| 8,008,300 | B2 | 8/2011 | Sun et al. |
| 8,048,890 | B2 | 11/2011 | Buschmann et al. |
| 2003/0055085 | A1 | 3/2003 | Wagenen et al. |
| 2004/0186111 | A1 | 9/2004 | Sun et al. |
| 2005/0256130 | A1 | 11/2005 | Pennell et al. |
| 2007/0154428 | A1 | 7/2007 | Sato et al. |
| 2010/0004254 | A1 | 1/2010 | Sun et al. |
| 2010/0216787 | A1 | 8/2010 | Sato et al. |
| 2010/0240618 | A1 * | 9/2010 | Pennell et al. ................. 514/150 |
| 2012/0004217 | A1 | 1/2012 | Sun et al. |
| 2012/0015954 | A1 | 1/2012 | Sun et al. |
| 2013/0137688 | A1 | 5/2013 | Grauert et al. |
| 2013/0143870 | A1 | 6/2013 | Grauert et al. |
| 2013/0150341 | A1 | 6/2013 | Grauert et al. |
| 2013/0150347 | A1 | 6/2013 | Rudolf et al. |
| 2013/0150355 | A1 | 6/2013 | Rudolf et al. |
| 2013/0158011 | A1 | 6/2013 | Rudolf et al. |
| 2013/0158038 | A1 | 6/2013 | Rudolf et al. |
| 2013/0184248 | A1 | 7/2013 | Grauert et al. |

FOREIGN PATENT DOCUMENTS

CA      2476031 A1    9/2003
(Continued)

OTHER PUBLICATIONS

Abstract in English for WO2011002067, Publication Date: Jan. 1, 2011.
(Continued)

*Primary Examiner* — Emily Bernhardt
(74) *Attorney, Agent, or Firm* — Michael P. Morris; Anthony P. Bottino

(57) ABSTRACT

This invention relates to compounds of formula I

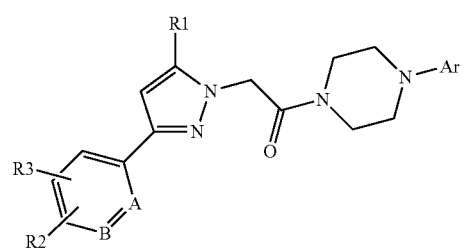

their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment. A, B, Ar, $R^1$, $R^2$, $R^3$ have meanings given in the description.

2 Claims, No Drawings

(56) References Cited

FOREIGN PATENT DOCUMENTS

| | | | |
|---|---|---|---|
| EP | 0307145 | A1 | 3/1989 |
| EP | 0919232 | A1 | 6/1999 |
| WO | 9749395 | | 12/1997 |
| WO | 0206288 | A1 | 1/2002 |
| WO | 03051833 | A2 | 6/2003 |
| WO | 03053922 | A2 | 7/2003 |
| WO | 03076432 | A1 | 9/2003 |
| WO | 03105853 | A1 | 12/2003 |
| WO | 2004058754 | A1 | 7/2004 |
| WO | 2005030128 | A2 | 4/2005 |
| WO | 2005056015 | A1 | 6/2005 |
| WO | 2005085241 | A1 | 9/2005 |
| WO | 2007021573 | A1 | 2/2007 |
| WO | 2007087135 | A2 | 8/2007 |
| WO | 2008112440 | A1 | 9/2008 |
| WO | 2008145616 | A1 | 12/2008 |
| WO | 2008148840 | A1 | 12/2008 |
| WO | 2008156580 | A1 | 12/2008 |
| WO | 2009143404 | A1 | 11/2009 |
| WO | 2010124055 | A1 | 10/2010 |
| WO | 2010126811 | A1 | 11/2010 |
| WO | 2011002067 | A1 | 1/2011 |
| WO | 2011082010 | A1 | 7/2011 |

OTHER PUBLICATIONS

Adams, C.E. et al., "Chlorpromazine Versus Placebo for Schizophrenia (Review)." The Cochrane Library, 2009, pp. 1-3.

CHEMCATS: Accession No. 0046382561, Oct. 14, 2011.

Dorwald, F. Z. "Side Reactions in Organic Synthesis: A Guide to Successful Synthesis Design." Wiley-VCH Verlag GmbH & Co. KGaA, 2005, pp. 1-390.

Lindsley, C.W., et al., "Discovery of Positive Allosteric Modulators for the Metabotropic Glutamate Receptor Subtype-5 from a Series of N-(1,3-Diphenyl-1H-pyrazol-5-yl) benzamides that Potentiate Receptor Function in Vivo", J. Med. Chem, 2004, 47, pp. 5825-5828.

Shasheva. E. Y. et al., "Reactions of Hydroxyphenyl-substituted 1,2,4-Triazoles with Electrophylic Reagents", Russian Journal of General Chemistry, 2009, vol. 79, No. 10, pp. 2234-2243.

Wermuth, Camille G. "Practice of Medicinal Chemistry, Third Edition." Elsevier Ltd., 2008, Ch. 6, 15, 18, and 20. (74 pages).

International Search Report and Written Opinion for PCT/EP2012/075312 mailed Feb. 7, 2013.

International Search Report and Written Opinion for PCT/EP2012/075313 mailed Feb. 7, 2013.

European Search Report for EP 11193380.0 mailed Mar. 14, 2012.

\* cited by examiner

N-ARYL-PIPERAZINE DERIVATIVES AND THEIR USE AS POSITIVE ALLOSTERIC MODULATORS OF MGLUR5 RECEPTORS

FIELD OF THE INVENTION

This invention relates to substituted pyrazoles and their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment.

BACKGROUND OF THE INVENTION

Glutamate is the primary excitatory amino acid in the mammalian central nervous system. Neurotransmisstion mediated by glutamate has been demonstrated to be critical in many physiological processes, such as synaptic plasticity, long term potentiation involved in both learning and memory as well as sensory perception (Riedel et al., Behav. Brain Res. 2003, 140:1-47). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors, the ionotropic glutamate receptors (NMDA, AMPA and kainate) and the metabotropic glutamate receptors (mGluR). The ionotropic receptors are ligand gated ion channels and are thought to be responsible for the regulating rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Disregulation in glutamatergic neurotransmission, for example through altered glutamate release or post-synaptic receptor activation, has been demonstrated in a variety of neurological as well as psychiatric disorders. Hypofunction of the NMDA receptor has not only been demonstrated in Alzheimer's patients, but is increasingly accepted as the putative cause of schizophrenia (Farber et al., Prog. Brain Res., 1998, 116: 421-437, Coyle et al., Cell. and Mol Neurobiol. 2006, 26: 365-384). This is supported by clinical studies showing that antagonists of the NMDA receptor induce symptoms indistinguishable to those suffered by schizophrenia patients (Javitt et al., Am J. Psychiatry, 1991, 148: 1301-1308). Therefore, approaches that could potentiate or normalize NMDA receptor signaling have the potential to treat neurological and psychiatric disorders.

mGluR5 belongs to a superfamily of currently eight identified Type III GPCRs, which are unique in that the glutamate ligand binds to a large extracelullar amino-terminal protein domain. This superfamily is further divided into three groups (Group I, II and III) based on amino acid homology as well as the intracellular signalling cascades they regulate (Schoepp et al., Neuropharma, 1999, 38:1431-1476). mGluR5 belongs to group I and is coupled to the phospholipase C signalling cascade which regulates intracellular calcium mobilization.

In the CNS, mGluR5 has been demonstrated to be expressed mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Luj an et al., Eur. J. Neurosci. 1996, 8: 1488-1500). A functional interaction between mGluR5 and the NMDA receptor has also been demonstrated, where activation of mGluR5 potentiates the activation state of the NMDA receptor (Mannaioni et al, NeuroSci., 2001, 21:5925-5924, Rosenbrock et al., Eur. J. Pharma., 2010, 639:40-46). Furthermore, activation of mGluR5 has been demonstrated in pre-clinical in vivo models to rescue cognitive impairment as well as psychotic disturbance induced by NMDA receptor antagonists (Chan et al., Psychopharma. 2008, 198:141-148). Therefore, activation of mGluR5, and thereby potentiation or normalization of the NMDA receptor signaling, is a potential mechanism for the treatment of psychiatric and neurological disorders.

Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity. An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state.

Positive allosteric modulators of mGluR5 have recently been identified (O'Brien et al., Mol. Pharma. 2003, 64: 731-740, Lindsley et al., J. Med. Chem 2004, 47: 5825-5828). These compounds potentiate mGluR5 activity in the presence of bound glutamate. In the absence of bound glutamate, the mGluR5 positive modulators do not demonstrate intrinsic activity. Therefore, these compounds potentiate the natural signaling of mGluR5 as opposed to agonists which activate the receptor in a permanent, unnatural manor. mGluR5 positive allosteric modulators therefore represent an approach to potentiate mGluR5 signaling which in turn potentiates and normalizes the NMDA receptor hypofunction detected in neurological and psychiatric disorders.

WO 2003/105853 and WO 2005/056015 disclose substituted pyrazoles that are said to be CCR1 receptor antagonists and to be useful for the treatment of inflammation and immune disorders. Quite surprisingly, according to the present invention, some selected pyrazole derivatives show positive modulatory activity on the mGluR5 receptor without having an inhibitory effect on the CCR1 receptor. Such compounds are useful for the treatment of psychotic disorders, cognitive disorders and dementias.

DETAILED DESCRIPTION OF THE INVENTION

The present invention is directed to compounds of formula I:

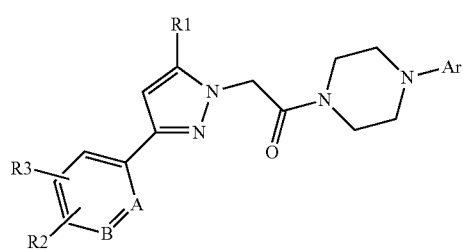

in which

A and B independently represent CH or N;

$R^1$ represents aryl, heteroaryl, $C_{1-8}$alkyl, $C_{3-7}$cycloalkyl, —O—$C_{1-8}$alkyl which latter five groups are optionally substituted with one or more substituents selected from halogen, —CN, $C_{1-3}$alkyl, —O—$C_{1-3}$alkyl;

$R^2$ and $R^3$ independently represent —H, halogen, —CN, —COO—$C_{1-4}$alkyl, $C_{1-5}$alkyl, $C_{3-5}$cycloalkyl, —O—$C_{1-5}$alkyl which latter four groups are optionally substituted with one or more fluorine atoms;

Ar represents

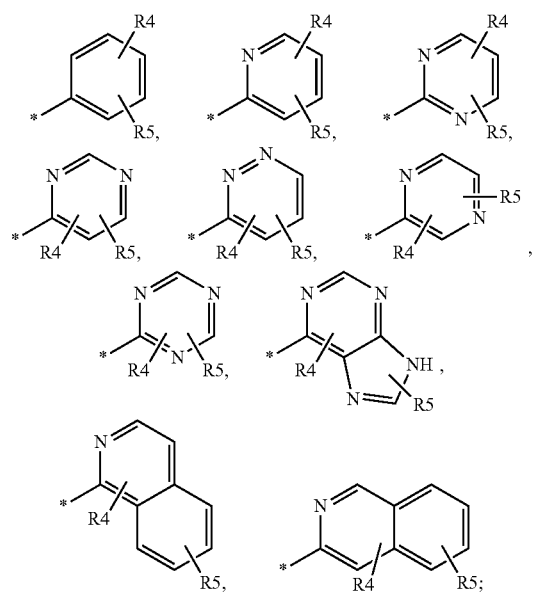

$R^4$ and $R^5$ independently represent —H, halogen, —OH, —CN, —$NH_2$, $C_{1-5}$alkyl, phenyl, —NH—$C_{1-5}$alkyl, —N($C_{1-5}$alkyl)$_2$, —O—$C_{1-5}$alkyl, —COO—$C_{1-5}$alkyl, —CONH($C_{1-5}$alkyl), —CON($C_{1-5}$alkyl)$_2$, —NH—CONH—$C_{1-5}$alkyl, —NHCON($C_{1-5}$alkyl)$_2$, —NHCO—$C_{1-5}$alkyl which latter eleven groups are optionally substituted with one or more substituents selected from halogen, —OH, morpholinyl-;

or a salt thereof, particularly a physiologically acceptable salt thereof.

In second embodiment, in the general formula I, A, B, Ar, $R^2$, $R^3$ have the same meaning as defined in any of the preceding embodiments, and $R^1$ represents phenyl, thienyl-, pyridinyl, $C_{1-4}$alkyl, $C_{3-6}$cycloalkyl, —O—$C_{1-3}$alkyl which latter six groups are optionally substituted with one or more substituents selected from chloro, bromo, fluoro, $C_{1-3}$alkyl, —O—$C_{1-3}$alkyl.

In another embodiment, in the general formula I, A, B, $R^1$, $R^2$, $R^3$ have the same meaning as defined in any of the preceding embodiments, and Ar represents phenyl, pyridinyl, pyridazinyl, pyrazinyl, pyrimidinyl, triazinyl, isochinolinyl, purinyl which latter eight groups are optionally substituted with one or more substituents selected from chloro, bromo, fluoro, —CN, $C_{1-3}$alkyl, O—$C_{1-3}$alkyl [which latter two groups are optionally substituted with one or more substituents selected from fluoro, —OH, morpholinyl-].

In another embodiment, in the general formula I, Ar, $R^1$ have the same meaning as defined in any of the preceding embodiments, and the group

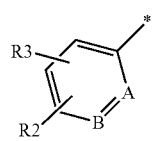

represents phenyl, 2-pyridyl which latter two groups are optionally substituted with one or more substituents selected from chloro, bromo, fluoro, —CN, $C_{1-3}$alkyl, $C_{3-5}$cycloalkyl, —O—$C_{1-3}$ alkyl, —COO—$C_{1-4}$alkyl which latter four groups are optionally substituted with one or more fluorine atoms.

In another embodiment, in the general formula I, A, B, Ar, $R^2$, $R^3$ have the same meaning as defined in any of the preceding embodiments, and $R^1$ represents phenyl, 2-pyridinyl, 2-thienyl-, $C_{1-4}$alkyl, $C_{3-6}$cycloalkyl, O—$C_{1-3}$alkyl which latter six groups are optionally substituted with one or more substituents selected from chloro, fluoro, methyl, methoxy.

In another embodiment, in the general formula I, A, B, $R^1$, $R^2$, $R^3$ have the same meaning as defined in any of the preceding embodiments, and Ar represents phenyl,

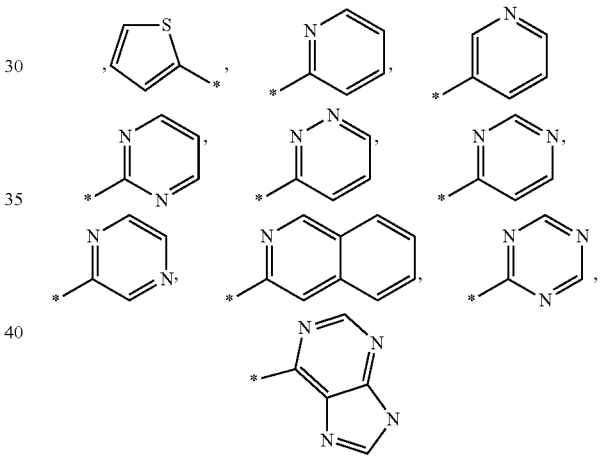

which latter eleven groups are optionally substituted with one or more substituents selected from chloro, bromo, fluoro, —CN, $C_{1-3}$alkyl, O—$C_{1-3}$alkyl [which latter two groups are optionally substituted with one or more substituents selected from fluoro, —OH, 4-morpholinyl-].

In another embodiment, in the general formula I, Ar, $R^1$ have the same meaning as defined in any of the preceding embodiments, and A represents N or CH;

B represents CH.

In another embodiment, in the general formula I, A, B, Ar, $R^2$, $R^3$ have the same meaning as defined in any of the preceding embodiments, and $R^1$ represents phenyl, methyl, ethyl, propyl, iso-propyl, cyclopropyl, cyclohexyl, methoxy,

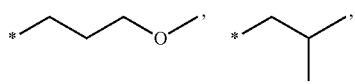

-continued
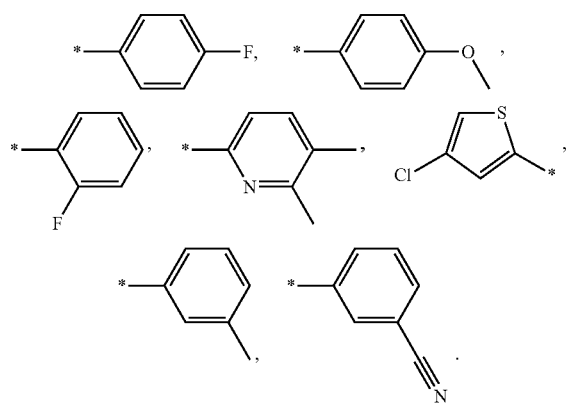
In another embodiment, in the general formula I, A, B, $R^1$, $R^2$, $R^3$ have the same meaning as defined in any of the preceding embodiments, and
Ar represents
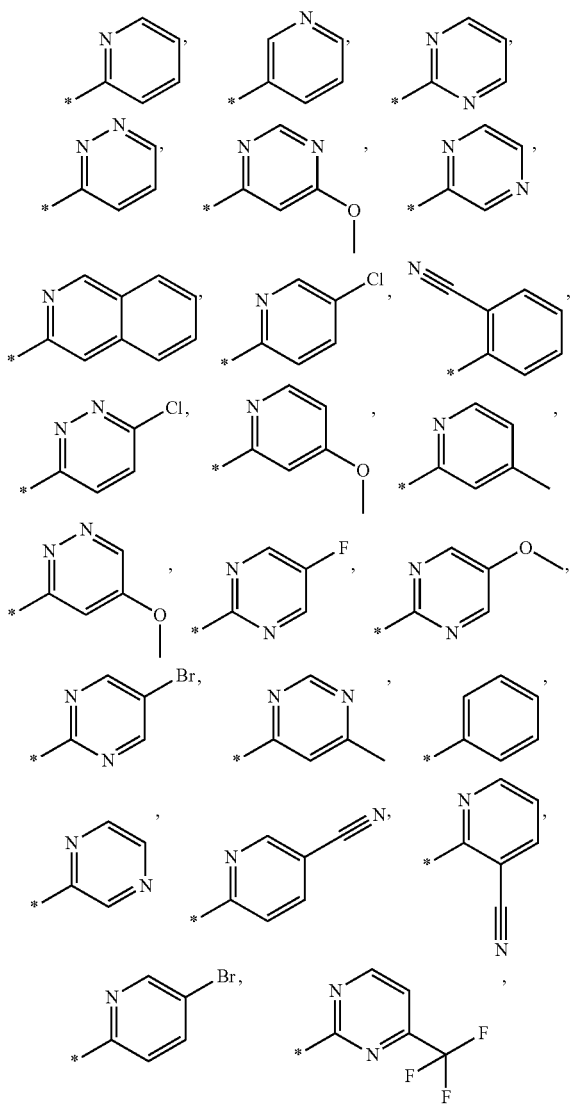
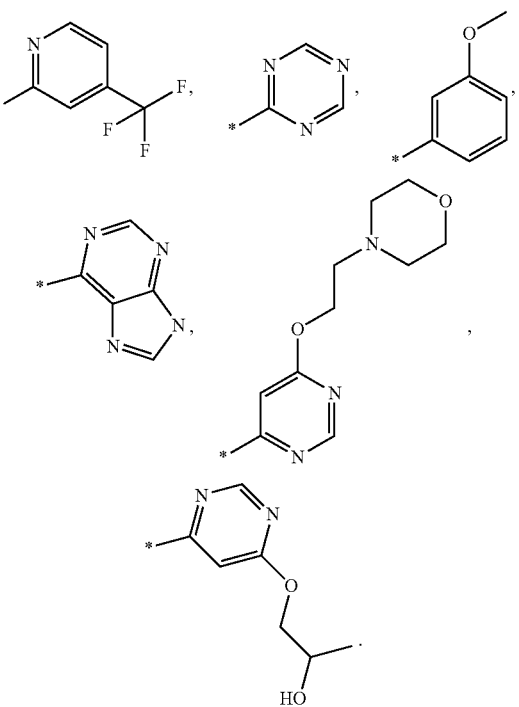
In another embodiment, in the general formula I, Ar, $R^1$ have the same meaning as defined in any of the preceding embodiments, and the group
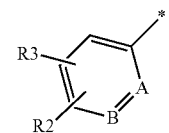
represents
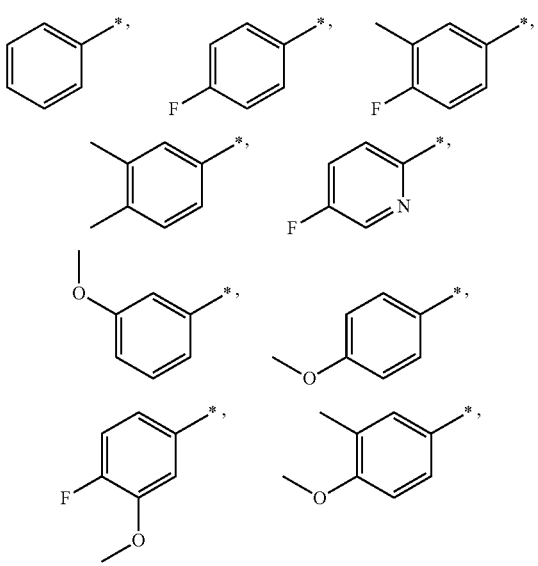

-continued
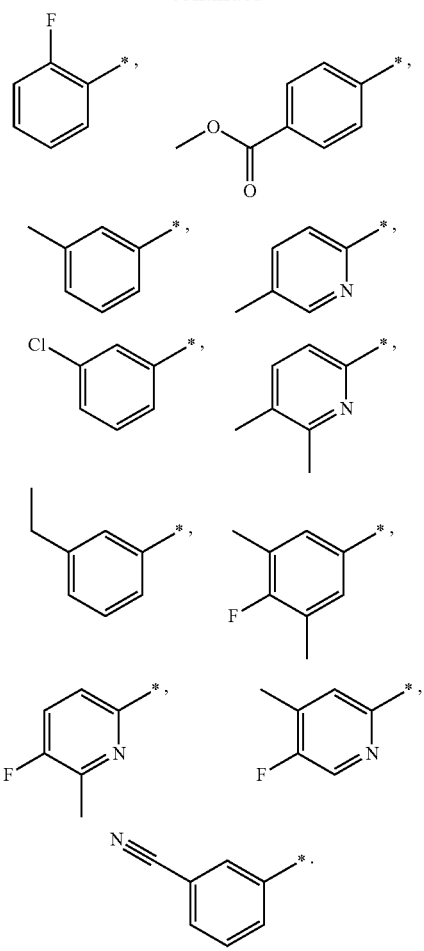
A further embodiment of the present invention comprises compounds of formula I in which
A represents N or CH;
B represents CH;
$R^1$ represents phenyl, methyl, ethyl, propyl, iso-propyl, cyclopropyl, cyclohexyl, methoxy,
Ar represents
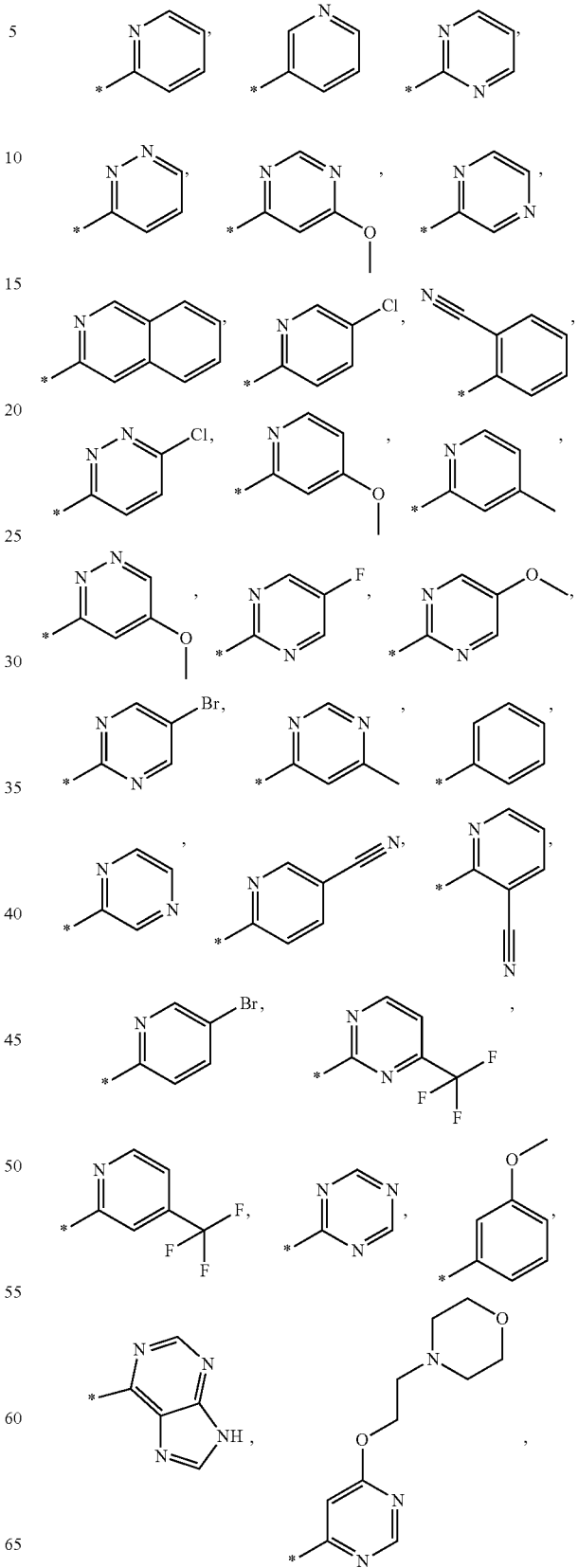

-continued

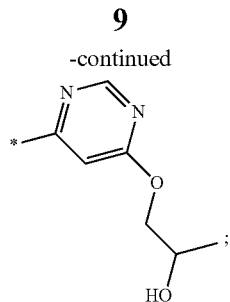

the group

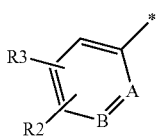

represents

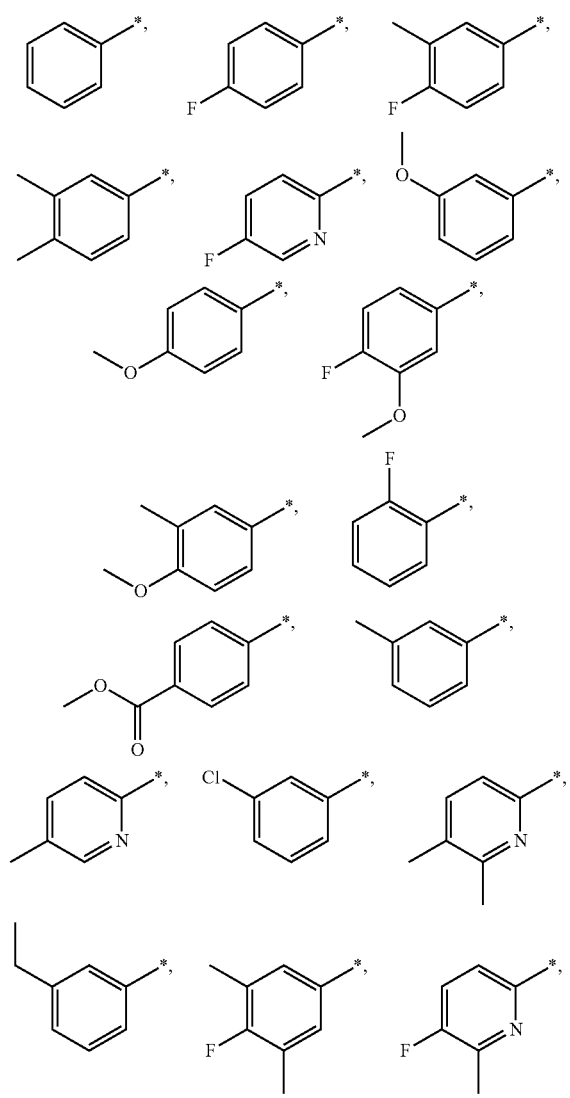

-continued

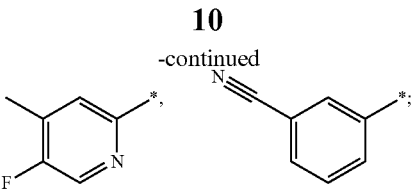

or a salt thereof, particularly a physiologically acceptable salt thereof.

TERMS AND DEFINITIONS USED

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

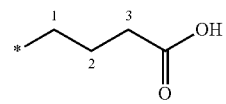

wherein the carboxy group is attached to the third carbon atom of the propyl group. The terms "1-methylpropyl-", "2,2-dimethylpropyl-" or "cyclopropylmethyl-" group represent the following groups:

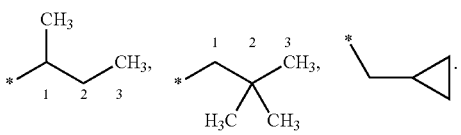

The asterisk may be used in sub-formulas to indicate the bond which is connected to the core molecule as defined.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxy-ethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzene-sulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methane-sulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Alkylene:

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

Alkenyl:

The term "$C_{2-n}$-alkenyl", is used for a group as defined in the definition for "$C_{1-n}$-alkyl" with at least two carbon atoms, if at least two of those carbon atoms of said group are bonded to each other by a double bond.

Alkenylene:

The term "$C_{2-n}$-alkenylene" is used for a group as defined in the definition for "$C_{1-n}$-alkylene" with at least two carbon atoms, if at least two of those carbon atoms of said group are bonded to each other by a double bond.

Alkynyl:

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

Alkynylene:

The term "$C_{2-n}$-alkynylene" is used for a group as defined in the definition for "$C_{1-n}$-alkylene" with at least two carbon atoms, if at least two of those carbon atoms of said group are bonded to each other by a triple bond.

Carbocyclyl:

The term "carbocyclyl" as used either alone or in combination with another radical, means a mono- bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems.

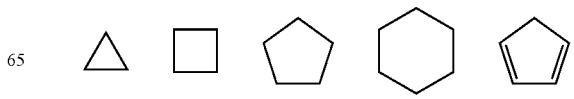

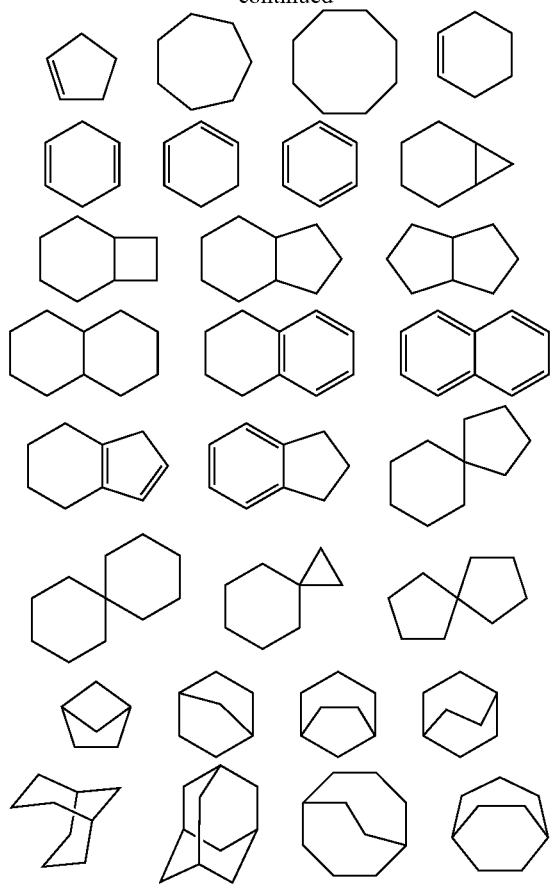

Cycloalkyl:
The term "C$_{3-n}$-cycloalkyl", wherein n is an integer from 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

Cycloalkenyl:
The term "C$_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term C$_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

Aryl:
The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heterocyclyl:
The term "heterocyclyl" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocycle" is intended to include all the possible isomeric forms.

Heteroaryl:
The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

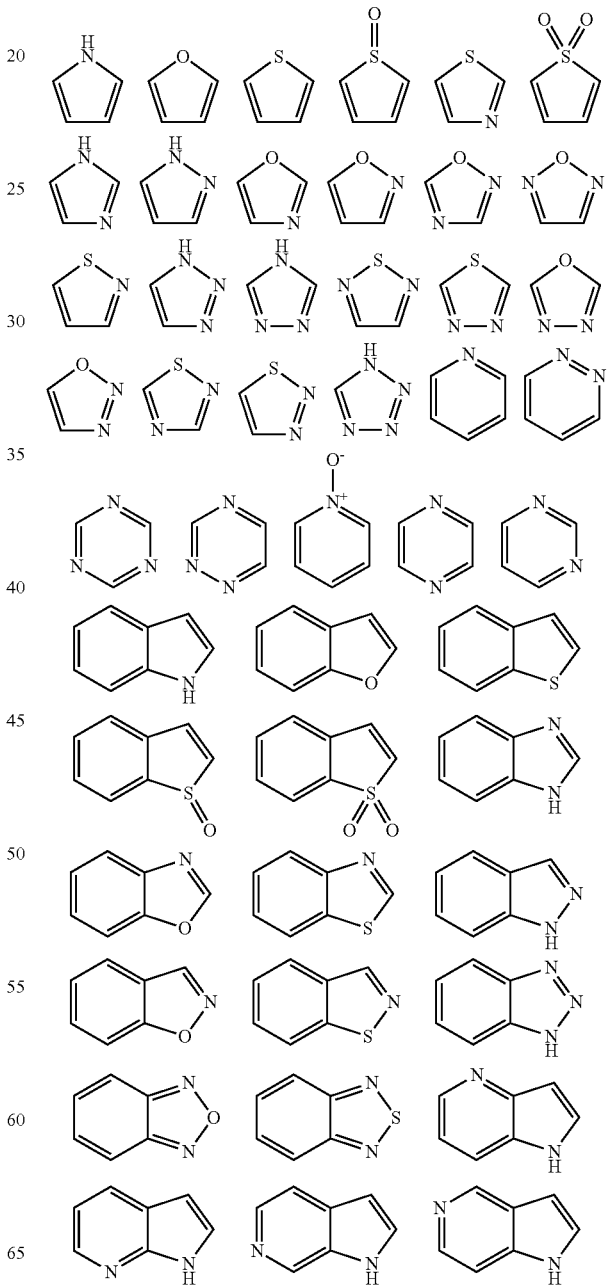

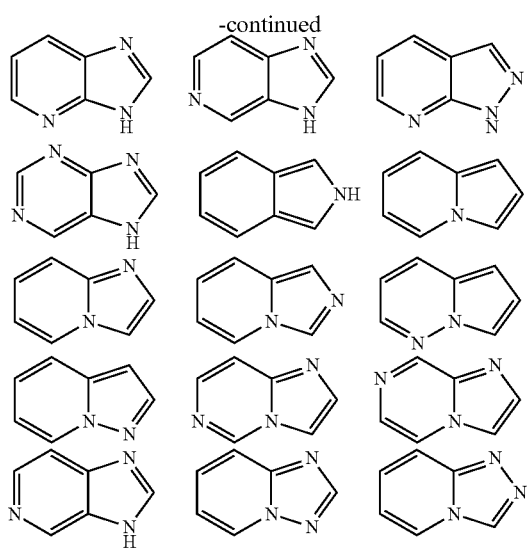
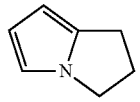

Many of the terms given above may be used repeatedly in the definition of a formula or group and in each case have one of the meanings given above, independently of one another.

GENERAL METHOD OF PREPARATION

Compounds of the present invention can be prepared in accordance with techniques that are well known to those skilled in the art.

Compounds of the present invention can be synthesized according to the following scheme:

Scheme 1

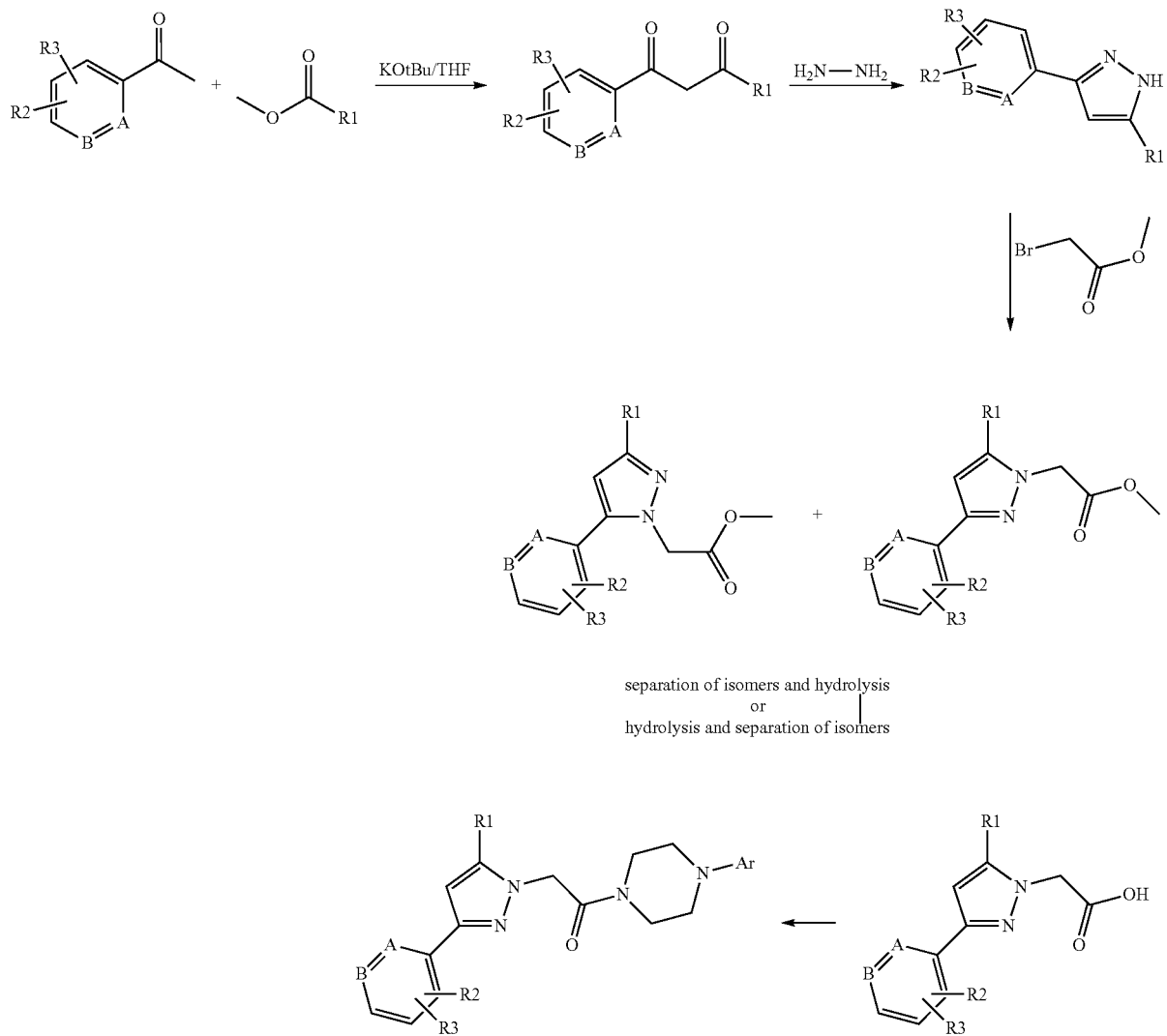

separation of isomers and hydrolysis
or
hydrolysis and separation of isomers

Aryl ketones were deprotonated with potassium tert butoxide and condensed with a methylesters to form a di-keton. Then, the di-keton was condensed with hydrazine to yield a pyrazole-system. The pyrazoles were coupled with 2-bromoacetic acid methyl ester under basic conditions to yield the desired pyrazol-1-yl-acetic acid methyl ester together with different quantities of the isomeric system. The pyrazol-1-yl-acetic acids methyl esters were hydrolyzed with LiOH to the corresponding acid. The isomers were either separated before or after hydrolysis of the ester. Finally, the pyrazol-1-yl-acetic acids were coupled with aryl substituted piperazines to the desired products.

Alternatively, the compounds of invention can be synthesized according to scheme 2:

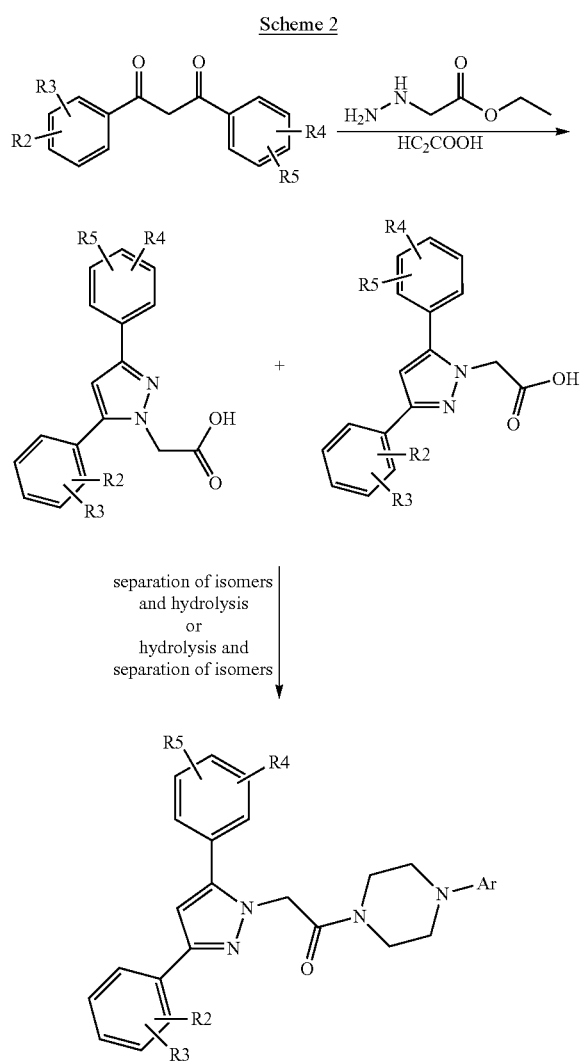

In this case the di-keton-systems were directly condensed with hydrazino-acetic acid ethyl ester to yield the two isomeric pyrazol-1-yl-acetic acid esters under acidic conditions. Then, the target compounds were obtained following the same synthesis strategy as for scheme 1.

As an additional alternative, the compounds of invention can be synthesized according to scheme 3:

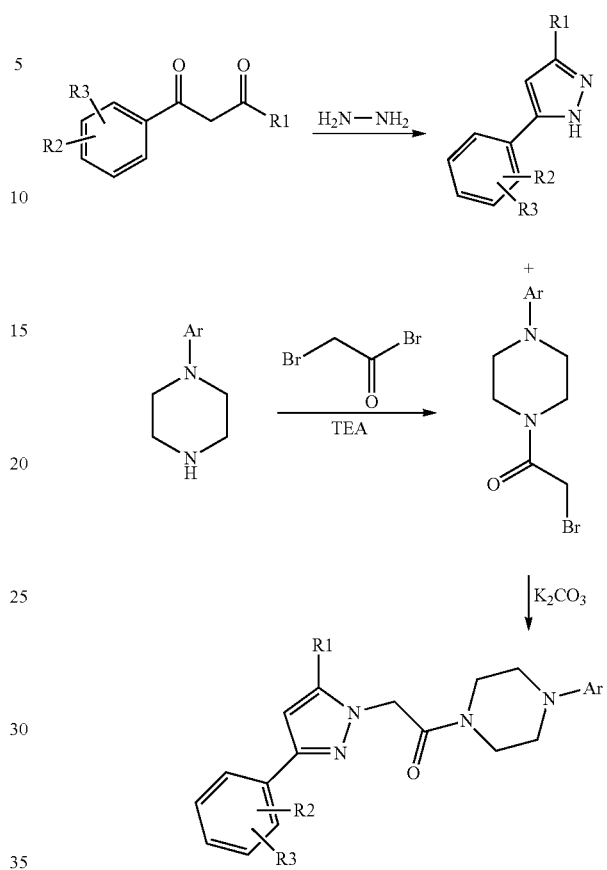

The pyrazole-systems were formed following the same strategy as illustrated in scheme 1 or they are commercial available. However, in this case the aryl piperazines were first coupled with bromacetylbromide under basic conditions. Subsequently, the bromo-arylpiperazinyl-ethanon derivates were coupled with the pyrazoles to the desired products.

Biological Assay

The positive modulation of mGluR5 is measured in a HEK 293 cell line expressing human recombinant mGluR5 and is detected with calcium based FLIPR assay. The cells are cultured with DMEM supplemented with 10% FCS, 2 μg/mL tetracycline, 100 μg/mL hygromycin and 500 μg/mL gneticin. The cell culture media is exchanged for tetracycline-free cell culture media 3-7 days before the assay. One day before the assay the cell culture medium is exchanged to DMEM without glutamine and phenol red and supplemented with 10% FCS, 100 μg/mL hygromycin and 500 μg/mL geneticin. On the assay day, the medium of the subconfluent cultures is removed and the cells are detached by addition of 2.5 ml EDTA(0.02%) per 175 cm2 culture flask for 1 minute. The cells are resuspend in Ringer solution (140 mM NaCl, 5 mM KCl, 2.5 mM CaCl2, 1.5 mM MgCl2, 5 mM Glucose, 10 mM Hepes; adjusted to pH 7.4 with NaOH), pooled and Ringer solution added to adjust the volume to 50 mL. The cell suspension is centrifuged for 5 min at 1500 U/min (425 g). The supernatant is removed and the cells washed a second time with 50 ml fresh Ringer solution and centrifuged again as before. The supernatant is again removed and the pellet resuspended in Ringer solution to 1,000,000 cells/ml (1×10^6 cells/mL). The cells are plated onto BD BioCoat Poly-D-Lysine 384 well plates (20.000 cells/well; 20 μl/well). The lid covered plates are then incubated until use at 37° C./10% $CO_2$. For dye loading, 20 μl of Calcium-4 assay kit solution (prepared according to the manufacturer's description in Ringer solution) are added to the cells and the plates are incubated for 80 min 37° C. and then 10 min at room temperature.

Controls, Compound Dilution and Assay Execution:

Each assay plate contained wells with "high" and "low" controls:

Low controls 1% DMSO/ringer solution+basal glutamate activation (defined as 100% CTL).

High controls 10 μM CDPPB+basal glutamate activation (defined as 200% CTL).

Test compounds are dissolved and diluted in DMSO to 100-fold the desired concentrations. In a second step, the compounds are diluted in Ringer solution such that the compounds are 4-fold more concentrated than the desired final assay concentration. The final DMSO concentration was 1%.

20 μl of each compound solution are then transferred to the assay plate and the Ca2+ kinetic is measured to determine any intrinsic compound activity. After 5 min incubation in the FLIPR device, the second stimulation with 20 μl of glutamate in Ringer solution (glutamate concentration adjusted to approximately 5% basal stimulation of the maximal possible glutamate effect) is added and the kinetic Ca2+ response of the wells was measured for the modulation effect.

Analysis:

The peak height of the Ca release related fluorescence signal (9-66) is used for the EC50. The EC50 of the modulation is calculated over a nonlinear regression with GraphPad Prism (Table 1).

TABLE 1

| Example | EC50 [nM] | Example | EC50 [nM] | Example | EC50 [nM] | Example | EC50 [nM] |
|---|---|---|---|---|---|---|---|
| 7.01.01 | 6 | 7.01.36 | 308 | 7.02.17 | 182 | 7.01.128 | 204 |
| 7.01.02 | 9 | 7.01.37 | 298 | 7.02.18 | 211 | 7.01.129 | 212 |
| 7.01.03 | 11 | 7.01.38 | 100 | 7.02.19 | 1201 | 7.01.130 | 471 |
| 7.01.04 | 11 | 7.01.39 | 170 | 7.02.20 | 183 | 7.01.131 | 59 |
| 7.01.05 | 44 | 7.01.40 | 224 | 7.01.85 | 371 | 7.01.132 | 138 |
| 7.01.06 | 99 | 7.01.41 | 234 | 7.01.86 | 1476 | 7.01.133 | 652 |
| 7.02.01 | 35 | 7.01.42 | 101 | 7.01.87 | 69 | 7.01.134 | 865 |
| 7.02.02 | 428 | 7.01.43 | 725 | 7.01.88 | 366 | 7.01.135 | 21 |
| 7.02.03 | 29 | 7.01.44 | 176 | 7.01.89 | 577 | 7.01.136 | 38 |
| 7.02.04 | 393 | 7.01.45 | 1006 | 7.01.90 | 157 | 7.01.137 | 57 |
| 7.02.05 | 85 | 7.01.46 | 333 | 7.01.91 | 195 | 7.01.138 | 230 |
| 7.02.06 | 581 | 7.01.47 | 447 | 7.01.92 | 302 | 7.01.139 | 595 |
| 7.01.07 | 621 | 7.01.48 | 687 | 7.01.93 | 170 | 7.01.140 | 707 |
| 7.01.08 | 349 | 7.01.49 | 1060 | 7.01.94 | 136 | 7.01.141 | 346 |
| 7.01.09 | 373 | 7.01.50 | 512 | 7.01.95 | 237 | 7.01.142 | 704 |
| 7.01.10 | 750 | 7.01.51 | 485 | 7.01.96 | 168 | 7.02.26 | 36 |
| 7.01.11 | 1418 | 7.01.52 | 431 | 7.01.97 | 181 | 7.05.01 | 40 |
| 7.01.12 | 216 | 7.01.53 | 569 | 7.01.98 | 13 | 7.05.02 | 38 |
| 7.02.07 | 853 | 7.01.54 | 205 | 7.01.99 | 129 | 7.01.143 | 20 |
| 7.02.08 | 934 | 7.01.55 | 501 | 7.01.100 | 126 | 7.01.144 | 57 |
| 7.02.09 | 298 | 7.01.56 | 393 | 7.01.101 | 17 | 7.01.145 | 216 |
| 7.02.10 | 948 | 7.01.57 | 81 | 7.01.102 | 20 | 7.01.146 | 25 |
| 7.02.11 | 91 | 7.01.58 | 211 | 7.01.103 | 24 | 7.01.147 | 19 |
| 7.02.12 | 1255 | 7.01.59 | 118 | 7.01.104 | 39 | 7.01.148 | 20 |
| 7.02.13 | 696 | 7.01.60 | 1228 | 7.02.21 | 77 | 7.01.149 | 12 |
| 7.02.14 | 129 | 7.01.61 | 246 | 7.02.22 | 85 | 7.01.150 | 5 |
| 7.03.01 | 31 | 7.01.62 | 48 | 7.02.23 | 60 | 7.01.151 | 19 |
| 7.01.13 | 14 | 7.01.63 | 94 | 7.02.24 | 340 | 7.01.152 | 26 |
| 7.01.14 | 22 | 7.01.64 | 677 | 7.02.25 | 92 | 7.01.153 | 276 |
| 7.01.15 | 30 | 7.01.65 | 253 | 7.01.105 | 4 | 7.01.154 | 11 |
| 7.01.16 | 32 | 7.01.66 | 957 | 7.01.106 | 35 | 7.01.155 | 24 |
| 7.04.01 | 696 | 7.04.03 | 392 | 7.01.107 | 64 | 7.01.156 | 33 |
| 7.04.02 | 81 | 7.01.67 | 61 | 7.01.108 | 1260 | 7.01.157 | 35 |
| 7.01.17 | 117 | 7.01.68 | 74 | 7.01.109 | 140 | 7.01.158 | 79 |
| 7.01.18 | 285 | 7.01.69 | 79 | 7.01.110 | 137 | 7.01.159 | 39 |
| 7.01.19 | 86 | 7.01.70 | 41 | 7.01.111 | 24 | 7.01.160 | 250 |
| 7.01.20 | 183 | 7.01.71 | 51 | 7.01.112 | 120 | 7.01.161 | 297 |
| 7.01.21 | 111 | 7.01.72 | 63 | 7.01.113 | 94 | 7.01.162 | 343 |
| 7.01.22 | 701 | 7.01.73 | 419 | 7.01.114 | 153 | 7.01.163 | 490 |
| 7.01.23 | 221 | 7.01.74 | 253 | 7.01.115 | 65 | 7.01.164 | 42 |
| 7.01.24 | 79 | 7.01.75 | 421 | 7.01.116 | 89 | 7.01.165 | 4 |
| 7.01.25 | 112 | 7.01.76 | 388 | 7.01.117 | 28 | 7.01.166 | 8 |
| 7.01.26 | 138 | 7.01.77 | 697 | 7.01.118 | 18 | 7.01.167 | 7 |
| 7.01.27 | 64 | 7.01.78 | 723 | 7.01.119 | 19 | 7.01.168 | 12 |
| 7.01.28 | 64 | 7.01.79 | 26 | 7.01.120 | 20 | 7.01.169 | 11 |
| 7.01.29 | 158 | 7.01.80 | 45 | 7.01.121 | 34 | 7.01.170 | 22 |
| 7.01.30 | 987 | 7.01.81 | 13 | 7.01.122 | 51 | 7.01.171 | 9 |
| 7.01.31 | 208 | 7.01.82 | 33 | 7.01.123 | 36 | 7.01.172 | 152 |
| 7.01.32 | 75 | 7.01.83 | 52 | 7.01.124 | 8 | 7.01.173 | 11 |
| 7.01.33 | 161 | 7.01.84 | 67 | 7.01.125 | 29 | 7.02.27 | 243 |
| 7.01.34 | 60 | 7.02.15 | 153 | 7.01.126 | 19 | 7.01.189 | 48 |
| 7.01.35 | 213 | 7.02.16 | 237 | 7.01.127 | 34 | 7.01.190 | 47 |
| 7.01.174 | 3 | 7.01.179 | 46 | 7.01.184 | 145 | 7.01.191 | 7 |
| 7.01.175 | 10 | 7.01.180 | 64 | 7.01.185 | 442 | 7.01.192 | 15 |
| 7.01.176 | 10 | 7.01.181 | 130 | 7.01.186 | 441 | | |

TABLE 1-continued

| Example | EC50 [nM] | Example | EC50 [nM] | Example | EC50 [nM] | Example | EC50 [nM] |
|---|---|---|---|---|---|---|---|
| 7.01.177 | 24 | 7.01.182 | 434 | 7.01.187 | 360 | | |
| 7.01.178 | 21 | 7.01.183 | 318 | 7.01.188 | 27 | | |

Method of Treatment

The present invention is directed to compounds of general formula I which are useful in the treatment of a disease and/or condition wherein the activity of an mGluR5 positive modulator is of therapeutic benefit, including but not limited to the treatment of psychotic disorders, cognitive disorders and dementias.

The compounds of general formula I are useful for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia. Therefore, the present invention also relates to a compound of general formula I as a medicament.

A further aspect of the present invention relates to the use of a compound of general formula I for the treatment of a disease and/or condition wherein the activity of mGluR5 positive modulator is of therapeutic benefit.

Furthermore, the present invention relates to the use of a compound of general formula I for the treatment of psychotic disorders, cognitive disorders and dementias.

Furthermore, the present invention relates to the use of a compound of general formula I for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

In a further aspect of the present invention the present invention relates to methods for the treatment or prevention of above mentioned diseases and conditions, which method comprises the administration of an effective amount of a compound of general formula I to a human being.

Dosage

The dose range of the compounds of general formula I applicable per day is usually from 0.1 to 5000 mg, preferably from 0.1 to 1000 mg, more preferably from 5 to 500 mg, most preferably, 10 or 100 mg. Each dosage unit may conveniently contain from 0.1 to 500 mg, preferably 10 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

A further aspect of the invention is a pharmaceutical formulation including a compound of formula I in admixture with a pharmaceutically acceptable adjuvant, diluent or carrier.

Combination Therapy

In another aspect the present invention relates to a combination therapy in which an active compound according to the present invention is administered together with another active compound. Accordingly, the invention also refers to pharmaceutical formulations that provide such a combination of active ingredients, whereby one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies, nanobodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride, imipramine maleate, lofepramine, desipramine, doxepin, trimipramine.

Or the active compounds according to the invention also may be combined with serotonin (5-HT) reuptake inhibitors such as alaproclate, citalopram, escitalopram, clomipramine, duloxetine, femoxetine, fenfluramine, norfenfluramine, fluoxetine, fluvoxamine, indalpine, milnacipran, paroxetine, sertraline, trazodone, venlafaxine, zimelidine, bicifadine, desvenlafaxine, brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

| Abbreviations | |
| --- | --- |
| RT | room temperature |
| THF | tetrahydrofuran |
| KotBu | kalium tert butoxide |
| PFTU | pentafluorphenol-tetramethyluronium hexafluorophosphat |
| ACN | acetonitrile |
| MeOH | methanol |
| DIPEA | diisopropylamine |
| DEA | diethylamine |
| EtOAC | ethyl acetate |
| DMF | dimethylformamide |
| TBTU | [Benzotriazol-1-yloxy)-dimethylamino-methylene]-dimethyl-ammonium tetrafluoro borate |
| HATU | (O-(7-Azobenzotriazol-1-yl)-1,1,3,3-tetramethyluroniumhexafluorophosphate |
| conc. | concentrated |
| min. | minutes |
| DCM | dichlormethane |

Analytical Methods

All compounds specified in the examples below gave the correct mass spectra matching the theoretical isotope pattern. For practical reasons, only one of the major isotope peaks is given as representative data for the mass spectrum.

List of HPLC Purification Methods:

Method 1:
Gilson HPLC
eluent:
A: water with 0.10% TFA
B: methanol
gradient

| time in min | % A | % B | flow in ml/min |
|---|---|---|---|
| 00.00 | 90 | 10 | 50 |
| 02.00 | 90 | 10 | 50 |
| 11.00 | 0 | 100 | 50 |
| 14.00 | 0 | 100 | 50 | column: Sunfire C18, 30×100 mm, 10 μm (temperature: isocratic 60° C.).
Method 2:
column: Daicel OJH, 250 mm×4.6 mm,
flow: 4 ml/min,
run time: 10 min,
mobile phases: $CO_2$, 20% Methanol with DEA
The HPLC/MS data, where specified, are obtained under the following conditions:
List of Analytical HPLC-methods:
Method A:
Waters Acquity with diodenarraydetector and massdetector
eluent:
A: water with 0.10% TFA
B: methanol
gradient

| time in min | % A | % B | flow in ml/min |
|---|---|---|---|
| 0.00 | 99 | 1 | 1.20 |
| 0.05 | 99 | 1 | 1.20 |
| 1.05 | 0 | 100 | 1.20 |
| 1.25 | 0 | 100 | 1.20 | column: Sunfire C18, 2.1×30 mm, 2.5 μm (temperature: isocratic 60° C.).
diodenarray detektion: 210-400 nm.
Method B:
Waters ZQ MS, Alliance 2690/2695 HPLC, Waters 996/2996 diodenarraydetector
eluent:
A: water with 0.10% TFA
D: methanol
gradient:

| time in min | % A | % D | flow in ml/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 | column: Waters XBridge™ C18 3.5 μm, 4.6×20 mm IS™ (temperature: isocratic 40° C.).
diodenarray detection: 210-400 nm.
Method C:
Waters ZMD, Alliance 2690/2695 HPLC, Waters 996/2996 diodenarraydetector
eluent:
A: water with 0.10% TFA
B: acetonitril with 0.10% TFA
gradient:

| time in min | % A | % B | flow in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 | column: Merck Chromolith™ Flash RP-18e, 3 mm×100 mm (temperature: isocratic 25° C.)
dioden array detection: 210-400 nm
Method D:
Waters Acquity with diodenarraydetector
eluent:
A: water with 0.13% TFA
B: methanol with 0.05% TFA
gradient:

| time in min | % A | % B | flow in ml/min |
|---|---|---|---|
| 0.00 | 99 | 1 | 1.20 |
| 0.05 | 99 | 1 | 1.20 |
| 1.05 | 0 | 100 | 1.20 |
| 1.25 | 0 | 100 | 1.20 | column: Sunfire C18, 2.1×30 mm, 2.5 μm (temperature: isocratic 60° C.).
Method E:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.90 |
| 1.60 | 0 | 100 | 4.90 |
| 2.20 | 95 | 5 | 4.90 | column: Sunfire C18, 4.6×30 mm, 3.5 μm (temperature: isocratic 60° C.).
Method F:
Agilent 1200 mit DA- and MS-Detektor
eluent:
A: water with 0.10% TFA
B: methanol
gradient:

| time in min | % A | % B | flow in ml/min |
|---|---|---|---|
| 0.00 | 95 | 5 | 1.80 |
| 0.20 | 95 | 5 | 1.80 |
| 1.70 | 0 | 100 | 1.80 |
| 1.75 | 0 | 100 | 2.50 |
| 2.20 | 0 | 100 | 2.50 | column: Sunfire C18, 3×30 mm, 2.5 μm (temperature: isocratic 60° C.).
Method G:
Waters Alliance with diodenarraydetector and massdetector
eluent:
A: water with 0.10% TFA
B: methanol with 0.10% TFA gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |
| 1.85 | 95 | 5 | 4.00 | column: XBridge C18, 4.6×30 mm, 3.5 µm (temperature: isocratic 60° C.).
Method H:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.90 |
| 1.50 | 0 | 100 | 4.90 |
| 2.20 | 95 | 5 | 4.90 | column: XBridge C18, 4.6×30 mm, 3.5 µm (temperature: isocratic 60° C.).
Method I:
Waters Acquity with diodenarraydetector and massdetector
eluent:
A: water with 0.10% TFA
B: methanol
gradient

| time in min | % A | % B | flow in ml/min |
|---|---|---|---|
| 0.00 | 99 | 1 | 1.50 |
| 0.05 | 99 | 1 | 1.50 |
| 1.05 | 0 | 100 | 1.50 |
| 1.20 | 0 | 100 | 1.50 | column: Xbridge C18, 2.1×30 mm, 1.7 µm (temperature: isocratic 60° C.).
Method J:
Waters Acquity with diodenarraydetector and massdetector
eluent:
A: water with 0.13% TFA
B: methanol with 0.08% TFA
gradient:

| time in min | % A | % B | flow in ml/min |
|---|---|---|---|
| 0.00 | 99 | 1 | 1.30 |
| 0.05 | 99 | 1 | 1.30 |
| 0.35 | 0 | 100 | 1.30 |
| 0.50 | 0 | 100 | 1.30 | column: Xbridge C18, 2.1×30 mm, 1.7 µm (temperature: isocratic 60° C.).
Method K:
Waters Alliance with diodenarraydetector and massdetector
eluent:
A: water with 0.10% NH3
B: methanol with 0.10% NH3
gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 | column: XBridge C18, 4.6×30 mm, 3.5 µm (temperature: isocratic 60° C.).
Method L:
Waters ZQ 2000MS, Agilent HP100, binäre pumps
eluent:
A: water with 0.10% TFA
B: methanol
gradient:

| time in min | % A | % B | flow in ml/min |
|---|---|---|---|
| 0.00 | 95 | 5 | 1.50 |
| 1.30 | 0 | 100 | 1.50 |
| 2.50 | 0 | 100 | 1.50 |
| 2.60 | 95 | 5 | 1.50 | column: Sunfire C18, 4.6×50 mm, 3.5 µm (temperature: isocratic 40° C.).
diodenarray detection: 210-400 nm
Method M:
Waters Acquity with diodenarraydetector and massdetector
eluent:
A: water with 0.10% TFA
B: methanol
gradient:

| time in min | % A | % B | flow in ml/min |
|---|---|---|---|
| 0.00 | 99 | 1 | 1.30 |
| 0.15 | 99 | 1 | 1.30 |
| 1.10 | 0 | 100 | 1.30 |
| 1.25 | 0 | 100 | 1.30 | column: Sunfire C18, 2.1×30 mm, 2.5 µm (temperature: isocratic 60° C.).
diodenarray detektion: 210-400 nm.
Method N:
Agilent 1100 System with diodenarraydetector and massdetector
eluent:
A: water with 0.10% ammonia
B: methanol
gradient:

| time in min | % A | % B | flow in ml/min |
|---|---|---|---|
| 0.00 | 95 | 5 | 4.00 |
| 0.15 | 95 | 5 | 4.00 |
| 1.70 | 0 | 100 | 4.00 |
| 2.10 | 0 | 100 | 4.00 | column: Stable Bond C18, 4.6×30 mm, 3.5 µm (temperature: isocratic 60° C.).
Method O:
Agilent 1100 System with diodenarraydetector and massdetector
eluent:
A: water with 0.10% TFA
B: methanol with 0.10% TFA gradient:

| time in min | % A | % B | flow in ml/min |
|---|---|---|---|
| 0.00 | 95 | 5 | 4.00 |
| 0.15 | 95 | 5 | 4.00 |
| 1.70 | 0 | 100 | 4.00 |
| 2.25 | 0 | 100 | 4.00 | column: Sunfire C18, 4.6×30 mm, 3.5 µm (temperature: isocratic 60° C.).
Method P:
Agilent 1200 mit DA- and MS-Detektor
eluent:
A: water with 0.20% TFA
B: methanol
gradient:

| time in min | % A | % B | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 | column: Stable Bond C18, 3×30 mm, 1.8 µm (temperature: isocratic 60° C.).
Method Q:
Waters Acquity with diodenarraydetector and massdetector
eluent:
A: water with 0.10% TFA
B: methanol
gradient

| time in min | % A | % B | flow in ml/min |
|---|---|---|---|
| 0.00 | 99 | 1 | 1.40 |
| 0.05 | 99 | 1 | 1.40 |
| 1.00 | 0 | 100 | 1.40 |
| 1.10 | 0 | 100 | 1.40 | column: Xbridge C18, 2.1×20 mm, 2.5 µm (temperature: isocratic 60° C.).
Method R:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.80 |
| 1.60 | 0 | 100 | 4.80 |
| 1.85 | 0 | 100 | 4.80 |
| 1.90 | 95 | 5 | 4.80 | column: XBridge C18, 4.6×30 mm, 3.5 µm (temperature: isocratic 60° C.).
Method S:
Agilent 1200 mit DA- and MS-Detektor
eluent:
A: water with 0.20% TFA
B: methanol gradient:

| time in min | % A | % B | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 | column: Sunfire C18, 3×30 mm, 2.5 µm (temperature: isocratic 60° C.).
Method T:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.00 |
| 1.60 | 0 | 100 | 4.00 |
| 1.85 | 0 | 100 | 4.00 |
| 1.90 | 95 | 5 | 4.00 | column: XBridge C18, 4.6×30 mm, 3.5 µm (temperature: isocratic 60° C.).
Method U:
Waters Acquity with diodenarraydetector and massdetector
eluent:
A: water with 0.13% TFA
B: methanol 0.05% TFA
gradient

| time in min | % A | % B | flow in ml/min |
|---|---|---|---|
| 0.00 | 99 | 1 | 1.30 |
| 0.05 | 99 | 1 | 1.30 |
| 1.05 | 0 | 100 | 1.30 |
| 1.20 | 0 | 100 | 1.30 | column: Xbridge BEH C18, 2.1×30 mm, 1.7 µm (temperature: isocratic 60° C.
Method V:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.00 |
| 1.60 | 0 | 100 | 4.00 |
| 1.85 | 0 | 100 | 4.00 |
| 1.90 | 95 | 5 | 4.00 | column: SunFire C18, 4.6×30 mm, 3.5 µm (temperature: isocratic 60° C.).
Method W:
Waters ZQ2000 with diodenarraydetector and massdetector
eluent:
A: water with 0.15% formic acid
B: methanol gradient:

| time in min | % A | % B | flow in ml/min |
|---|---|---|---|
| 0.00 | 95 | 5 | 1.50 |
| 2.00 | 0 | 100 | 1.50 | column: Xbridge C18, 2.1×50 mm, 3.5 μm (temperature: isocratic 40° C.).
Method X:
Agilent 1200 mit DA- and MS-Detektor
eluent:
A: water with 0.10% ammonia
B: methanol
gradient:

| time in min | % A | % B | flow in ml/min |
|---|---|---|---|
| 0.00 | 95 | 5 | 2.20 |
| 0.20 | 95 | 5 | 2.20 |
| 1.50 | 0 | 100 | 2.20 |
| 1.55 | 0 | 100 | 2.90 |
| 1.70 | 0 | 100 | 2.90 | column: Xbridge C18, 3×30 mm, 2.5 μm (temperature: isocratic 60° C.).
Method Y:
Waters Alliance with diodenarraydetector and massdetector
eluent:
A: water with 0.10% NH3
B: methanol with 0.10% NH3
gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 | column: XBridge C18, 4.6×30 mm, 3.5 μm (temperature: isocratic 60° C.).
Method Z:
Waters Acquity with diodenarraydetector and massdetector
eluent:
A: water with 0.1% TFA
B: methanol
gradient

| time in min | % A | % B | flow in ml/min |
|---|---|---|---|
| 0.00 | 99 | 1 | 1.50 |
| 0.05 | 99 | 1 | 1.50 |
| 1.05 | 0 | 100 | 1.50 |
| 1.20 | 0 | 100 | 1.50 | column: Xbridge BEH Phenyl, 2.1×30 mm, 1.7 μm (temperature: isocratic 60° C.)
Method AA:
Waters Acquity with diodenarraydetector and massdetector
eluent:
A: water with 0.1% TFA
B: methanol
gradient

| time in min | % A | % B | flow in ml/min |
|---|---|---|---|
| 0.00 | 99 | 1 | 1.50 |
| 0.05 | 99 | 1 | 1.50 |
| 1.00 | 0 | 100 | 1.50 |
| 1.10 | 0 | 100 | 1.50 | column: Xbridge Phenyl, 2.1×20 mm, 2.5 μm (temperature: isocratic 60° C.)
Method AB:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.00 |
| 1.60 | 0 | 100 | 4.00 |
| 1.85 | 0 | 100 | 4.00 |
| 1.90 | 95 | 5 | 4.00 | column: XBridge C18, 4.6×30 mm, 3.5 μm (temperature: isocratic 60° C.).
Method AC:
Waters Alliance with diodenarraydetector and massdetector
eluent:
A: water with 0.10% TFA
B: methanol
gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.90 | 0 | 100 | 4.00 |
| 2.20 | 95 | 5 | 4.00 | column: XBridge C18, 4.6×30 mm, 3.5 μm (temperature: isocratic 60° C.).
Method AD:
Waters Alliance with diodenarraydetector and massdetector
eluent:
A: water with 0.10% NH3
B: methanol
gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 | column: XBridge C18, 4.6×30 mm, 3.5 μm (temperature: isocratic 60° C.).
Method AE:
Waters SQD MS, Acquity UPLC with diodenarraydetector
eluent:
A: water with 0.10% TFA
B: acetonitrile 0.08% TFA gradient:

| time in min | % A | % B | flow in ml/min |
|---|---|---|---|
| 0.00 | 95 | 5 | 1.50 |
| 0.70 | 0 | 100 | 1.50 |
| 0.80 | 0 | 100 | 1.50 |
| 0.81 | 95 | 5 | 1.50 | column: Ascentis Express C18, 2.1×50 mm, 2.7 μm (temperature: isocratic 60° C.).

Synthesis of Intermediates 6.01. Synthesis of Building Blocks 6.01.01 4-methoxy-6-piperazin-1-yl-pyrimidine hydrochloride

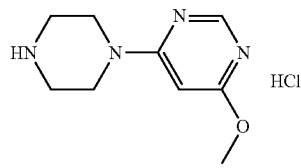

6.01.01.1 4-chloro-6-methoxy-pyrimidine 5.8 g sodium methanolate was added to 10 g 4,6-dichloro-pyrimidine in 150 mL MeOH at 0° C. The reaction was warmed up to RT and stirred over night at RT. Then 3.63 g sodium methanolate was added and the reaction was stirred for 3 h. The mixture was treated with water and extracted with EtOAc. The organic layer was dried over magesiumsulfate and evaporated to give 9.7 g 4-chloro-6-methoxy-pyrimidine.
$R_t$: 0.87 min (method B)
$(M+H)^+$: 145

6.01.01.2 4-(6-methoxy-pyrimidin-4-yl)-piperazine-1-carboxylic acid tert-butyl ester 18.6 mL triethylamine and piperazine-1-carboxylic acid tert-butyl ester were added to 9.7 g 4-chloro-6-methoxy-pyrimidine in 50 mL DMF. The reaction was stirred over night at 60° C. The reaction was cooled and the precipitate was filtered. The filtrate was evaporated. The residue was dissolved in DCM, extracted with water and washed with sodium chloride solution. The solvent was evaporated and the residue was crystallized with a mixture of petrolether and diethylether (8:2) to yield 8.7 g of the desired compound.
$R_t$: 1.12 min (method B)
$(M+H)^+$: 195

6.01.01.3 4-methoxy-6-piperazin-1-yl-pyrimidine hydrochloride 8.61 g 4-(6-Methoxy-pyrimidin-4-yl)-piperazine-1-carboxylic acid tert-butyl ester were stirred in 4 mol/L HCl solution in dioxane for 1 h. The precipitates was filtered, washed with dioxane and dried to yield 5.17 g of the desired compound.
$R_f$: 0.75 (flash chromatography: silica gel, cyclohexane: EtOAc/NH3 (3:1))
$(M+H)^+$: 295

By using the same synthesis strategy as for 4-methoxy-6-piperazin-1-yl-pyrimidine hydrochloride the following compounds were obtained:

| Examples | Product | MS m/z $[M+H]^+$ | HPLC Method | Rt min |
|---|---|---|---|---|
| 6.01.02 | | 195 | method K | 0.18 |
| 6.01.03 | | 195 | method H | 0.46 |

6.01.04 1-Pyridin-3-yl-piperazine 6.01.04.1 1-Benzyl-4-pyridin-3-yl-piperazine 1.8 M phenyllithium solution in cyclohexane/diethylether (7/3) was dropped to cooled 25 g 3-fluoropyridine and 59 g n-benzylpiperazine in 600 mL diethylether. The reaction was warmed up to RT and stirred over night at RT. 150 mL water was dropped to the mixture and the organic layer was dried and evaporated. The residue was cleaned on silica gel (dichlormethane/cyclohexane/methanol (5/5/1)) to yield 31.3 g of the desired compound.

6.01.04.2 1-Pyridin-3-yl-piperazine 31.3 g 1-Benzyl-4-pyridin-3-yl-piperazin was hydrogenated at 5 bar on 4 g 10% palladium on charcoal in 300 mL methanol at 50° C. for 25 h. The reaction was filtered. The filtrate was evaporated and purified by chromatography on silica gel (dichlormethane/methanol/ammonia (9/1/0.1)). 12.5 g of the desired compound was obtained.

6.01.05 2-bromo-1-(4-pyrimidin-2-yl-piperazin-1-yl)-ethanon

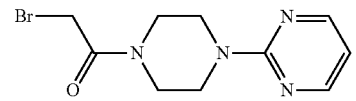

6.01.05.1 2-bromo-1-(4-pyrimidin-2-yl-piperazin-1-yl)-ethanon 20.2 g bromacetylbromide was dropped to 16.5 g 1-pyrimidin-2-yl-piperazin and 10.2 g triethylamine in 250 mL THF. The reaction was stirred over night at RT and evaporated. The residue was extracted with DCM and water. The organic layer was evaporated and the residue was crystallized with petrolether and then purified by chromatography on silica gel (DCM/MeOH:95/5) to yield 36 mg of the desired compound.

$R_t$: 1.09 min (method C)

$(M+H)^+$: 286

6.01.06 5-fluoro-pyridine-2-carboxylic acid methyl ester

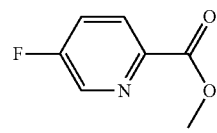

2.7 mL Thionylchloride was dropped to 5 g 5-fluor-pyridine-2-carboxylic acid in 50 mL methanol. The reaction was stirred for 2 h at 65° C. in a sealed micro wave vial. The solvents were removed and the residue was desolved in a mixture of DCM and methanol and filtered over silica gel. The filtrate was evaporated to give 5.9 g of the desired product.

$R_t$: 0.77 (method K). $(M+H)^+$: 156

By using the same synthesis strategy as for 5-fluoro-pyridine-2-carboxylic acid methyl ester the following compound was obtained:

| Example | Product | MS m/z $[M + H]^+$ | HPLC Method | Rt min |
|---|---|---|---|---|
| 6.01.07 | 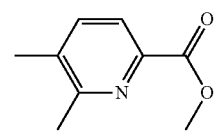 | 152 | method M | 0.60 |

6.01.08 5,6-dimethyl-pyridine-2-carboxylic acid methyl ester

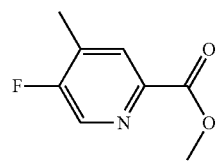

77.4 ml 2 mol/L trimethylsilyldiazomethan in hexane was added to 5,6-dimethyl-pyridine-2-carboxylic acid in 150 mL methanol and 600 mL dichlormethane at −5° C. The reaction was stirred 0.5 h at −5° C. and then warm up to RT. The solvent was removed and the residue was purified by chromatography on Silica (cyclohexane 7: ethyl acetate 3) to give 12.8 g desired product.

$R_t$: 0.49 (method M)

$(M+H)^+$: 166

6.01.09 4-chloro-6-piperazin-1-yl-pyrimidine

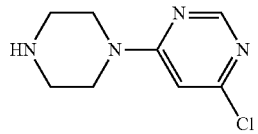 [SMILES: Clc1cc(N2CCNCC2)ncn1]

13.3 g tert-butyl 1-piperazinecarboxylate and 11.2 mL DIPEA were added to 10 g 4, 6 dichloro pyrimidine in 1000 mL dichlormethane was stirred over the weekend at RT. The solvent was removed. The residue was dissolved in 200 mL dichlormethane and 200 mL trifluoro acetic acid was added. The reaction was stirred at RT. The solvent was removed. The residue was dissolved in methanol and passed through HCO3 containing resin. The solvent was removed and the residue was purified by chromatographie on silica (dcyclohexane: ethylacetate 0-40%) to yield 13.07 g of the desired product.

$R_t$: 1.77 min (method W).

$(M+H)^+$: 199

6.01.10 5-fluoro-4-methyl-pyridine-2-carboxylic acid methyl ester 18 g 2-bromo-5-fluoro-4-methyl-pyridine, 1.5 g 1,1'-bis (diphenylphosphino) ferrocene dichloropalladium (II) and 18 g sodium acetate was stirred 17 h at 80° C. and 5 bar carbon monoxide. The reaction was filtered and the solvent was removed. Diethylether was added to the residue and the mixture was filtered. The filtrate was evaporated to give 12 g desired product.

$R_t$: 0.90 min. (method AB)

$(M+H)^+$: 170

By using the same synthesis strategy as for 5-fluoro-4-methyl-pyridine-2-carboxylic acid methyl ester the following compound was obtained:

| Example | Product | MS m/z $[M + H]^+$ | HPLC Method | Rt min |
|---|---|---|---|---|
| 6.01.11 | | 170 | method AB | 0.87 |

6.02. Synthesis of pyrazol-1yl-acids

6.02.01.01 1-(4-fluoro-3-methyl-phenyl)-3-phenyl-1,3-propanedione

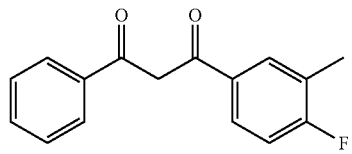 [SMILES: Cc1cc(C(=O)CC(=O)c2ccccc2)ccc1F]

17.3 g KOtBu was dissolved in 500 mL THF and 9 mL acetophenone was added. After 15 min at RT 25.9 g 4-fluoro-3-methyl-benzoic acid methyl ester was added and stirred for 3 h at RT. The solvent was removed and the residue was purified by chromatography on silica gel (cyclohexane/EE: 98:2) to yielded 19.3 g of the desired compound.

By using the same synthesis strategy as for 1-(4-fluoro-3-methyl-phenyl)-3-phenyl-1,3-propanedione the following compounds were obtained:

| Examples | Product | MS m/z $[M+H]^+$ | HPLC Method | Rt min |
|---|---|---|---|---|
| 6.02.01.02 | | 261 | method B | 1.67 |
| 6.02.01.03 | | 263 | method B | 1.73 |
| 6.02.01.04 | | 221 | method B | 1.53 |
| 6.02.01.05 | | 235 | | |
| 6.02.01.06 | | 223 | method M | 1.03 |
| 6.02.01.07 | | 209 | method R | 1.45 |

| Examples | Product | MS m/z [M + H]+ | HPLC Method | Rt min |
|---|---|---|---|---|
| 6.02.01.08 | | 253 | method M | 1.06 |
| 6.02.01.09 | | 195 | method M | 0.90 |
| 6.02.01.10 | | 253 | method T | 1.50 |
| 6.02.01.11 | | 240 | method M | 1.02 |
| 6.02.01.12 | | 237 | method T | 1.67 |
| 6.02.01.13 | | 254 | method M | 0.98 |
| 6.02.01.14 | | 205 | method Q | 0.89 |
| 6.02.01.15 | | 254 | method M | 0.98 |
| 6.02.01.16 | | 223 | method T | 1.63 |

| Examples | Product | MS m/z [M + H]+ | HPLC Method | Rt min |
|---|---|---|---|---|
| 6.02.01.17 | ![structure] | 265 | method M | 1.03 |
| 6.02.01.18 | ![structure] | 273 | method M | 1.00 |
| 6.02.01.19 | ![structure] | 250 | method V | 1.58 |

6.02.01.20
1,3-Bis-(4-fluoro-phenyl)-1,3-propanedione

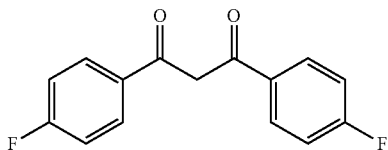 [SMILES: O=C(CC(=O)c1ccc(F)cc1)c1ccc(F)cc1]

9.27 g KOtBu was added to 109 mg 18-Krone-6 and 5 mL 4-fluoracetophenone in 150 mL THF. After 30 min at RT 10.7 g 4-fluoro-benzoic acid methyl ester was added and stirred for 3 h at RT. The reaction was decomposed with water and filtered, the filtrate was concentrated and the residue was purified by chromatography on silica gel (cyclohexane/EE: 98:2). The solvent was removed and 3.9 g of the desired compound was obtained.

(M+H)+: 261

By using the same synthesis strategy as for 1-(4-fluoro-3-methyl-phenyl)-3-phenyl-1,3-propanedione the following compounds were obtained:

| Examples | Product | MS m/z [M + H]+ | HPLC Method | Rt min |
|---|---|---|---|---|
| 6.02.01.21 | ![structure] | 221 | method B | 1.48 |
| 6.02.01.22 | ![structure] | 223 | method B | 1.59 |
| 6.02.01.23 | ![structure] | 239 | | |

-continued
| Examples | Product | MS m/z [M + H]+ | HPLC Method | Rt min |
|---|---|---|---|---|
| 6.02.01.24 | 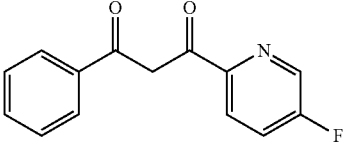 [SMILES: O=C(CC(=O)c1ccc(F)cn1)c1ccccc1] | 244 | method D | 1.08 |
| 6.02.01.25 | 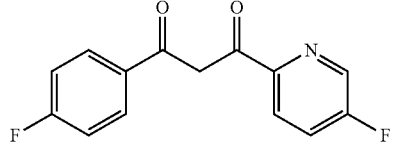 | 262 | method M | 1.09 |
| 602.01.26 | 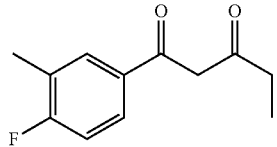 | 209 | method A | 1.05 |
| 6.02.01.27 | 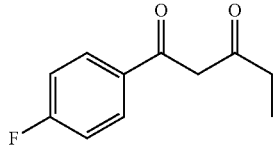 | 195 | method A | 1.00 |
| 6.02.01.28 | 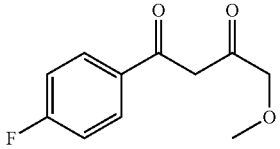 | 225 | method P | 1.20 |
| 6.02.01.29 | 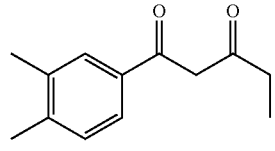 | 205 | method Q | 0.86 |
| 6.02.01.30 | 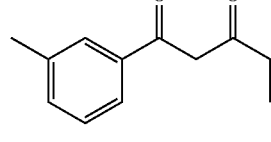 | 191 | method Q | 0.81 |
| 6.02.01.31 | 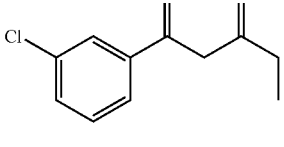 | 211/13 | method Q | 0.89 |
| 6.02.01.32 | 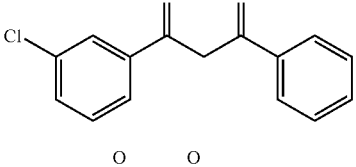 | 259 | method AB | 1.69 |
| 6.02.01.33 | 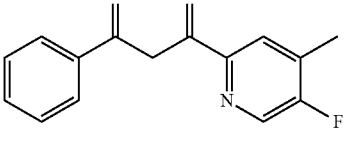 | 258 | method AB | 1.63 |

-continued

| Examples | Product | MS m/z [M + H]+ | HPLC Method | Rt min |
|---|---|---|---|---|
| 6.02.01.34 | 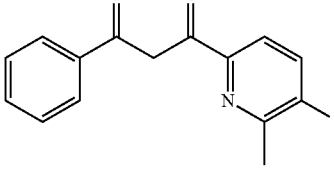 | 258 | method AB | 1.64 |
| 6.02.01.35 | 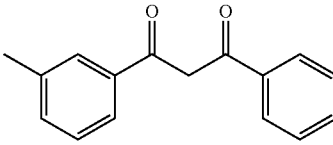 | 239 | method R | 1.56 |
| 6.02.01.36 | 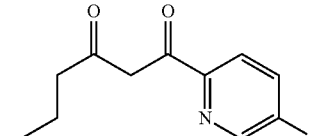 | 224 | method AB | 0.94 |
| 6.02.01.37 | 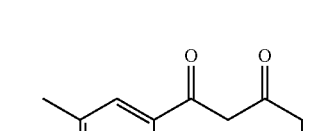 | 209 | method A | 0.96 |
| 6.02.01.38 | 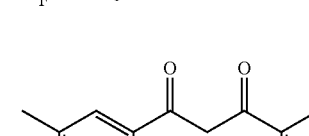 | 269 | Method R | 1.66 |
| 6.02.01.39 | 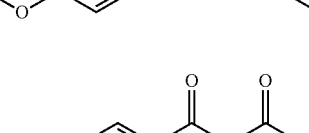 | 292 | method AB | 0.97 |

6.02.01.36
1-cyclohexyl-3-(4-fluoro-phenyl)-propane-1,3-dione

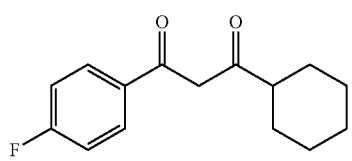 [SMILES: O=C(CC(=O)C1CCCCC1)c1ccc(F)cc1]

0.88 g 60% sodiumhydrid was added 1-cyclohexyl-ethanone in 60 mL THF and stirred for 30 min. Then, 3.25 g 4-fluoro-benzoic acid methyl ester and 200 mg 18-Krone-6 was added to the reaction. The reaction was refluxed 2 h and stirred over night at RT. The reaction was added to 100 mL 1N HCl and extracted with diethylether. The organic layer was concentrated and the residue was purified by chromatography on silica gel and 3 g of the desired compound was obtained.

$R_t$: 2.01 min (method B).

(M+H)+: 249

By using the same synthesis strategy as for 1-cyclohexyl-3-(4-fluoro-phenyl)-propane-1,3-dione the following compounds were obtained:

| Examples | Product | MS m/z [M + H]+ | HPLC Method | Rt min |
|---|---|---|---|---|
| 6.02.01.37 | 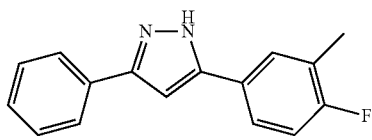 [SMILES: Cc1cc(-c2cc(-c3ccccc3)n[nH]2)ccc1F] | 283 | | |

6.02.02.01
3-(4-fluoro-3-methyl-phenyl)-5-phenyl-pyrazole 1.7 g 1-(4-fluoro-3-methyl-phenyl)-3-phenyl-1,3-propanedione was dissolved in 20 mL of a solution of 1 N hydrazine in THF and stirred for 3 h at 75° C. The solvent was removed and the residue was crystallized to give 1.7 g of the desired compound.

$R_t$: 1.07 min (method D)

$(M+H)^+$: 253

By using the same synthesis strategy as for 3-(4-fluoro-3-methyl-phenyl)-5-phenyl-pyrazole the following compounds were obtained:

| Examples | Product | MS m/z [M + H]+ | HPLC Method | Rt min |
|---|---|---|---|---|
| 6.02.02.02 | | 257 | method C | 1.67 |
| 6.02.02.03 | | 245 | method C | 1.61 |
| 6.02.02.04 | | 217 | method B | 1.27 |
| 6.02.02.05 | | 279 | method C | 1.62 |
| 6.02.02.06 | | 257 | method D | 1.03 |
| 6.02.02.07 | | 257 | method B | 1.51 |

-continued

| Examples | Product | MS m/z [M + H]+ | HPLC Method | Rt min |
| --- | --- | --- | --- | --- |
| 6.02.02.08 | | 219 | method B | 1.44 |
| 6.02.02.09 | | 259 | method B | 1.39 |
| 6.02.02.10 | | 217 | method B | 1.38 |
| 6.02.02.11 | | 235 | method B | 1.35 |
| 6.02.02.12 | | 240 | method D | 0.97 |
| 6.02.02.13 | | 231 | method B | 1.54 |
| 6.02.02.14 | | 258 | method D | 0.95 |
| 6.02.02.15 | | 206 | method A | 0.93 |
| 6.02.02.16 | | 191 | method A | 0.87 |
| 6.02.02.17 | | 219 | method M | 0.93 |

-continued
| Examples | Product | MS m/z [M + H]+ | HPLC Method | Rt min |
|---|---|---|---|---|
| 6.02.02.18 | 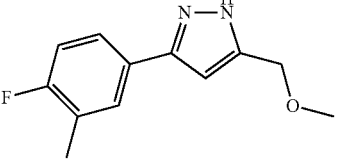 | 220 | method P | 1.10 |
| 6.02.02.19 | 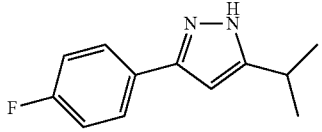 | 205 | method R | 1.26 |
| 6.02.02.20 | 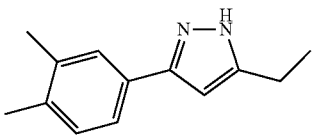 | 201 | method Q | 0.71 |
| 6.02.02.21 | 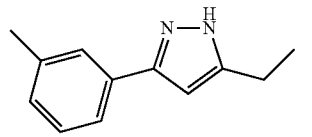 | 187 | method R | 1.20 |
| 6.02.02.22 | 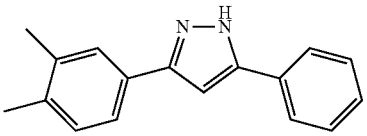 [SMILES: Cc1ccc(-c2cc(-c3ccccc3)[nH]n2)cc1C] | 249 | method M | 1.06 |
| 6.02.02.23 | 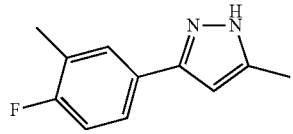 | 191 | method M | 0.78 |
| 6.02.02.24 | 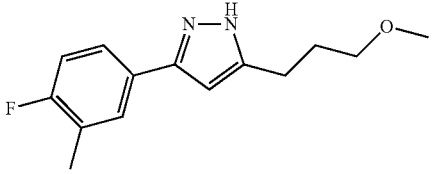 [SMILES: COCCCc1cc(-c2ccc(F)c(C)c2)n[nH]1] | 249 | method Q | 0.76 |
| 6.02.02.25 | 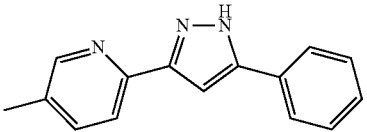 [SMILES: Cc1ccc(-c2cc(-c3ccccc3)[nH]n2)nc1] | 236 | method M | 0.68 |
| 6.02.02.26 | 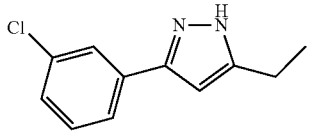 | 207 | method Q | 0.81 |

-continued

| Examples | Product | MS m/z [M + H]+ | HPLC Method | Rt min |
|---|---|---|---|---|
| 6.02.02.27 | | 233 | method T | 1.52 |
| 6.02.02.28 | | 250 | method M | 0.64 |
| 6.02.02.29 | | 201 | method Q | 0.78 |
| 6.02.02.30 | | 308 | method M | 0.69 |
| 6.02.02.31 | | 219 | method T | 1.45 |
| 6.02.02.32 | | 261 | method M | 0.96 |
| 6.02.02.33 | | 255 | method | |
| 6.02.02.34 | | 268 | method Z | 0.76 |
| 6.02.02.35 | | 354 | method AB | 1.35 |

-continued

| Examples | Product | MS m/z [M + H]+ | HPLC Method | Rt min |
| --- | --- | --- | --- | --- |
| 6.02.02.36 | | 354 | method | |
| 6.02.02.37 | | 246 | method | 1.41 |
| 6.02.02.38 | | 235 | method V | 0.85 |
| 6.02.02.39 | | 246 | method Y | 1.41 |
| 6.02.02.40 | | 220 | method AB | 0.78 |
| 6.02.02.41 | | 205 | method T | 0.86 |
| 6.02.02.42 | | 265 | method Y | 1.51 |

| Examples | Product | MS m/z [M + H]+ | HPLC Method | Rt min |
|---|---|---|---|---|
| 6.02.02.43 | | 288 | method AB | 0.85 |

6.02.03.01 3-(4-fluoro-3-methyl-phenyl)-5-phenyl-pyrazol-1-yl-acetic acid methyl ester

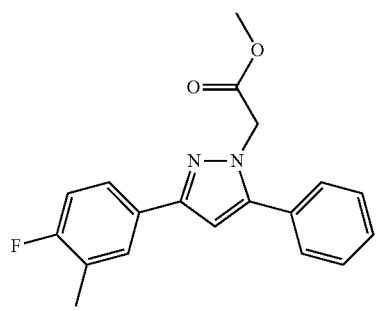 [SMILES: COC(=O)Cn1nc(-c2ccc(F)c(C)c2)cc1-c1ccccc1]

1.7 g 3-(4-fluoro-3-methyl-phenyl)-5-phenyl-pyrazole, 4 g $K_2CO_3$ and 0.64 mL 2-bromoacetic acid methyl ester were dissolved in 100 mL acetone and stirred for 10 h under reflux. $K_2CO_3$ was filtered and the solvent was removed to yield 1.9 g as a mixture of isomers.

By using the same synthesis strategy as for 1-(4-fluoro-3-methyl-phenyl)-3-phenyl-1,3-propanedione the following compounds were obtained:

| Examples | Product | MS m/z [M + H]+ | HPLC Method | Rt min |
|---|---|---|---|---|
| 6.02.03.02 | | 325 | method M | 0.97 |
| 6.02.03.03 | | 329 | | |
| 6.02.03.04 | | 329 | method B | 1.52 |

-continued

| Examples | Product | MS m/z [M + H]+ | HPLC Method | Rt min |
|---|---|---|---|---|
| 6.02.03.05 | | 329 | method B | 1.36 |
| 6.02.03.06 | | 291 | method B | 1.47 |
| 6.02.03.07 | | 331 | method E | 1.62 |
| 6.02.03.08 | | 289 | method B | 1.41 |
| 6.02.03.09 | | 307 | method G | 1.39 |

-continued
| Examples | Product | MS m/z [M + H]+ | HPLC Method | Rt min |
|---|---|---|---|---|
| 6.02.03.10 | 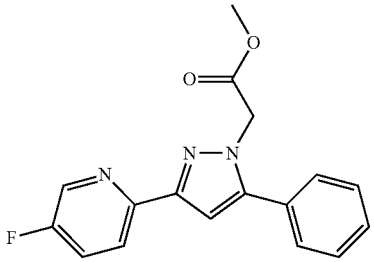 [SMILES: COC(=O)Cn1nc(-c2ccc(F)cn2)cc1-c1ccccc1] | 312 | method A | 0.92 |
| 6.02.03.11 | 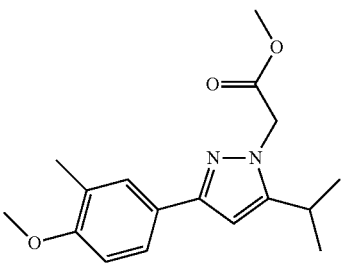 [SMILES: COC(=O)Cn1nc(-c2ccc(OC)c(C)c2)cc1C(C)C] | 303 | method B | 1.54 |
| 6.02.03.12 | 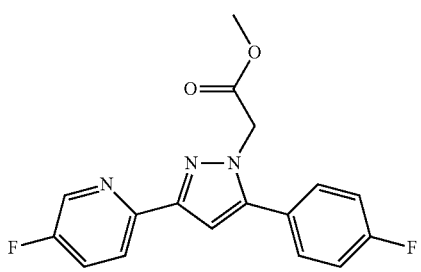 [SMILES: COC(=O)Cn1nc(-c2ccc(F)cn2)cc1-c1ccc(F)cc1] | 330 | method M | 1.01 |
| 6.02.03.13 | 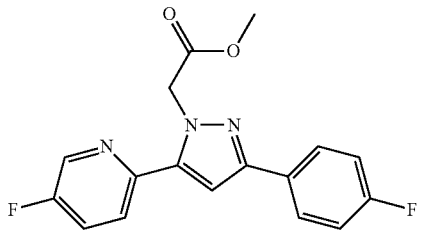 [SMILES: COC(=O)Cn1nc(-c2ccc(F)cc2)cc1-c1ccc(F)cn1] | 330 | | |
| 6.02.03.14 | 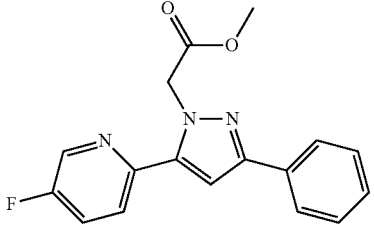 [SMILES: COC(=O)Cn1nc(-c2ccccc2)cc1-c1ccc(F)cn1] | 330 | method A | 0.96 |

-continued

| Examples | Product | MS m/z [M + H]+ | HPLC Method | Rt min |
|---|---|---|---|---|
| 6.02.03.15 | | 277 | method G | 1.40 |
| 6.02.03.16 | | 263 | method A | 0.92 |
| 6.02.03.17 | | 291 | method M | 0.97 |
| 6.02.03.18 | | 293 | method P | 1.20 |
| 6.02.03.19 | | 277 | method R | 1.33 |

-continued

| Examples | Product | MS m/z [M + H]+ | HPLC Method | Rt min |
|---|---|---|---|---|
| 6.02.03.20 | | 273 | method R | 1.42 |
| 6.02.03.21 | | 259 | method Q | 0.81 |
| 6.02.03.22 | | 321 | method M | 1.07 |
| 6.02.03.23 | | 263 | method S | 1.20 |
| 6.02.03.24 | | 321 | method Q | 0.80 |

-continued

| Examples | Product | MS m/z [M + H]+ | HPLC Method | Rt min |
|---|---|---|---|---|
| 6.02.03.25 | | 308 | method M | 0.66 |
| 6.02.03.26 | | 279 | method Q | 1.44 |
| 6.02.03.27 | | 305 | method T | 1.56 |
| 6.02.03.28 | | 322 | method M | 0.95 |
| 6.02.03.29 | | 322 | method M | 0.64 |
| 6.02.03.30 | | 273 | method T | 1.50 |

-continued

| Examples | Product | MS m/z [M + H]+ | HPLC Method | Rt min |
|---|---|---|---|---|
| 6.02.03.31 | | 322 | method M | 0.93 |
| 6.02.03.32 | | 322 | method M | 0.71 |
| 6.02.03.33 | | 291 | method T | 1.53 |
| 6.02.03.34 | | 333 | method M | 0.97 |
| 6.02.03.35 | | 327 | method AB | 1.54 |

-continued
| Examples | Product | MS m/z [M + H]+ | HPLC Method | Rt min |
|---|---|---|---|---|
| 6.02.03.36 | 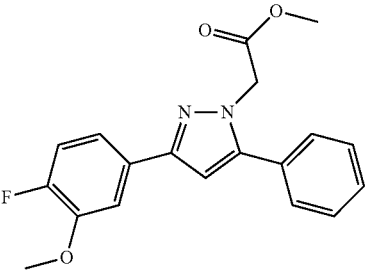 [SMILES: COC(=O)Cn1nc(-c2ccc(F)c(OC)c2)cc1-c1ccccc1] | 341 | method AA | 0.79 |
| 6.02.03.37 | 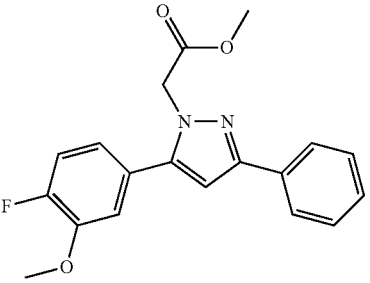 [SMILES: COC(=O)Cn1nc(-c2ccccc2)cc1-c1ccc(F)c(OC)c1] | 341 | method AA | 0.79 |
| 6.02.03.38 | 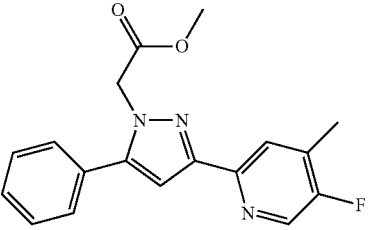 [SMILES: COC(=O)Cn1nc(-c2cc(C)c(F)cn2)cc1-c1ccccc1] | 326 | method AB | 1.34 |
| 6.02.03.39 | 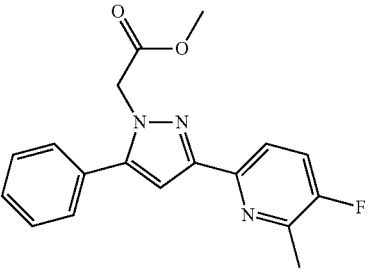 [SMILES: COC(=O)Cn1nc(-c2ccc(F)c(C)n2)cc1-c1ccccc1] | 326 | method AB | 1.38 |
| 6.02.03.40 | 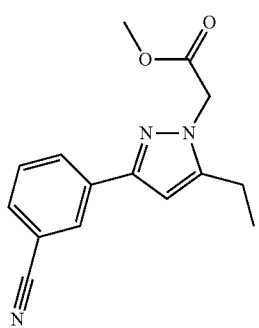 [SMILES: CCc1cc(-c2cccc(C#N)c2)nn1CC(=O)OC] | 270 | method AD | 1.26 |

-continued

| Examples | Product | MS m/z [M + H]+ | HPLC Method | Rt min |
|---|---|---|---|---|
| 6.02.03.41 | | 307 | method AB | 1.53 |
| 6.02.03.42 | | 307 | method AB | 1.53 |
| 6.02.03.43 | | 318 | method Y | 1.39 |
| 6.02.03.44 | | 318 | method Y | 1.37 |
| 6.02.03.45 | | 277 | method AD | 0.90 |

| Examples | Product | MS m/z [M + H]+ | HPLC Method | Rt min |
|---|---|---|---|---|
| 6.02.03.46 | | 292 | method AB | 0.82 |
| 6.02.03.47 | | 360 | method AB | 0.86 |
| 6.02.03.48 | | 337 | method AB | 1.51 |

Isomere Separation of 6.02.03.41 and 6.02.03.42
column: Daicel ADH-Saule (250×20 mm)
eluent: 25% EtOH+0.2% DEA: 75% $CO_2$: flow: 65 ml/min
dissolved in: MeOH:chloroform 9:1 (concentration: 70 mg/ml)
wave length: 210 nm 6.02.04.01 3-(4-fluoro-3-methyl-phenyl)-5-phenyl-pyrazol-1-yl acetic acid

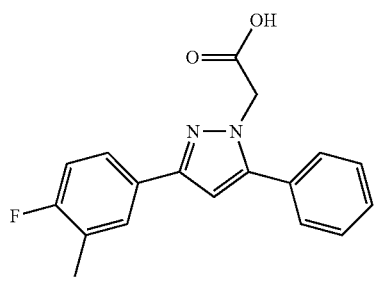 [SMILES: Cc1cc(-c2cc(-c3ccccc3)n(CC(=O)O)n2)ccc1F]

1.9 g of 3-(4-fluoro-3-methyl-phenyl)-5-phenyl-pyrazol-1-yl-acetic acid methyl ester was dissolved in 20 mL dioxane and a solution of 153 mg LiOH in 3 mL of water was added. The mixture was stirred for 6 h at 89° C. The solvent was removed and the residue dissolved in a mixture of methanol and water, purified by HPLC (method 1) and subsequently separated into the two isomers by HPLC (method 2). Yield: 222 mg and 374 mg of the two isomers.

$R_t$: 1.05 min (method D)

(M+H)+: 311

By using the same synthesis strategy as for 3-(4-fluoro-3-methyl-phenyl)-5-phenyl-pyrazol-1-yl acetic acid the following compounds were obtained:

| Examples | Product | MS m/z [M + H]+ | HPLC Method | Rt min |
| --- | --- | --- | --- | --- |
| 6.02.04.02 | | 311 | method D | 1.05 |
| 6.02.04.03 | | 315 | method K | 1.49 |
| 6.02.04.04 | | 275 | method B | 1.30 |
| 6.02.04.05 | | 317 | method B | 1.58 |
| 6.02.04.06 | | 275 | method B | 1.05 |
| 6.02.04.07 | | 289 | method K | 1.89 |

-continued

| Examples | Product | MS m/z [M + H]+ | HPLC Method | Rt min |
|---|---|---|---|---|
| 6.02.04.08 | 3-(4-fluoro-3-methylphenyl)-5-propyl-pyrazol-1-yl acetic acid | 277 | method M | 0.90 |
| 6.02.04.09 | 3,5-bis(4-fluorophenyl)-pyrazol-1-yl acetic acid | 315 | method E | 1.43 |
| 6.02.04.10 | 3-(4-fluorophenyl)-5-isopropyl-pyrazol-1-yl acetic acid | 277 | method B | 1.45 |
| 6.02.04.11 | 3-(4-fluoro-3-methoxyphenyl)-5-isopropyl-pyrazol-1-yl acetic acid | 293 | method K | 1.04 |
| 6.02.04.12 | 3-(5-fluoropyridin-2-yl)-5-phenyl-pyrazol-1-yl acetic acid | 298 | method D | 0.90 |
| 6.02.04.13 | 3-(5-fluoropyridin-2-yl)-5-(4-fluorophenyl)-pyrazol-1-yl acetic acid | 316 | method E | 1.33 |

-continued
| Examples | Product | MS m/z [M + H]+ | HPLC Method | Rt min |
|---|---|---|---|---|
| 6.02.04.14 | 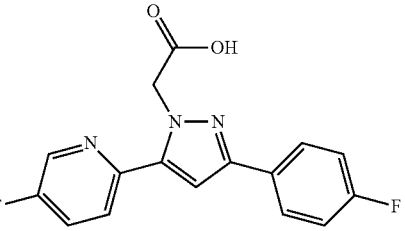 | 316 | method D | 0.93 |
| 6.02.04.15 | 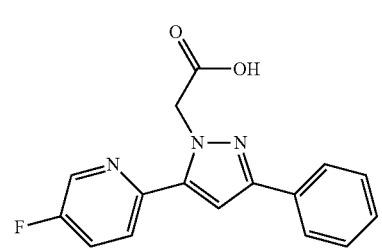 [SMILES: O=C(O)Cn1nc(-c2ccccc2)cc1-c1ccc(F)cn1] | 298 | method E | 1.37 |
| 6.02.04.16 | 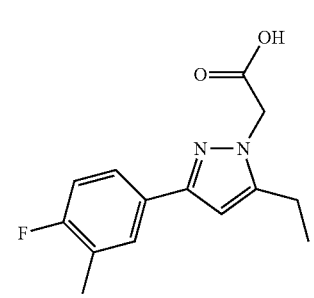 [SMILES: CCc1cc(-c2ccc(F)c(C)c2)nn1CC(=O)O] | 263 | method A | 0.93 |
| 6.02.04.17 | 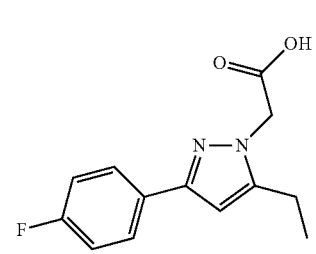 [SMILES: CCc1cc(-c2ccc(F)cc2)nn1CC(=O)O] | 249 | method A | 0.87 |
| 6.02.04.18 | 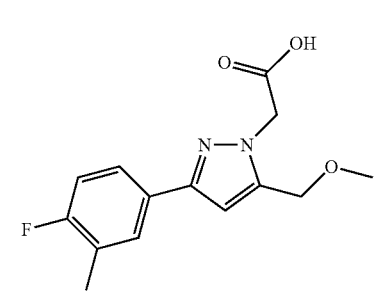 [SMILES: COCc1cc(-c2ccc(F)c(C)c2)nn1CC(=O)O] | 279 | method O | 1.40 |
| 6.02.04.19 | 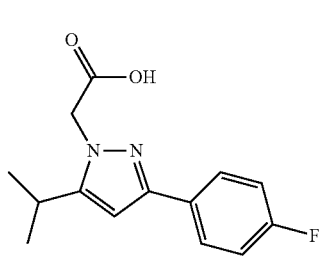 [SMILES: CC(C)c1cc(-c2ccc(F)cc2)nn1CC(=O)O] | 263 | method Q | 0.78 |

-continued
| Examples | Product | MS m/z [M + H]+ | HPLC Method | Rt min |
|---|---|---|---|---|
| 6.02.04.20 | 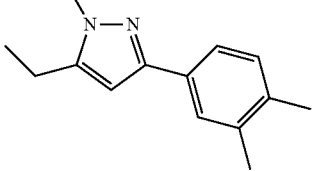 | 259 | method R | 1.32 |
| 6.02.04.21 | 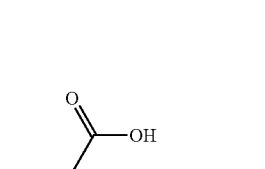 | 245 | method R | 1.25 |
| 6.02.04.22 | 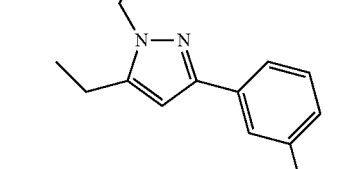 | 307 | method M | 0.97 |
| 6.02.04.23 | 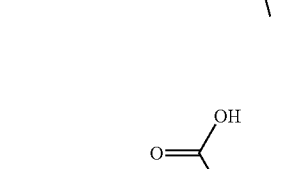 | 249 | method S | 1.20 |
| 6.02.04.24 | 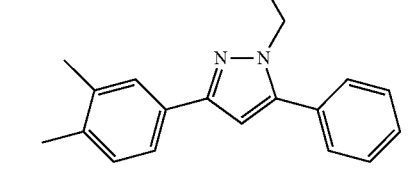 | 307 | method Q | 0.75 |

-continued

| Examples | Product | MS m/z [M + H]+ | HPLC Method | Rt min |
|---|---|---|---|---|
| 6.02.04.25 | (3-(5-methylpyridin-2-yl)-5-phenyl-pyrazol-1-yl)acetic acid | 294 | method M | 0.65 |
| 6.02.04.26 | (3-(3-chlorophenyl)-5-ethyl-pyrazol-1-yl)acetic acid | 265 | method T | 1.38 |
| 6.02.04.27 | (3-(4-fluoro-3-methylphenyl)-5-isobutyl-pyrazol-1-yl)acetic acid | 291 | method Q | 0.85 |
| 6.02.04.28 | (3-(5,6-dimethylpyridin-2-yl)-5-phenyl-pyrazol-1-yl)acetic acid | 308 | method M | 0.65 |
| 6.02.04.29 | (5-(5,6-dimethylpyridin-2-yl)-3-phenyl-pyrazol-1-yl)acetic acid | 308 | method K | 0.88 |
| 6.02.04.30 | (5-ethyl-3-(3-ethylphenyl)-pyrazol-1-yl)acetic acid | 259 | method T | 1.41 |

| Examples | Product | MS m/z [M + H]+ | HPLC Method | Rt min |
|---|---|---|---|---|
| 6.02.04.31 | (3-phenyl-5-(4,5-dimethylpyridin-2-yl)pyrazol-1-yl)acetic acid | 308 | method V | 1.32 |
| 6.02.04.32 | (5-phenyl-3-(4,5-dimethylpyridin-2-yl)pyrazol-1-yl)acetic acid | 308 | method V | 0.91 |
| 6.02.04.33 | (5-ethyl-3-(4-fluoro-3,5-dimethylphenyl)pyrazol-1-yl)acetic acid | 277 | method T | 1.45 |
| 6.02.04.34 | (3-phenyl-5-(4-chlorothiophen-2-yl)pyrazol-1-yl)acetic acid | 319 | method M | 0.92 |
| 6.02.04.35 | (5-phenyl-3-(3-chlorophenyl)pyrazol-1-yl)acetic acid | 313 | method AC | 1.49 |

-continued
| Examples | Product | MS m/z [M + H]+ | HPLC Method | Rt min |
|---|---|---|---|---|
| 6.02.04.36 | 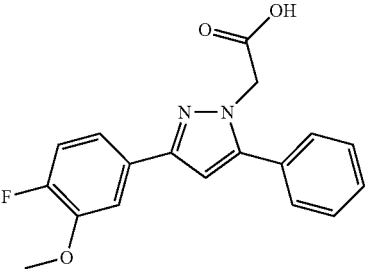 [SMILES: COc1cc(-c2cc(-c3ccccc3)n(CC(=O)O)n2)ccc1F] | 327 | method M | 0.87 |
| 6.02.04.37 | 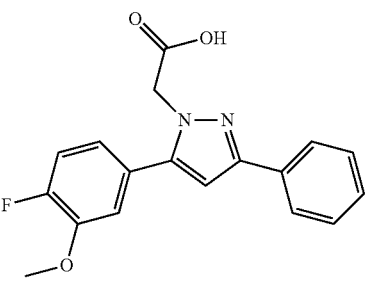 [SMILES: COc1cc(-c2cc(-c3ccccc3)nn2CC(=O)O)ccc1F] | 327 | method M | 0.88 |
| 6.02.04.38 | 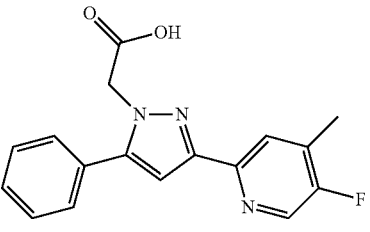 [SMILES: Cc1cc(-c2cc(-c3ccccc3)n(CC(=O)O)n2)ncc1F] | 312 | method AB | 1.26 |
| 6.02.04.39 | 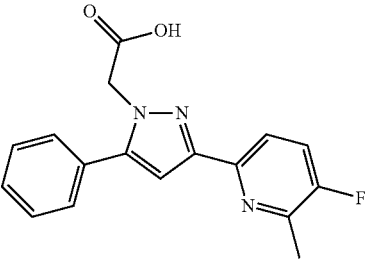 [SMILES: Cc1nc(-c2cc(-c3ccccc3)n(CC(=O)O)n2)ccc1F] | 312 | method AB | 1.30 |
| 6.02.04.40 | 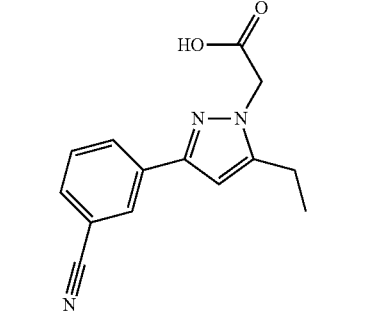 [SMILES: CCc1cc(-c2cccc(C#N)c2)nn1CC(=O)O] | 256 | method Y | 0.88 |

-continued
| Examples | Product | MS m/z [M + H]+ | HPLC Method | Rt min |
|---|---|---|---|---|
| 6.02.04.41 | 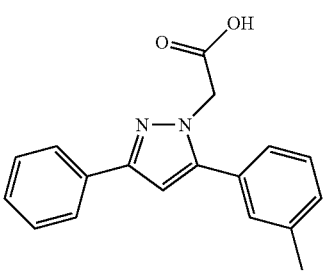 [SMILES: Cc1cccc(-c2cc(-c3ccccc3)nn2CC(=O)O)c1] | 293 | method Q | 0.93 |
| 6.02.04.42 | 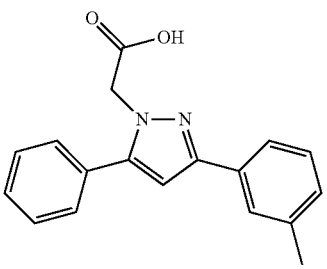 [SMILES: Cc1cccc(-c2cc(-c3ccccc3)n(CC(=O)O)n2)c1] | 293 | method Q | 0.97 |
| 6.02.04.43 | 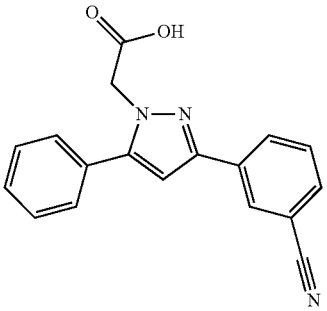 [SMILES: N#Cc1cccc(-c2cc(-c3ccccc3)n(CC(=O)O)n2)c1] | 304 | method Y | 1.02 |
| 6.02.04.44 | 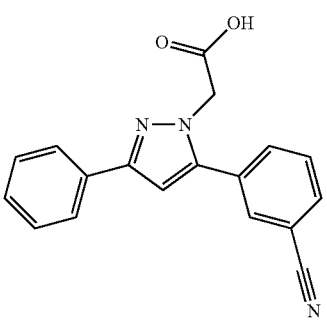 [SMILES: N#Cc1cccc(-c2cc(-c3ccccc3)nn2CC(=O)O)c1] | 304 | method M | 0.84 |
| 6.02.04.45 | 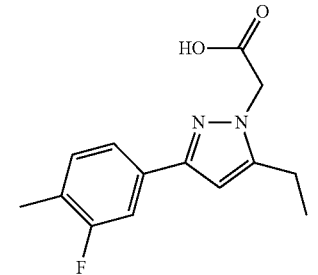 [SMILES: CCc1cc(-c2ccc(C)c(F)c2)nn1CC(=O)O] | 263 | method Y | 0.86 |

-continued

| Examples | Product | MS m/z [M + H]+ | HPLC Method | Rt min |
|---|---|---|---|---|
| 6.02.04.46 | | 278 | method AB | 0.76 |
| 6.02.04.47 | | 346 | method AB | 0.81 |
| 6.02.04.48 | | 323 | method M | 1.46 |

6.02.04.45 (3,5-Bis-(4-methoxy-phenyl)-pyrazol-1-yl)-acetic acid

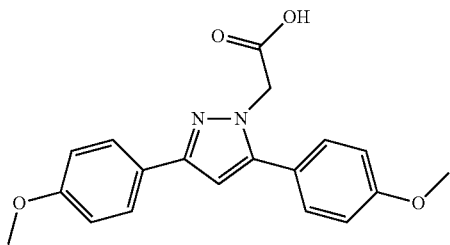

7 mL concentrated accetic acid was added to 500 mg 1,3-bis-(4-methoxy-phenyl)-propane-1,3-dione and 299 mg hydrazino-acetic acid ethyl ester hydrochloride, stirred for 24 h at RT and additional 24 h at 80° C. The reaction was cooled and the precipitate was filtered, washed with diethylether and dried to give 418 mg of the desired compound.

R$_f$: 0.24 (flash chromatography: silica gel, DCM: MeOH: 19:1+ two drops of conc. acetic acid)

(M+H)+: 339.

6.02.05.01 (3,5-Bis-(4-methoxy-phenyl)-pyrazol-1-yl)-acetic acid

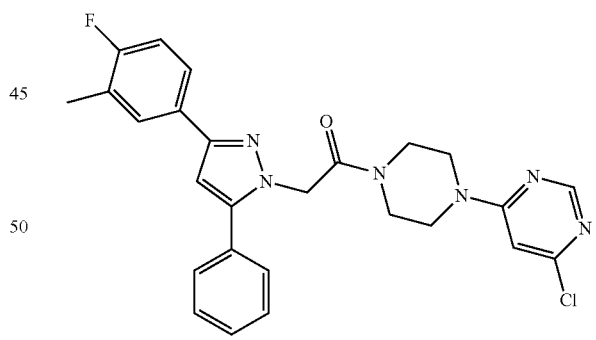

700 mg (3-(4-fluoro-3-methyl-phenyl)-5-phenyl-pyrazol-1-yl)-acetic acid was dissolved in 10 mL DMF. 869 mg TBTU and 465 µL DIPEA were added to this solution and the mixture was stirred 1 min at RT. 448 mg 4-chloro-6-piperazine-1-yl-pyrimidine was added and stirring was continued for 2 h. Then 10 mL of a 1M NaOH solution and 50 mL CH$_2$Cl$_2$ were added, the organic phase was separated. The solvent was removed. The residue was dissolved in dichlormethane, water was added and the layers were separated. The organic layer was evaporated and the residue was purified by flash chromatography (silica gel, DCM/MeOH 0-30 to yield 500 mg of the desired compound.

R$_t$: 1.58 (method F)
(M+H)$^+$: 491

7. Synthesis of Target Compounds

7.01.001. 2-(3-(4-Fluoro-3-methyl-phenyl)-5-phenyl-pyrazol-1-yl)-1-(4-(2-pyrimidinyl)-1-piperazinyl)-ethanon

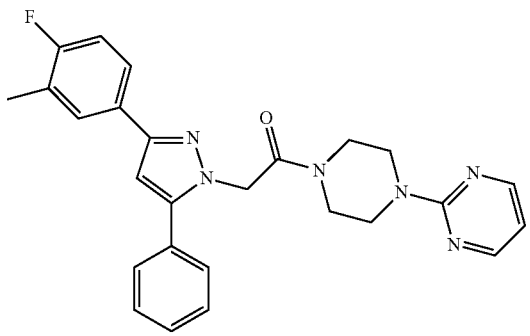 [SMILES: Cc1cc(-c2cc(-c3ccccc3)n(CC(=O)N3CCN(c4ncccn4)CC3)n2)ccc1F]

50 mg 3-(4-fluoro-3-methyl-phenyl)-5-phenyl-pyrazol-1-yl acetic acid was dissolved in 2 mL DMF. 83 mg PFTU and 33 µL DIPEA were added to this solution and the mixture was stirred for 15 min at RT. Then, 25 µL 2-(1-piperazinyl)-pyrimidine was added and stirring was continued for 8 h. Then, 1 mL of a K$_2$CO$_3$ solution (5%) and 10 mL CH$_2$Cl$_2$ were added, the organic phase was separated and washed two times with water. The solvent was removed and the residue was crystallized from ACN to yield 46 mg of the desired compound.

R$_t$: 1.04 min (method A)
(M+H)$^+$: 457

By using the same synthesis strategy as for 2-(3-(4-Fluoro-3-methyl-phenyl)-5-phenyl-pyrazol-1-yl)-1-(4-(2-pyrimidinyl)-1-piperazinyl)-ethanon the following compounds were obtained:

| Examples | Product | MS m/z [M + H]$^+$ | HPLC Method | Rt min |
|---|---|---|---|---|
| 7.01.002 | 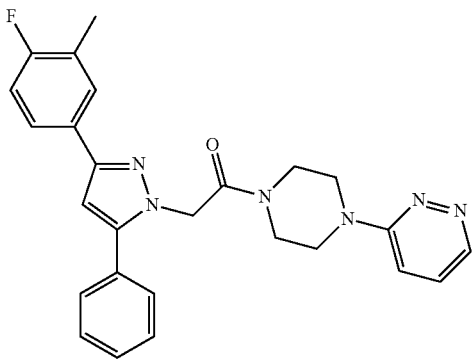 [SMILES: Cc1cc(-c2cc(-c3ccccc3)n(CC(=O)N3CCN(c4cccnn4)CC3)n2)ccc1F] | 457 | method A | 0.84 |
| 7.01.003 | 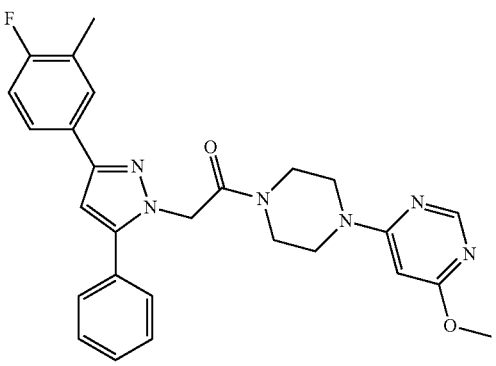 [SMILES: COc1cc(N2CCN(C(=O)Cn3nc(-c4ccc(F)c(C)c4)cc3-c3ccccc3)CC2)ncn1] | 486 | method A | 0.98 |

| Examples | Product | MS m/z [M + H]+ | HPLC Method | Rt min |
|---|---|---|---|---|
| 7.01.004 | | 456 | method A | 0.86 |
| 7.01.005 | | 457 | method A | 1.04 |
| 7.01.006 | | 456 | method A | 0.86 |
| 7.01.007 | | 474 | method L | 1.88 |

| Examples | Product | MS m/z [M + H]+ | HPLC Method | Rt min |
|---|---|---|---|---|
| 7.01.08 | 3,5-diphenyl-pyrazole-CH2-C(O)-piperazine-pyrimidin-4-yl | 425 | method L | 1.78 |
| 7.01.009 | 3,5-diphenyl-pyrazole-CH2-C(O)-piperazine-(5-chloropyridin-2-yl) | 458 | method L | 2.16 |
| 7.01.010 | 3,5-diphenyl-pyrazole-CH2-C(O)-piperazine-(2-cyanophenyl) | 448 | method L | 2.11 |
| 7.01.011 | 3,5-diphenyl-pyrazole-CH2-C(O)-piperazine-(2-ethoxyphenyl) | 467 | method L | 2.13 |

| Examples | Product | MS m/z [M + H]+ | HPLC Method | Rt min |
|---|---|---|---|---|
| 7.01.012 | 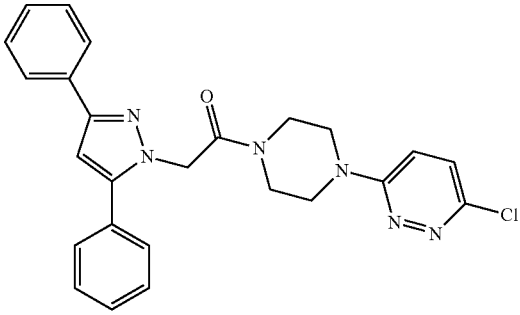 | 459 | method L | 2.07 |
| 7.01.013 | 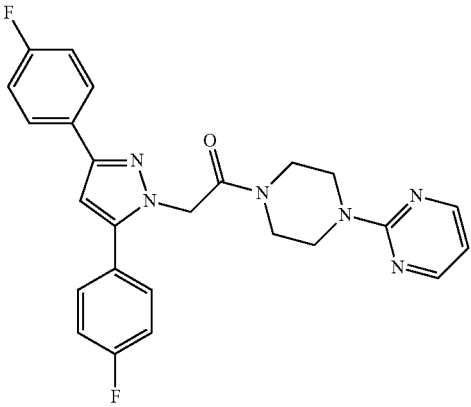 [SMILES: O=C(Cn1nc(-c2ccc(F)cc2)cc1-c1ccc(F)cc1)N1CCN(c2ncccn2)CC1] | 461 | method A | 0.99 |
| 7.01.014 | 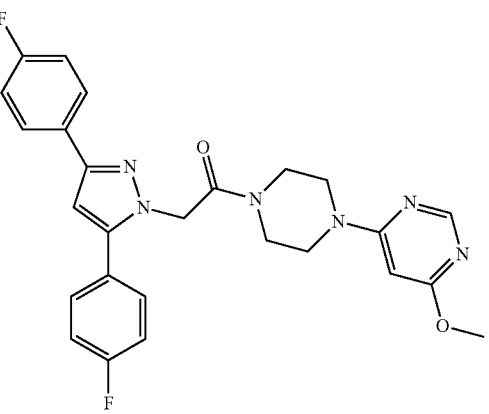 [SMILES: COc1cc(N2CCN(C(=O)Cn3nc(-c4ccc(F)cc4)cc3-c3ccc(F)cc3)CC2)ncn1] | 491 | method A | 0.93 |
| 7.01.015 | 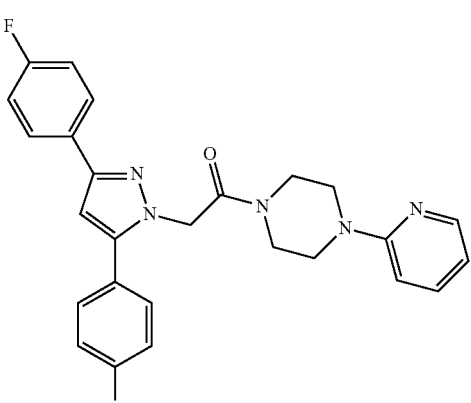 | 460 | method A | 0.82 |

| Examples | Product | MS m/z [M + H]+ | HPLC Method | Rt min |
|---|---|---|---|---|
| 7.01.016 | 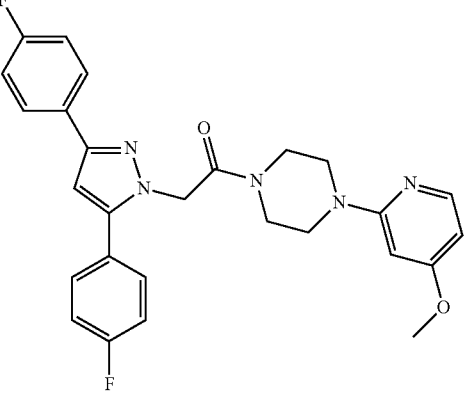 | 490 | method A | 0.81 |
| 7.01.017 | 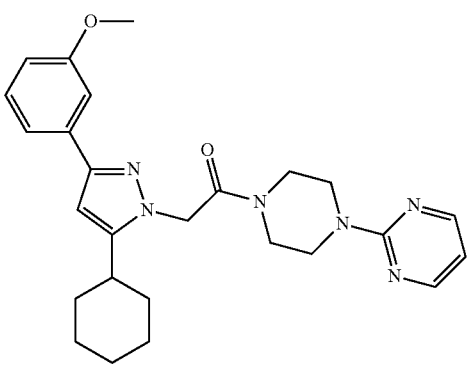 [SMILES: COc1cccc(-c2cc(C3CCCCC3)n(CC(=O)N3CCN(c4ncccn4)CC3)n2)c1] | 461 | method B | 1.52 |
| 7.01.018 | 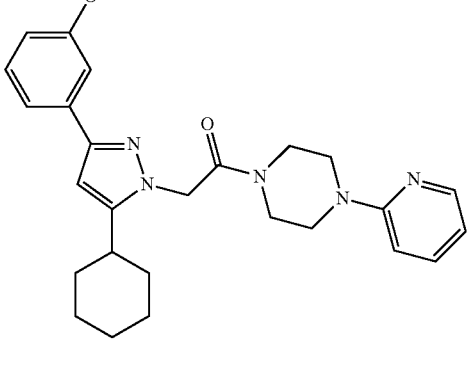 | 460 | method B | 1.36 |
| 7.01.019 | 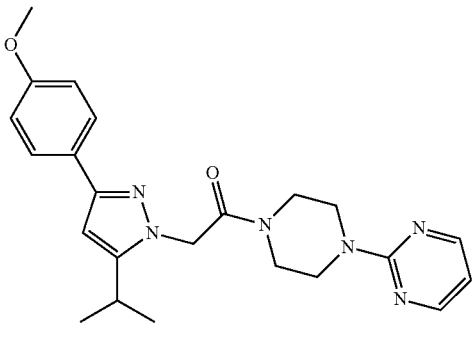 [SMILES: COc1ccc(-c2cc(C(C)C)n(CC(=O)N3CCN(c4ncccn4)CC3)n2)cc1] | 421 | method B | 1.37 |

-continued

| Examples | Product | MS m/z [M + H]+ | HPLC Method | Rt min |
|---|---|---|---|---|
| 7.01.020 | | 420 | method B | 1.19 |
| 7.01.021 | | 434 | method B | 1.21 |
| 7.01.022 | | 421 | method B | 1.20 |
| 7.01.023 | | 451 | method B | 1.28 |

| Examples | Product | MS m/z [M + H]+ | HPLC Method | Rt min |
|---|---|---|---|---|
| 7.01.024 | | 436 | Method B | 1.33 |
| 7.01.025 | | 452 | method B | 1.33 |
| 7.01.026 | | 421 | method B | 1.32 |
| 7.01.027 | | 453 | method B | 1.42 |
| 7.01.028 | | 453 | method B | 1.47 |

-continued

| Examples | Product | MS m/z [M + H]+ | HPLC Method | Rt min |
|---|---|---|---|---|
| 7.01.029 | | 423 | method B | 1.31 |
| 7.01.030 | | 453 | method G | 1.32 |
| 7.01.031 | | 441 | method H | 1.44 |
| 7.01.032 | | 453 | method I | 0.91 |
| 7.01.033 | | 476 | method B | 1.47 |

| Examples | Product | MS m/z [M + H]+ | HPLC Method | Rt min |
|---|---|---|---|---|
| 7.01.034 | 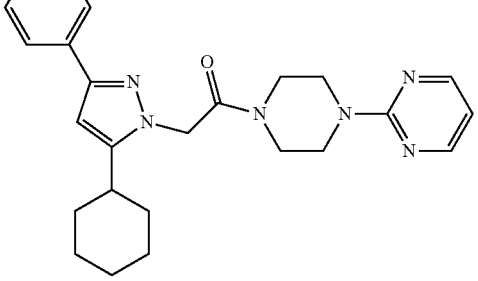 | 463 | method B | 1.61 |
| 7.01.035 | 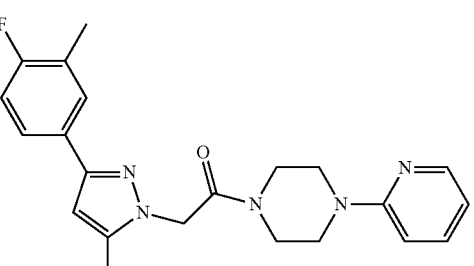 | 462 | method B | 1.43 |
| 7.01.036 | 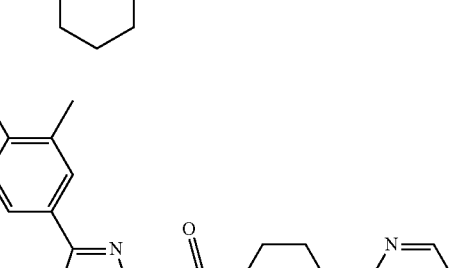 | 493 | method B | 1.54 |
| 7.01.037 | 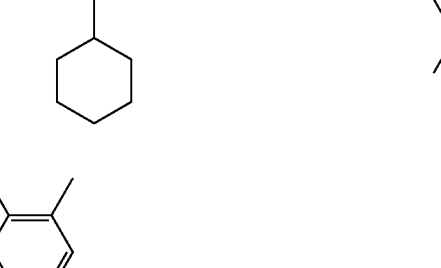 | 492 | method B | 1.45 |

| Examples | Product | MS m/z [M + H]+ | HPLC Method | Rt min |
|---|---|---|---|---|
| 7.01.038 | | 463 | method B | 1.46 |
| 7.01.039 | | 463 | method J | 0.56 |
| 7.01.040 | | 463 | method J | 0.54 |
| 7.01.041 | | 420 | method J | 0.49 |

-continued
| Examples | Product | MS m/z [M + H]+ | HPLC Method | Rt min |
|---|---|---|---|---|
| 7.01.042 | 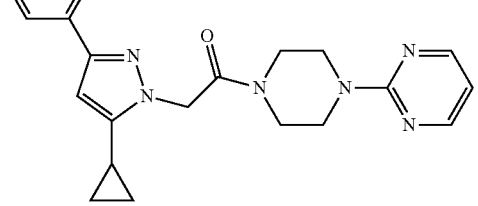 | 421 | method J | 0.56 |
| 7.01.043 | 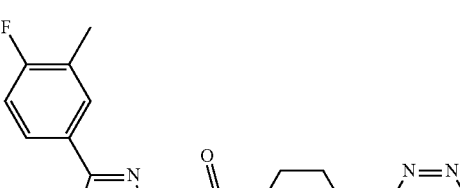 | 421 | method J | 0.50 |
| 7.01.044 | 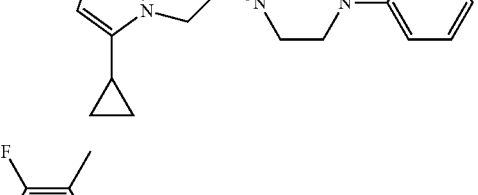 | 434 | method J | 0.50 |
| 7.01.045 | 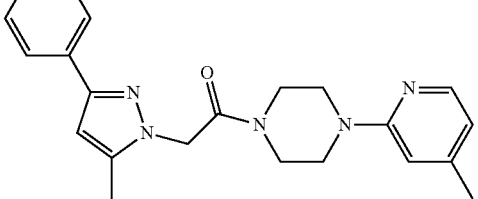 | 451 | method J | 0.50 |
| 7.01.046 |  | 450 | method J | 0.50 |

-continued

| Examples | Product | MS m/z [M + H]+ | HPLC Method | Rt min |
|---|---|---|---|---|
| 7.01.047 | | 469 | method G | 1.27 |
| 7.01.048 | | 452 | method K | 1.46 |
| 7.01.049 | | 438 | method K | 1.41 |
| 7.01.050 | | 517 | method K | 1.52 |
| 7.01.051 | | 439 | method K | 1.40 |

| Examples | Product | MS m/z [M + H]+ | HPLC Method | Rt min |
|---|---|---|---|---|
| 7.01.052 | | 448 | method B | 1.30 |
| 7.01.053 | | 465 | method B | 1.35 |
| 7.01.054 | | 435 | method B | 1.43 |
| 7.01.055 | | 464 | method B | 1.30 |

| Examples | Product | MS m/z [M + H]+ | HPLC Method | Rt min |
|---|---|---|---|---|
| 7.01.056 | | 434 | method B | 1.30 |
| 7.01.057 | | 444 | method D | 0.93 |
| 7.01.058 | | 442 | method D | 0.76 |
| 7.01.059 | | 461 | method D | 0.78 |

-continued

| Examples | Product | MS m/z [M + H]+ | HPLC Method | Rt min |
|---|---|---|---|---|
| 7.01.060 | | 444 | method A | 0.72 |
| 7.01.061 | | 474 | method A | 0.83 |
| 7.01.062 | | 462 | method D | 0.97 |
| 7.01.063 | | 492 | method A | 0.85 |

-continued

| Examples | Product | MS m/z [M + H]+ | HPLC Method | Rt min |
|---|---|---|---|---|
| 7.01.064 | | 462 | method A | 0.75 |
| 7.01.065 | | 462 | method A | 0.95 |
| 7.01.066 | | 443 | method A | 0.94 |

-continued

| Examples | Product | MS m/z [M + H]⁺ | HPLC Method | Rt min |
|---|---|---|---|---|
| 7.01.067 | | 439 | method A | 0.91 |
| 7.01.068 | | 438 | method A | 0.79 |
| 7.01.069 | | 408 | method A | 0.80 |
| 7.01.070 | | 409 | method A | 0.98 |
| 7.01.071 | | 439 | method A | 1.01 |

| Examples | Product | MS m/z [M + H]+ | HPLC Method | Rt min |
|---|---|---|---|---|
| 7.01.072 | | 427 | method I | 0.92 |
| 7.01.073 | | 394 | method A | 0.73 |
| 7.01.074 | | 395 | method A | 0.92 |
| 7.01.075 | | 424 | method A | 0.75 |
| 7.01.076 | | 425 | method A | 0.97 |

| Examples | Product | MS m/z [M + H]+ | HPLC Method | Rt min |
|---|---|---|---|---|
| 7.01.077 | | 425 | method A | 0.85 |
| 7.01.078 | | 413 | method A | 0.99 |
| 7.01.079 | | 453 | method M | 0.95 |
| 7.01.080 | | 452 | method M | 0.85 |

| Examples | Product | MS m/z [M + H]+ | HPLC Method | Rt min |
|---|---|---|---|---|
| 7.01.081 | 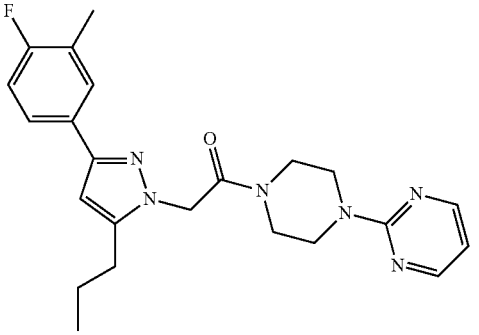 [SMILES: CCCc1cc(-c2ccc(F)c(C)c2)nn1CC(=O)N1CCN(c2ncccn2)CC1] | 423 | method M | 1.02 |
| 7.01.082 | 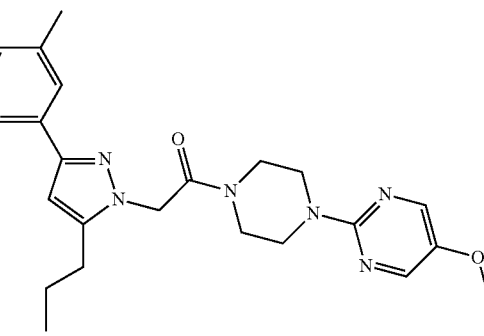 | 453 | method M | 1.04 |
| 7.01.083 | 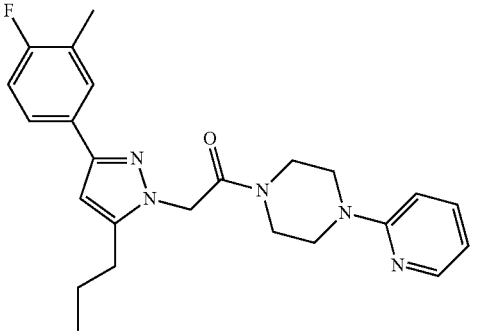 [SMILES: CCCc1cc(-c2ccc(F)c(C)c2)nn1CC(=O)N1CCN(c2ccccn2)CC1] | 422 | method M | 0.85 |
| 7.01.084 | 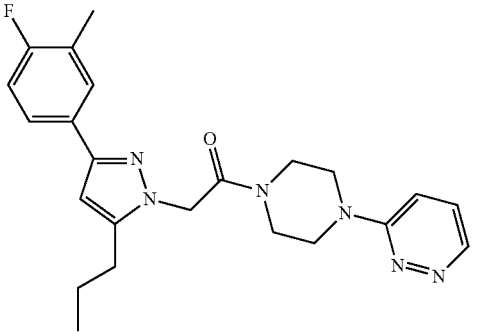 [SMILES: CCCc1cc(-c2ccc(F)c(C)c2)nn1CC(=O)N1CCN(c2cccnn2)CC1] | 423 | method M | 0.86 |

-continued

| Examples | Product | MS m/z [M + H]+ | HPLC Method | Rt min |
|---|---|---|---|---|
| 7.01.085 | | 438 | method Q | 0.72 |
| 7.01.087 | | 405 | method Q | 0.86 |
| 7.01.088 | | 439 | method Q | 0.77 |
| 7.01.089 | | 439 | method Q | 0.86 |

| Examples | Product | MS m/z [M + H]+ | HPLC Method | Rt min |
|---|---|---|---|---|
| 7.01.090 | 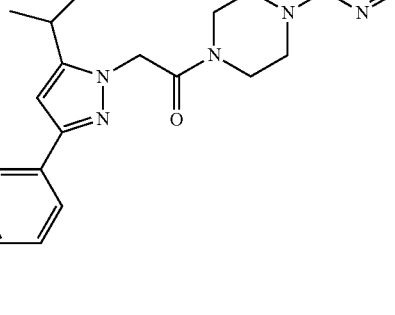 | 409 | method Q | 0.82 |
| 7.01.091 | 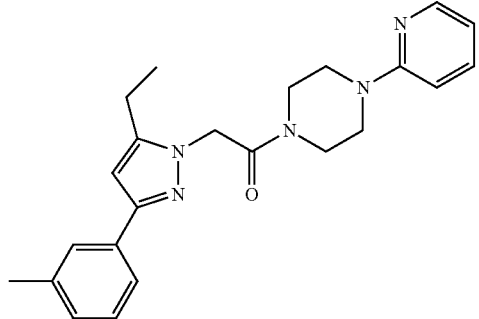 | 404 | method Q | 0.74 |
| 7.01.092 | 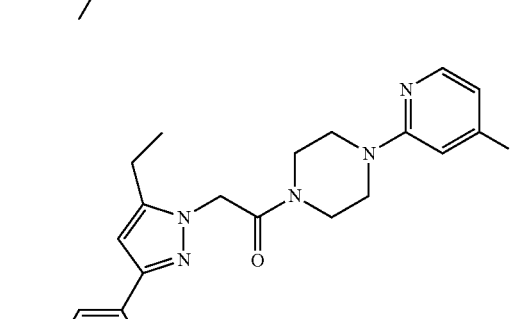 | 434 | method Q | 0.75 |
| 7.01.093 | 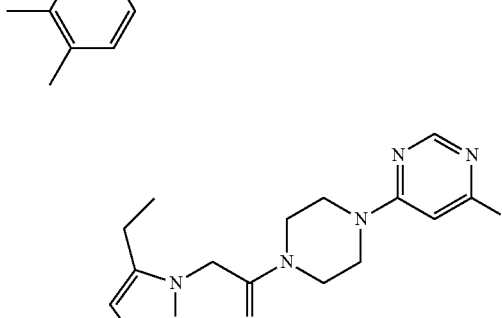 | 435 | method Q | 0.80 |

-continued
| Examples | Product | MS m/z [M + H]+ | HPLC Method | Rt min |
|---|---|---|---|---|
| 7.01.094 | 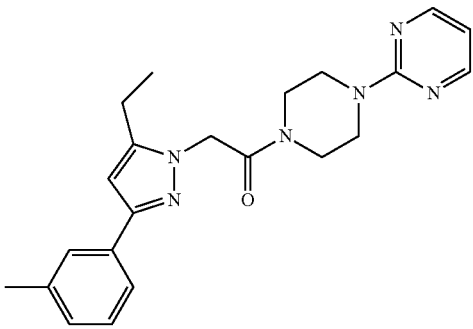 [SMILES: CCc1cc(-c2cccc(C)c2)nn1CC(=O)N1CCN(c2ncccn2)CC1] | 391 | method Q | 0.82 |
| 7.01.095 | 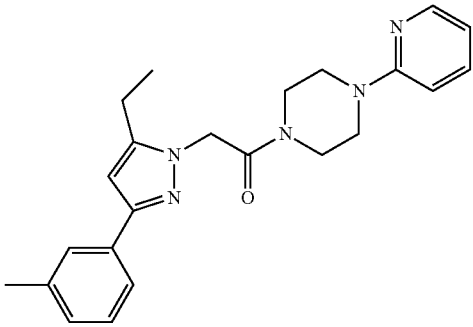 [SMILES: CCc1cc(-c2cccc(C)c2)nn1CC(=O)N1CCN(c2ccccn2)CC1] | 390 | method Q | 0.71 |
| 7.01.096 | 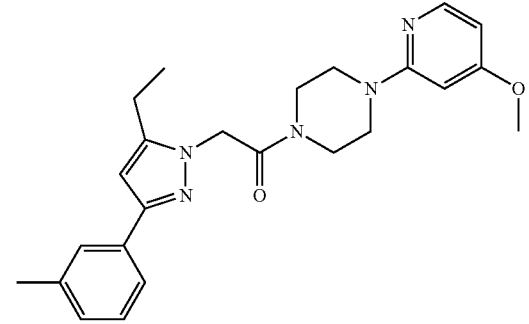 | 420 | method Q | 0.72 |
| 7.01.097 | 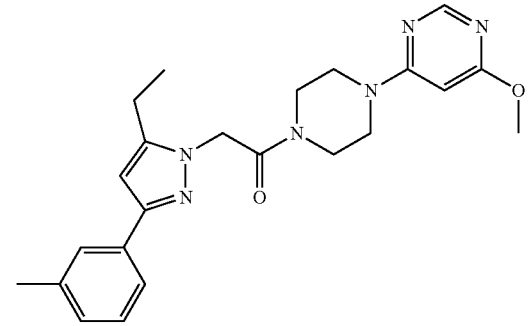 | 421 | method Q | 0.77 |

| Examples | Product | MS m/z [M + H]⁺ | HPLC Method | Rt min |
|---|---|---|---|---|
| 7.01.098 | | 453 | method M | 1.05 |
| 7.01.099 | | 435 | method Q | 0.88 |
| 7.01.100 | | 421 | method Q | 0.84 |
| 7.01.101 | | 483 | method M | 0.99 |

| Examples | Product | MS m/z [M + H]⁺ | HPLC Method | Rt min |
|---|---|---|---|---|
| 7.01.102 | | 452 | method M | 0.87 |
| 7.01.103 | | 483 | method M | 1.05 |
| 7.01.104 | | 395 | method P | 1.20 |
| 7.01.105 | | 483 | method M | 1.03 |

-continued

| Examples | Product | MS m/z [M + H]+ | HPLC Method | Rt min |
|---|---|---|---|---|
| 7.01.106 | | 439 | method M | 0.56 |
| 7.01.107 | | 453 | method Q | 0.80 |
| 7.01.108 | | 452 | method Q | 0.68 |
| 7.01.109 | | 482 | method Q | 0.69 |

| Examples | Product | MS m/z [M + H]+ | HPLC Method | Rt min |
|---|---|---|---|---|
| 7.01.110 | | 483 | method Q | 0.74 |
| 7.01.111 | | 440 | method M | 0.66 |
| 7.01.112 | | 483 | method Q | 0.83 |
| 7.01.113 | | 411 | method U | 0.81 |

| Examples | Product | MS m/z [M + H]+ | HPLC Method | Rt min |
|---|---|---|---|---|
| 7.01.114 | | 410 | method U | 0.68 |
| 7.01.115 | | 441 | method U | 0.84 |
| 7.01.116 | | 441 | method U | 0.75 |
| 7.01.117 | | 436 | method Q | 0.76 |

| Examples | Product | MS m/z [M + H]+ | HPLC Method | Rt min |
|---|---|---|---|---|
| 7.01.118 | | 437 | method Q | 0.89 |
| 7.01.119 | | 469 | method M | 0.61 |
| 7.01.120 | | 470 | method M | 0.69 |
| 7.01.121 | | 467 | method Q | 0.84 |

| Examples | Product | MS m/z [M + H]+ | HPLC Method | Rt min |
|---|---|---|---|---|
| 7.01.122 | 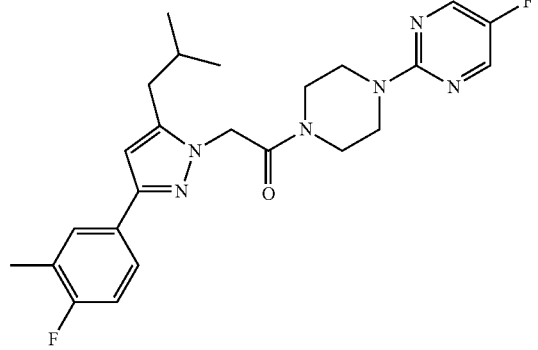 | 455 | method Q | 0.92 |
| 7.01.123 | 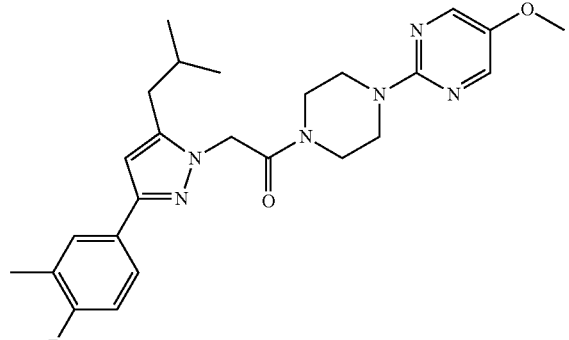 | 467 | method Q | 0.91 |
| 7.01.124 | 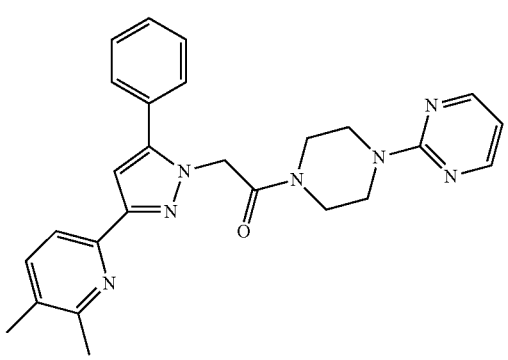 [SMILES: Cc1ccc(-c2cc(-c3ccccc3)n(CC(=O)N3CCN(c4ncccn4)CC3)n2)nc1C] | 454 | method M | 0.71 |
| 7.01.125 | 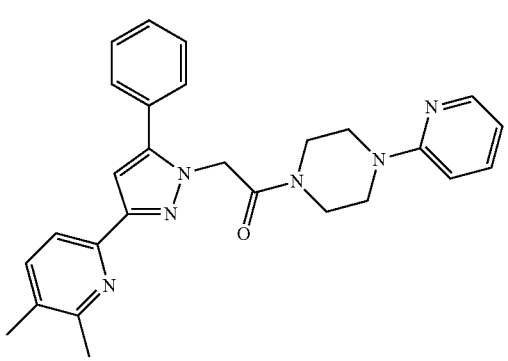 [SMILES: Cc1ccc(-c2cc(-c3ccccc3)n(CC(=O)N3CCN(c4ccccn4)CC3)n2)nc1C] | 454 | method M | 0.71 |

-continued

| Examples | Product | MS m/z [M + H]+ | HPLC Method | Rt min |
|---|---|---|---|---|
| 7.01.126 | | 454 | method M | 0.71 |
| 7.01.127 | | 454 | method M | 0.71 |
| 7.01.128 | | 404 | method Q | 0.69 |
| 7.01.129 | | 435 | method Q | 0.77 |

| Examples | Product | MS m/z [M + H]+ | HPLC Method | Rt min |
|---|---|---|---|---|
| 7.01.130 | 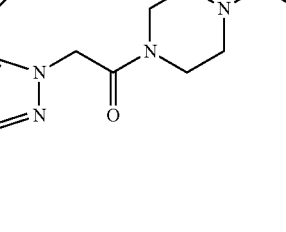 | 423 | method Q | 0.86 |
| 7.01.131 | 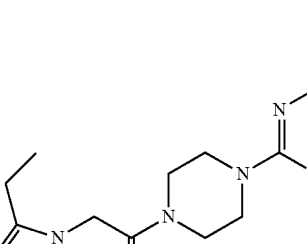 | 405 | method Q | 0.82 |
| 7.01.132 | 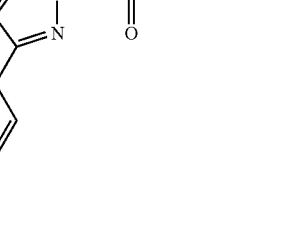 | 435 | method Q | 0.84 |
| 7.01.133 | 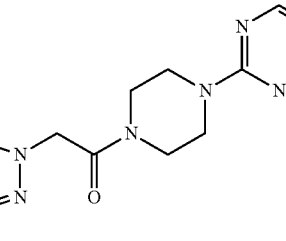 | 454 | method M | 0.92 |

-continued
| Examples | Product | MS m/z [M + H]+ | HPLC Method | Rt min |
|---|---|---|---|---|
| 7.01.134 | 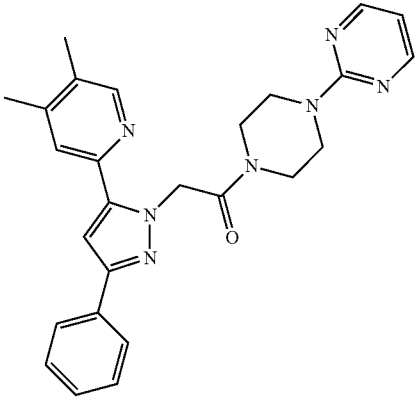 [SMILES: Cc1cnc(-c2cc(-c3ccccc3)nn2CC(=O)N2CCN(c3ncccn3)CC2)cc1C] | 454 | method M | 0.93 |
| 7.01.135 | 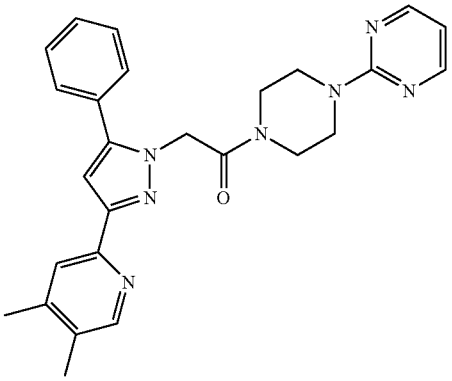 [SMILES: Cc1cnc(-c2cc(-c3ccccc3)n(CC(=O)N3CCN(c4ncccn4)CC3)n2)cc1C] | 454 | method M | 0.73 |
| 7.01.136 | 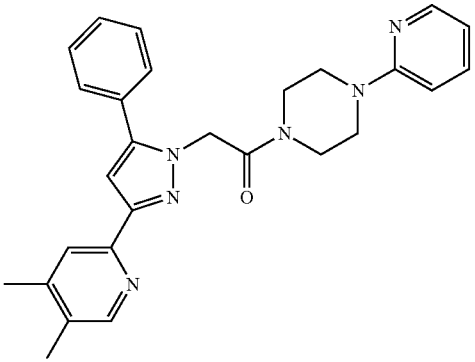 [SMILES: Cc1cnc(-c2cc(-c3ccccc3)n(CC(=O)N3CCN(c4ccccn4)CC3)n2)cc1C] | 453 | method M | 0.62 |
| 7.01.137 | 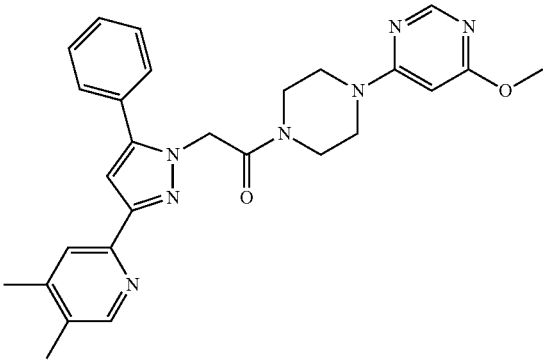 | 454 | method M | 0.92 |

-continued
| Examples | Product | MS m/z [M + H]+ | HPLC Method | Rt min |
|---|---|---|---|---|
| 7.01.138 | 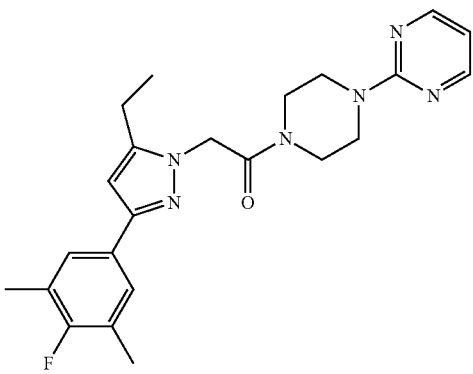 [SMILES: CCc1cc(-c2cc(C)c(F)c(C)c2)nn1CC(=O)N1CCN(c2ncccn2)CC1] | 423 | method Q | 0.83 |
| 7.01.139 | 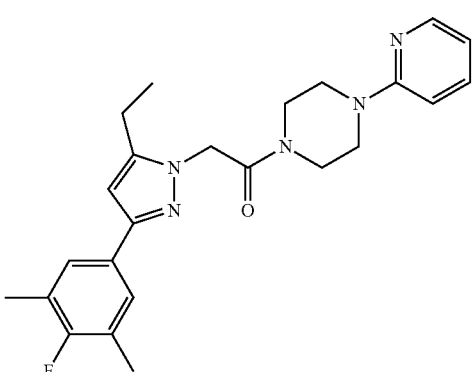 | 422 | method Q | 0.71 |
| 7.01.140 | 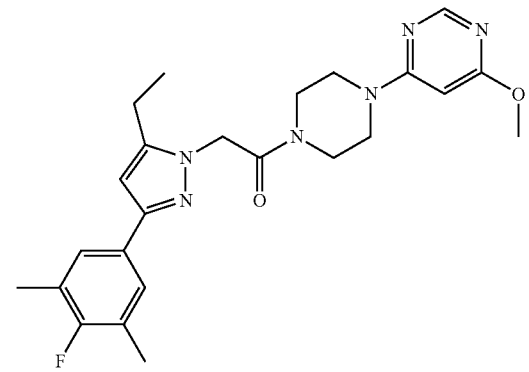 | 453 | method Q | 0.78 |
| 7.01.141 | 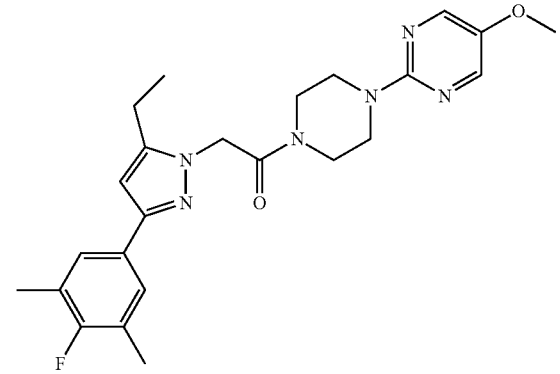 | 453 | method Q | 0.85 |

-continued
| Examples | Product | MS m/z [M + H]+ | HPLC Method | Rt min |
|---|---|---|---|---|
| 7.01.142 | 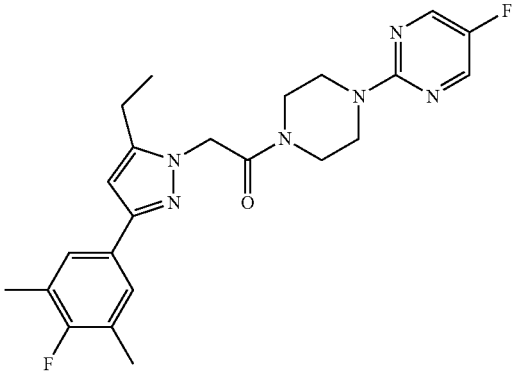 [SMILES: CCc1cc(-c2cc(C)c(F)c(C)c2)nn1CC(=O)N1CCN(c2ncc(F)cn2)CC1] | 441 | method Q | 0.86 |
| 7.01.143 | 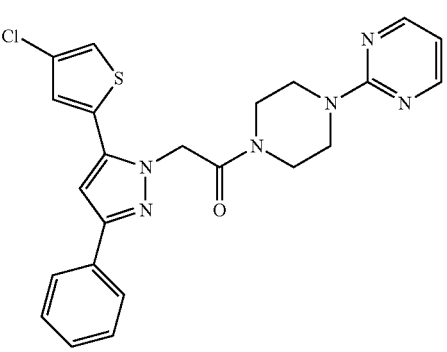 [SMILES: O=C(Cn1nc(-c2ccccc2)cc1-c1cc(Cl)cs1)N1CCN(c2ncccn2)CC1] | 465 | method M | 0.94 |
| 7.01.144 | 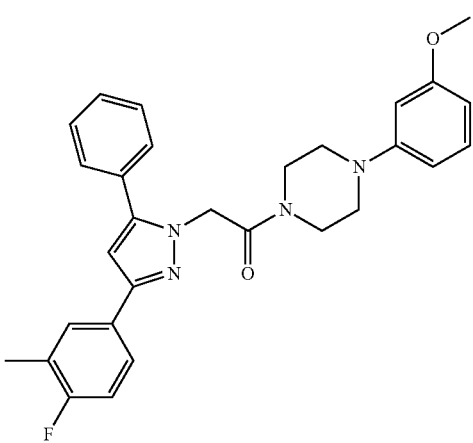 | 485 | method Y | 1.56 |
| 7.01.145 | 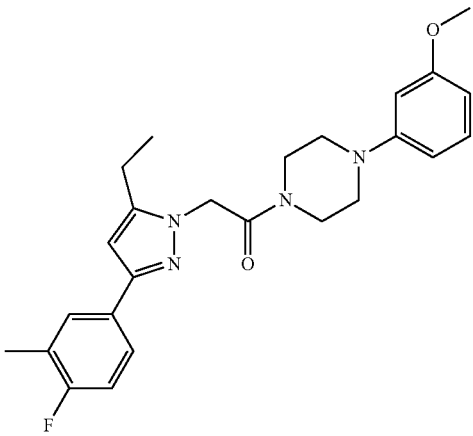 | 437 | method Y | 1.51 |

| Examples | Product | MS m/z [M + H]+ | HPLC Method | Rt min |
|---|---|---|---|---|
| 7.01.146 | 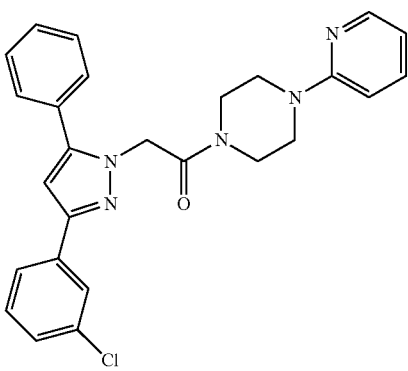 [SMILES: O=C(Cn1nc(-c2cccc(Cl)c2)cc1-c1ccccc1)N1CCN(c2ccccn2)CC1] | 437 | method U | 0.70 |
| 7.01.147 | 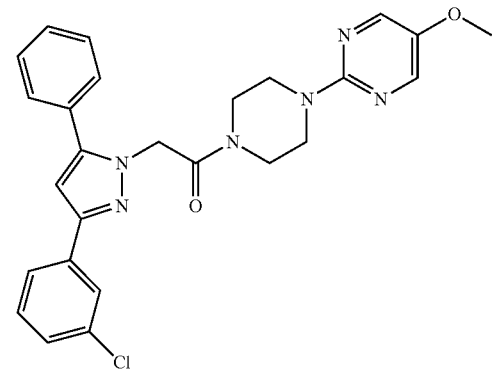 [SMILES: COc1cnc(N2CCN(C(=O)Cn3nc(-c4cccc(Cl)c4)cc3-c3ccccc3)CC2)nc1] | 489 | method U | 0.89 |
| 7.01.148 | 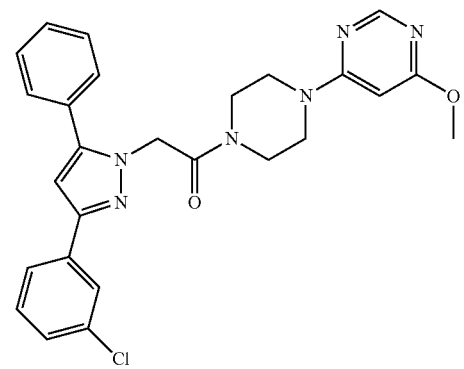 [SMILES: COc1cc(N2CCN(C(=O)Cn3nc(-c4cccc(Cl)c4)cc3-c3ccccc3)CC2)ncn1] | 489 | method U | 0.78 |
| 7.01.149 | 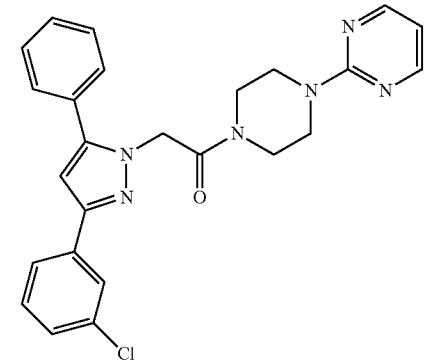 [SMILES: O=C(Cn1nc(-c2cccc(Cl)c2)cc1-c1ccccc1)N1CCN(c2ncccn2)CC1] | 459 | method U | 0.83 |

-continued

| Examples | Product | MS m/z [M + H]+ | HPLC Method | Rt min |
|---|---|---|---|---|
| 7.01.150 | | 473 | method M | 0.91 |
| 7.01.151 | | 472 | method M | 0.75 |
| 7.01.152 | | 503 | method M | 0.84 |
| 7.01.153 | | 473 | method M | 0.91 |

| Examples | Product | MS m/z [M + H]+ | HPLC Method | Rt min |
|---|---|---|---|---|
| 7.01.154 | 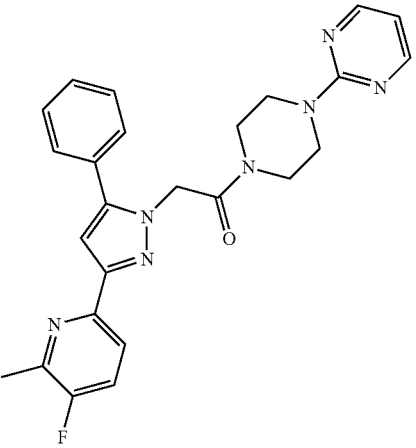 [SMILES: Cc1nc(-c2cc(-c3ccccc3)n(CC(=O)N3CCN(c4ncccn4)CC3)n2)ccc1F] | 458 | method Q | 0.72 |
| 7.01.155 | 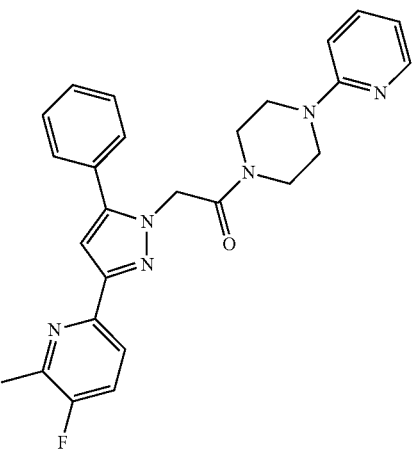 [SMILES: Cc1nc(-c2cc(-c3ccccc3)n(CC(=O)N3CCN(c4ccccn4)CC3)n2)ccc1F] | 457 | method Q | 0.60 |
| 7.01.156 | 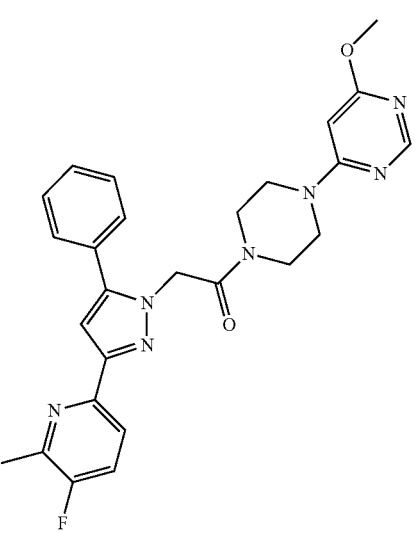 [SMILES: COc1cc(N2CCN(C(=O)Cn3nc(-c4ccc(F)c(C)n4)cc3-c3ccccc3)CC2)ncn1] | 488 | method Q | 0.67 |

-continued
| Examples | Product | MS m/z [M + H]+ | HPLC Method | Rt min |
|---|---|---|---|---|
| 7.01.157 | 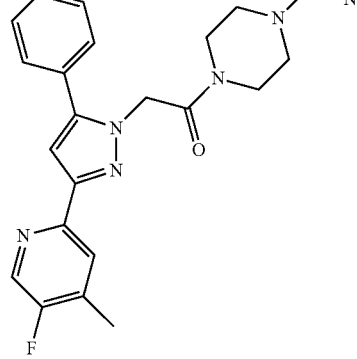 | 458 | method Q | 0.70 |
| 7.01.158 | 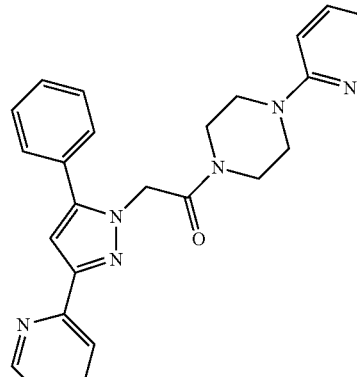 | 457 | method Q | 0.58 |
| 7.01.159 | 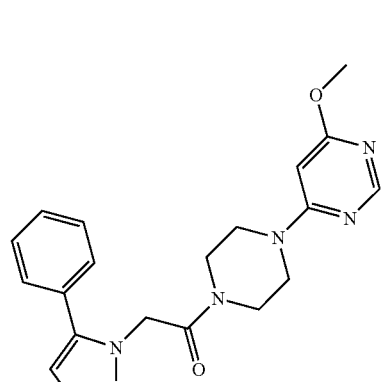 | 488 | method Q | 0.64 |

| Examples | Product | MS m/z [M + H]+ | HPLC Method | Rt min |
|---|---|---|---|---|
| 7.01.160 | | 402 | method M | 0.82 |
| 7.01.161 | | 401 | method M | 0.64 |
| 7.01.162 | | 432 | method M | 0.86 |
| 7.01.163 | | 432 | method M | 0.74 |

| Examples | Product | MS m/z [M + H]+ | HPLC Method | Rt min |
|---|---|---|---|---|
| 7.01.164 | 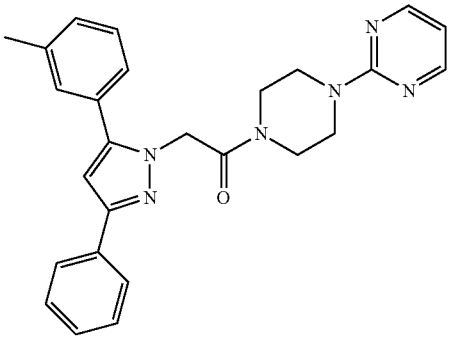 [SMILES: Cc1cccc(-c2cc(-c3ccccc3)nn2CC(=O)N2CCN(c3ncccn3)CC2)c1] | 439 | method Q | 0.82 |
| 7.01.165 | 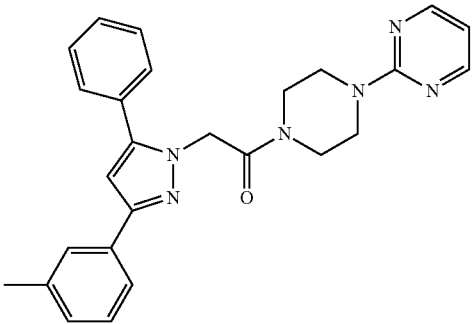 [SMILES: Cc1cccc(-c2cc(-c3ccccc3)n(CC(=O)N3CCN(c4ncccn4)CC3)n2)c1] | 439 | method Q | 0.82 |
| 7.01.166 | 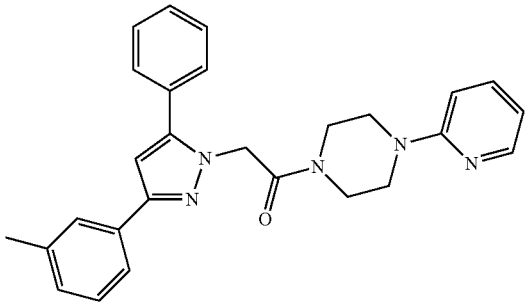 [SMILES: Cc1cccc(-c2cc(-c3ccccc3)n(CC(=O)N3CCN(c4ccccn4)CC3)n2)c1] | 438 | method Q | 0.70 |
| 7.01.167 | 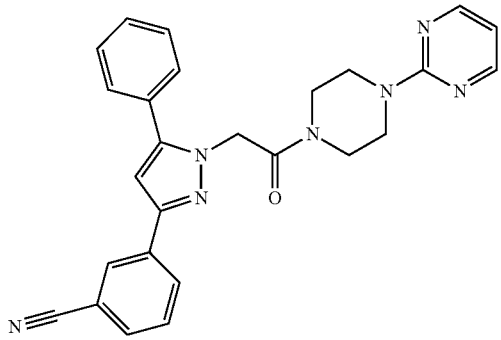 [SMILES: N#Cc1cccc(-c2cc(-c3ccccc3)n(CC(=O)N3CCN(c4ncccn4)CC3)n2)c1] | 450 | method M | 0.89 |

| Examples | Product | MS m/z [M + H]+ | HPLC Method | Rt min |
|---|---|---|---|---|
| 7.01.168 | 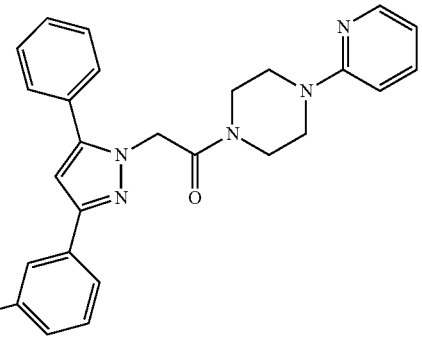 | 449 | method M | 0.72 |
| 7.01.169 | 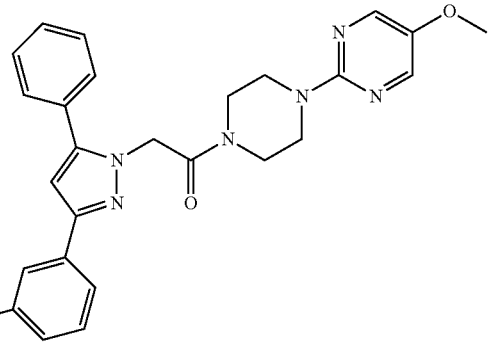 | 480 | method M | 0.92 |
| 7.01.170 | 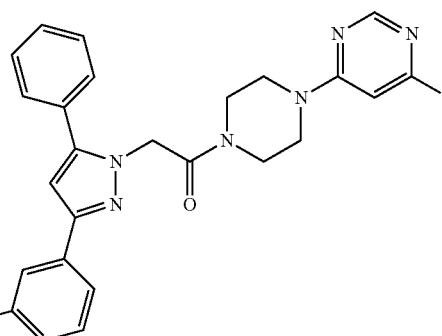 | 480 | method M | 0.81 |
| 7.01.171 | 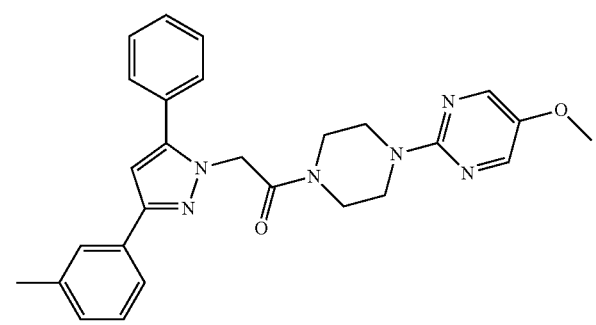 | 469 | method Q | 0.85 |

| Examples | Product | MS m/z [M + H]+ | HPLC Method | Rt min |
|---|---|---|---|---|
| 7.01.172 | | 450 | method M | 0.87 |
| 7.01.173 | | 469 | method Q | 0.85 |
| 7.01.174 | | 491 | method B | 1.43 |
| 7.01.175 | | 490 | method B | 1.26 |

-continued

| Examples | Product | MS m/z [M + H]+ | HPLC Method | Rt min |
|---|---|---|---|---|
| 7.01.176 | | 521 | method B | 1.34 |
| 7.01.177 | | 469 | method Q | 0.83 |
| 7.01.178 | | 492 | method M | 0.85 |

| Examples | Product | MS m/z [M + H]+ | HPLC Method | Rt min |
|---|---|---|---|---|
| 7.01.179 | | 491 | method M | 0.70 |
| 7.01.180 | | 522 | method M | 0.78 |
| 7.01.181 | | 409 | method M | 0.90 |

| Examples | Product | MS m/z [M + H]⁺ | HPLC Method | Rt min |
|---|---|---|---|---|
| 7.01.182 | 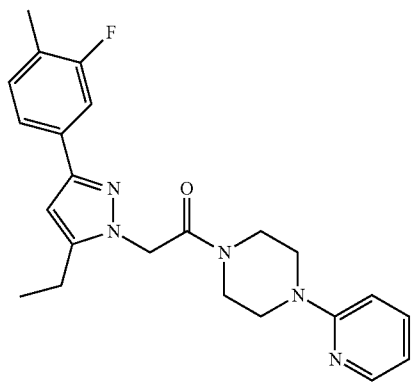 [SMILES: CCc1cc(-c2ccc(C)c(F)c2)nn1CC(=O)N1CCN(c2ccccn2)CC1] | 408 | method M | 0.74 |
| 7.01.183 | 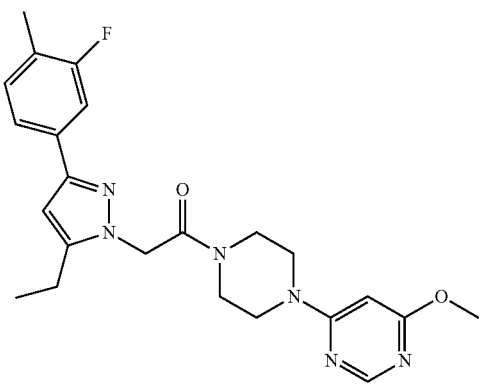 [SMILES: CCc1cc(-c2ccc(C)c(F)c2)nn1CC(=O)N1CCN(c2cc(OC)ncn2)CC1] | 439 | method M | 0.82 |
| 7.01.184 | 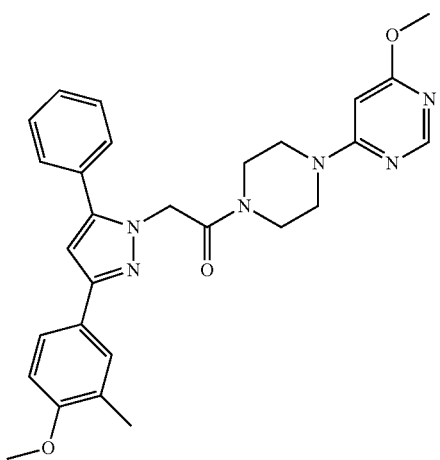 | 499 | method Q | 0.78 |

| Examples | Product | MS m/z [M + H]+ | HPLC Method | Rt min |
|---|---|---|---|---|
| 7.01.185 | | 424 | method M | 0.84 |
| 7.01.186 | | 423 | method M | 0.67 |
| 7.01.187 | | 454 | method M | 0.76 |
| 7.01.188 | | 457 | method M | 0.98 |

-continued

| Examples | Product | MS m/z [M + H]+ | HPLC Method | Rt min |
|---|---|---|---|---|
| 7.01.189 | | 456 | method M | 0.81 |
| 7.01.190 | | 487 | method M | 0.91 |
| 7.01.191 | | 475 | method K | 0.78 |
| 7.01.192 | | 505 | method K | 0.77 |

7.02.01. 2-(3,5-diphenyl-pyrazol-1-yl)-1-(4-(2-pyrimidinyl)-1-piperazinyl)-ethanon

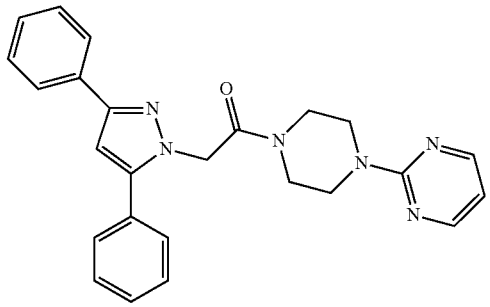 [SMILES: O=C(Cn1nc(-c2ccccc2)cc1-c1ccccc1)N1CCN(c2ncccn2)CC1]

278 mg (3,5-diphenyl-pyrazol-1-yl)-acetic acid was dissolved in 5 mL DMF. 321 mg TBTU and 172 µL DIPEA were added to this solution and the mixture was stirred for a few minutes at RT. 164 mg 2-(1-piperazinyl)-pyrimidine was added and stiffing was continued for 30 min. Then 10 mL of a 1M NaOH solution and 50 mL $CH_2Cl_2$ were added, the organic phase was separated. The solvent was removed and the residue was purified by flash chromatography (silica gel, DCM/MeOH/NH3 0-5%). Diethylether was given to the residue and the precipitate was filtered to yield 310 mg of the desired compound.

$R_f$: 1.48 (method F)

$(M+H)^+$: 425

By using the same synthesis strategy as for 2-(3,5-diphenyl-pyrazol-1-yl)-1-(4-(2-pyrimidinyl)-1-piperazinyl)-ethanon the following compounds were obtained:

| Examples | Product | MS m/z [M + H]+ | HPLC Method | Rt min |
|---|---|---|---|---|
| 7.02.02 | 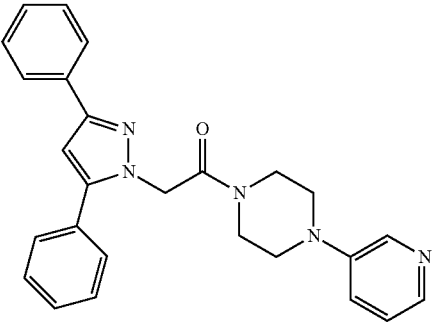 [SMILES: O=C(Cn1nc(-c2ccccc2)cc1-c1ccccc1)N1CCN(c2cccnc2)CC1] | 424 | method F | 1.19 |
| 7.02.03 | 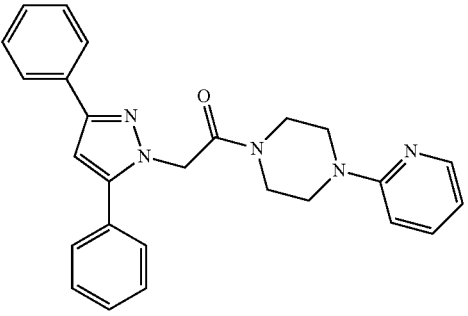 [SMILES: O=C(Cn1nc(-c2ccccc2)cc1-c1ccccc1)N1CCN(c2ccccn2)CC1] | 424 | method F | 1.2 |
| 7.02.04 | 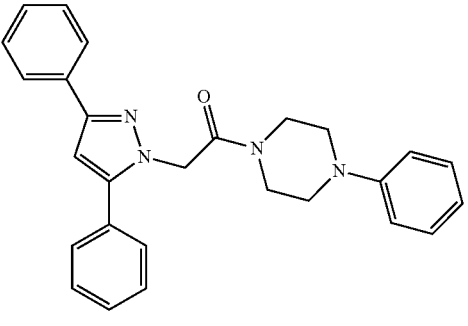 [SMILES: O=C(Cn1nc(-c2ccccc2)cc1-c1ccccc1)N1CCN(c2ccccc2)CC1] | 423 | method F | 1.57 |

-continued

| Examples | Product | MS m/z [M + H]⁺ | HPLC Method | Rt min |
|---|---|---|---|---|
| 7.02.05 | | 425 | method F | 1.46 |
| 7.02.06 | | 424 | method F | 1.19 |
| 7.02.07 | | 474 | method L | 2.13 |
| 7.02.08 | | 449 | method L | 2.08 |

| Examples | Product | MS m/z [M + H]+ | HPLC Method | Rt min |
|---|---|---|---|---|
| 7.02.09 | | 449 | method L | 2.09 |
| 7.02.10 | | 492 | method L | 2.43 |
| 7.02.11 | | 503 | method L | 2.50 |
| 7.02.12 | | 493 | method L | 2.45 |

-continued

| Examples | Product | MS m/z [M + H]+ | HPLC Method | Rt min |
|---|---|---|---|---|
| 7.02.13 | | 492 | method L | 2.43 |
| 7.02.14 | | 426 | method L | 2.26 |
| 7.02.15 | | 425 | method N | 1.50 |
| 7.02.16 | | 424 | method N | 1.26 |
| 7.02.17 | | 454 | method N | 1.30 |

-continued
| Examples | Product | MS m/z [M + H]+ | HPLC Method | Rt min |
|---|---|---|---|---|
| 7.02.18 | 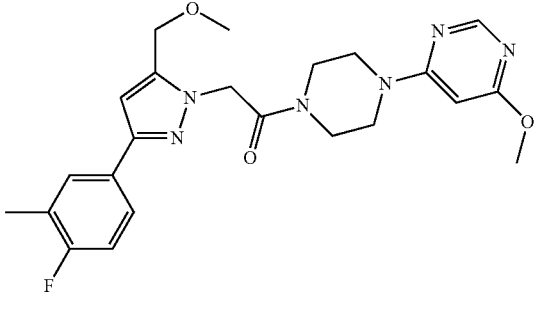 | 455 | method N | 1.40 |
| 7.02.19 | 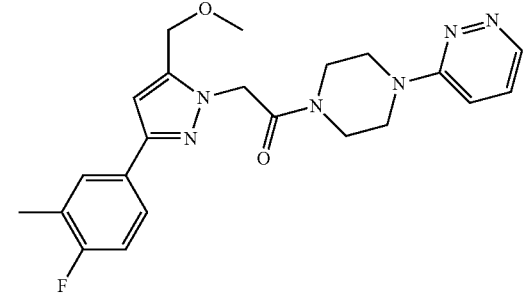 [SMILES: COCc1cc(-c2ccc(F)c(C)c2)nn1CC(=O)N1CCN(c2ccccn2)CC1] | 425 | method N | 1.30 |
| 7.02.20 | 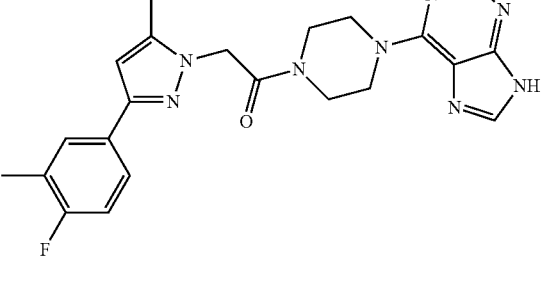 | 465 | method N | 1.35 |
| 7.02.21 | 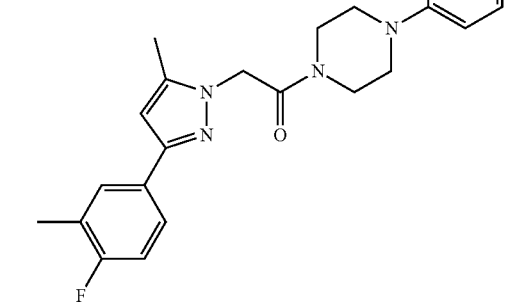 | 393 | method P | 1.00 |

-continued
| Examples | Product | MS m/z [M + H]+ | HPLC Method | Rt min |
|---|---|---|---|---|
| 7.02.22 | 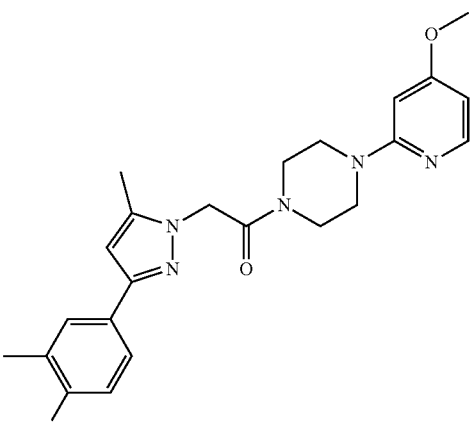 | 423 | method P | 1.60 |
| 7.02.23 | 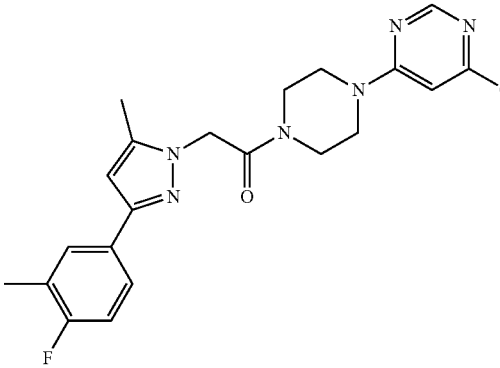 | 425 | method P | 1.10 |
| 7.02.24 | 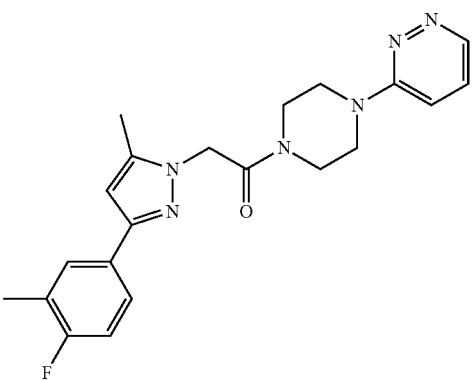 [SMILES: Cc1cc(-c2cc(C)n(CC(=O)N3CCN(c4cccnn4)CC3)n2)ccc1F] | 395 | method P | 1.00 |
| 7.02.25 | 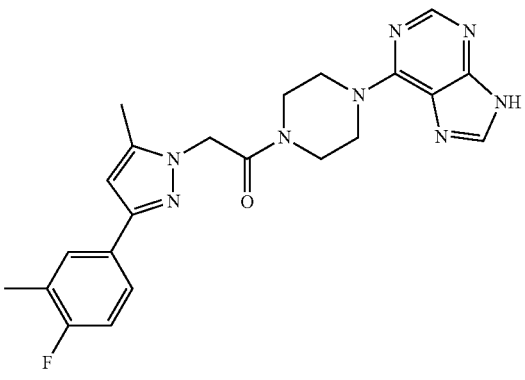 [SMILES: Cc1cc(-c2cc(C)n(CC(=O)N3CCN(c4ncnc5[nH]cnc45)CC3)n2)ccc1F] | 435 | method P | 1.10 |

| Examples | Product | MS m/z [M + H]+ | HPLC Method | Rt min |
|---|---|---|---|---|
| 7.02.26 | | 425 | method P | 1.60 |
| 7.02.27 | | 455 | method AE | 0.79 |

7.03.01. 2-(3,5-bis-(4-methoxy-phenyl))-pyrazol-1-yl)-1-(4-(2-pyrimidinyl)-1-piperazinyl)-ethanon

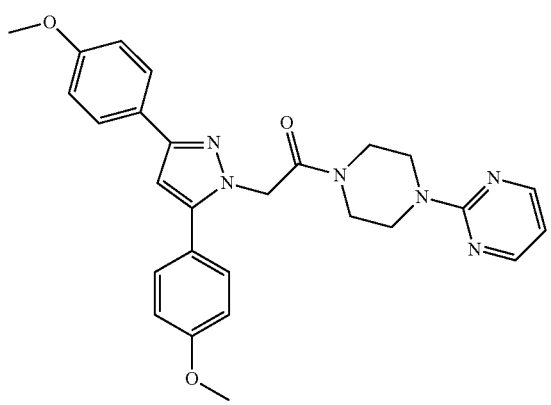 [SMILES: COc1ccc(-c2cc(-c3ccc(OC)cc3)n(CC(=O)N3CCN(c4ncccn4)CC3)n2)cc1]

100 mg (3,5-bis-(4-methoxy-phenyl)-pyrazol-1-yl)-acetic acid acid was dissolved in 4 mL DMF. 135 mg HATU and 200 µL DIPEA were added to this solution and the mixture was stirred for 15 min at RT. Then 77 mg 2-(1-piperazinyl)-pyrimidine hydrochloride was added. The mixture was stirred over night. The reaction was diluted with potassium carbonat solution and extracted with dichlormethane. The organic layer was evaporated. The residue was purified by HPLC to give 36 mg of the desired compound.

$R_t$: 1.52 (method C)

$(M+H)^+$: 485

7.04.01. 2-(3,5-bis-(2-fluor-phenyl))-pyrazol-1-yl)-1-(4-(2-pyrimidinyl)-1-piperazinyl)-ethanon

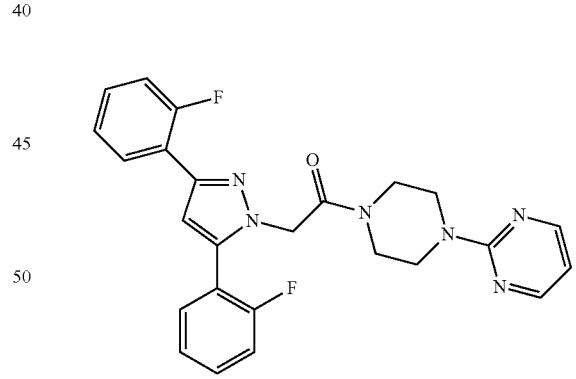

200 mg 3,5-bis-(2-fluoro-phenyl)-1H-pyrazole, 222 mg 2-bromo-1-(4-pyrimidin-2-yl-piperazin-1-yl)-ethanon and 500 mg potassiumcarbonat in 20 mL acetone was stirred 24 h by RT. The reaction was filtered and the filtrate was evaporated. The residue was crystallized with acetonitrile to yield 254 mg of the desired compound.

$R_t$: 1.57 min (method C).

$(M+H)^+$: 461.

By using the same synthesis strategy as for 2-(3,5-bis-(2-fluor-phenyl))-pyrazol-1-yl)-1-(4-(2-pyrimidinyl)-1-piperazinyl)-ethanon the following compounds were obtained:

| Examples | Product | MS m/z [M + H]+ | HPLC Method | Rt min |
|---|---|---|---|---|
| 7.04.02 | | 449 | method C | 1.65 |
| 7.04.03 | | 483 | method C | 1.57 |

7.05.01. 2-[3-(4-fluoro-3-methyl-phenyl)-5-phenyl-pyrazol-1-yl]-1-{4-[6-(2-morpholin-4-yl-ethoxy)-pyrimidin-4-yl]-piperazin-1-yl}-ethanone

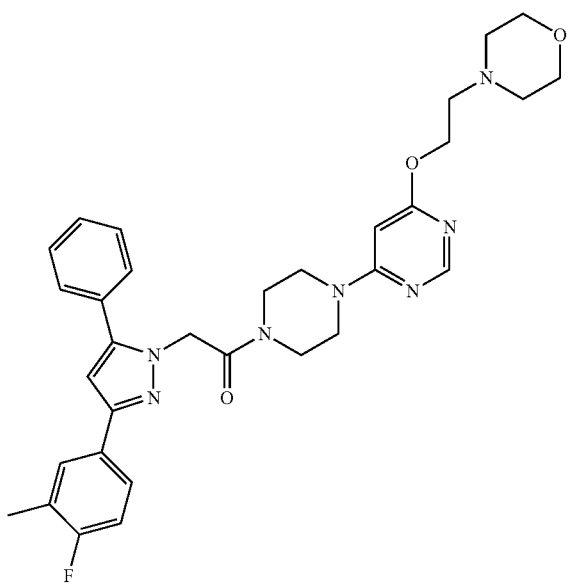 [SMILES: Cc1cc(-c2cc(-c3ccccc3)n(CC(=O)N3CCN(c4cc(OCCN5CCOCC5)ncn4)CC3)n2)ccc1F]

50 mg (3,5-Bis-(4-methoxy-phenyl)-pyrazol-1-yl)-acetic acid was added to 68 mg N-(2-hydroxyethyl) morpholine and 14.1 mg potasiumcarbonate in 2 mL n-methyl-2-pyrrolidinone. The reaction was stirred 30 min at 120° C. and 15 min at 200° C. under microwave conditions. The solvent was removed and the residue was purified by HPLC.

$R_t$: 1.34 min (method X)

$(M+H)^+$: 586

By using the same synthesis strategy as for 2-[3-(4-fluoro-3-methyl-phenyl)-5-phenyl-pyrazol-1-yl]-1-{4-[6-(2-morpholin-4-yl-ethoxy)-pyrimidin-4-yl]-piperazin-1-yl}-ethanone the following compounds were obtained:

| Examples | Product | MS m/z [M + H]+ | HPLC Method | Rt min |
|---|---|---|---|---|
| 7.05.02 | | 531 | method X | 1.34 |
The invention claimed is:
1. A compound selected from the group consisting of
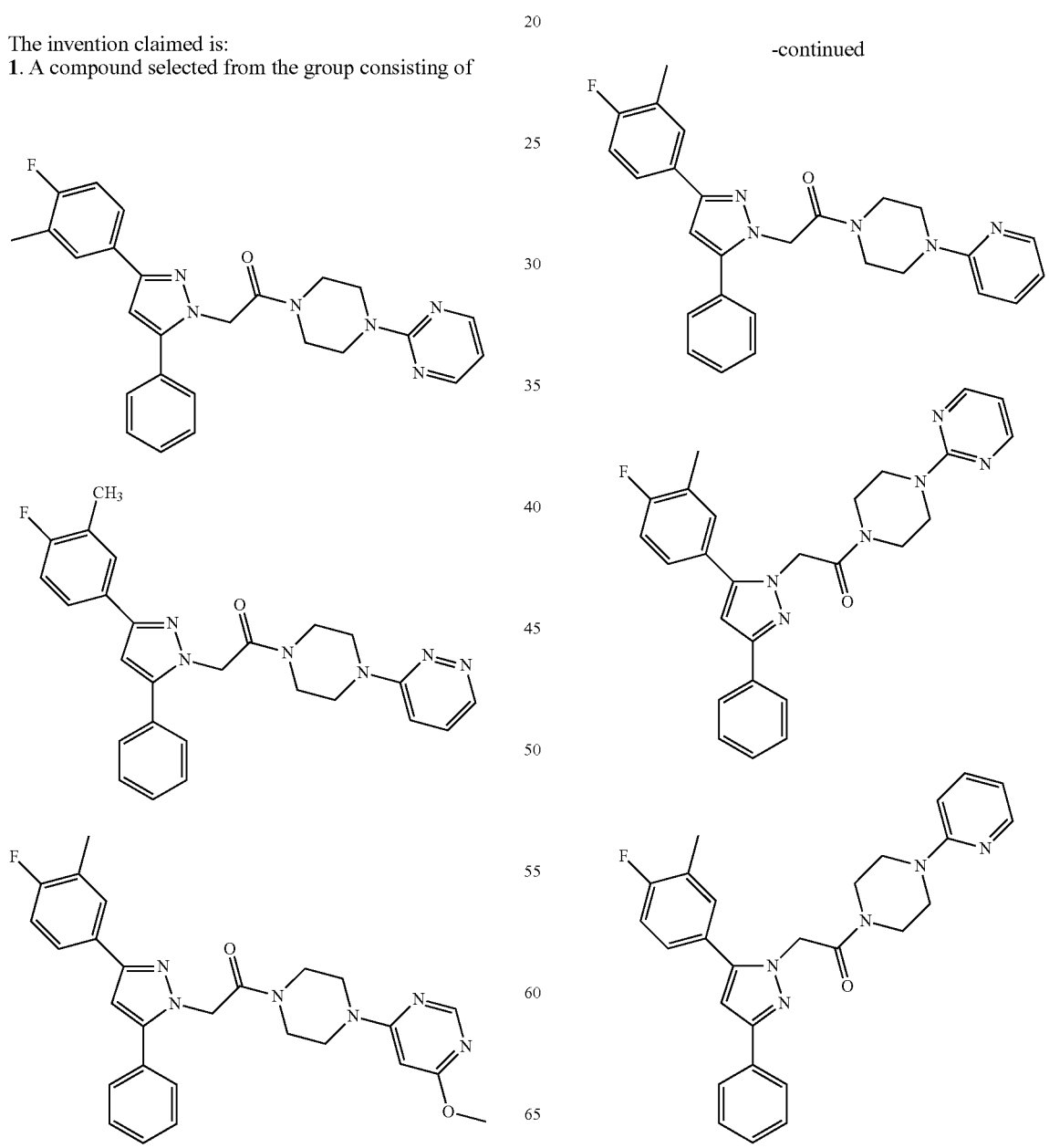

209
-continued
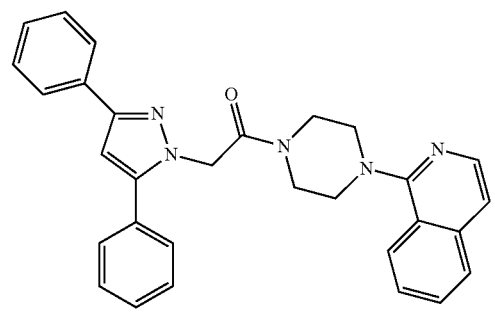
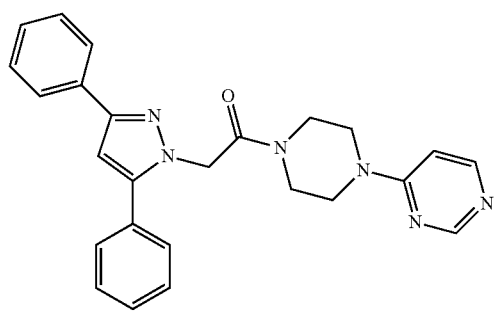
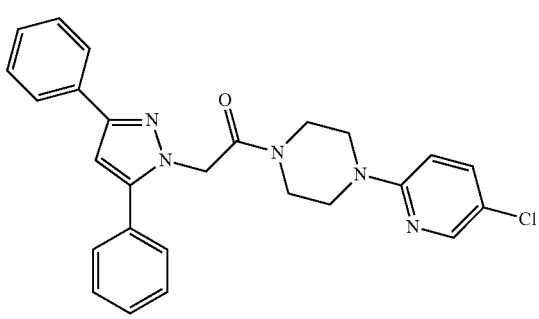
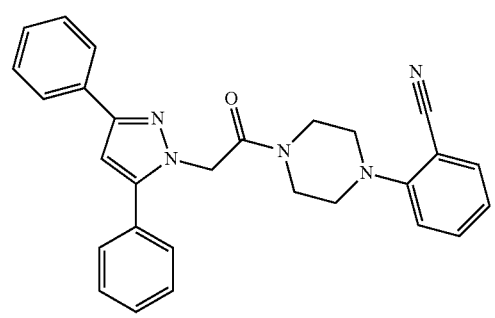
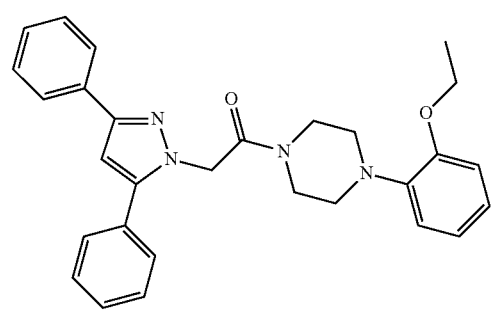
210
-continued
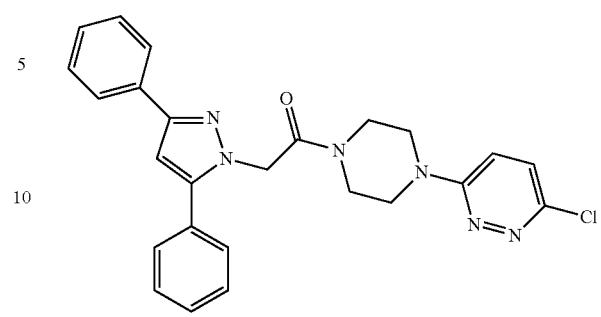
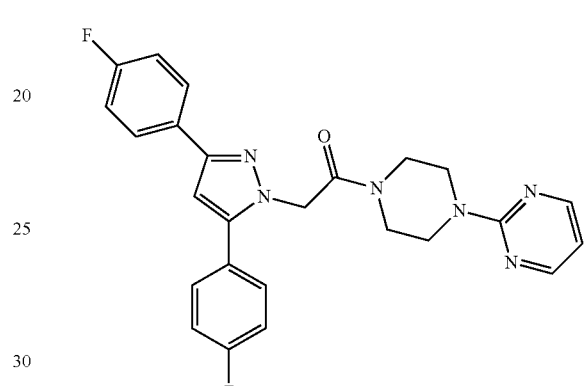
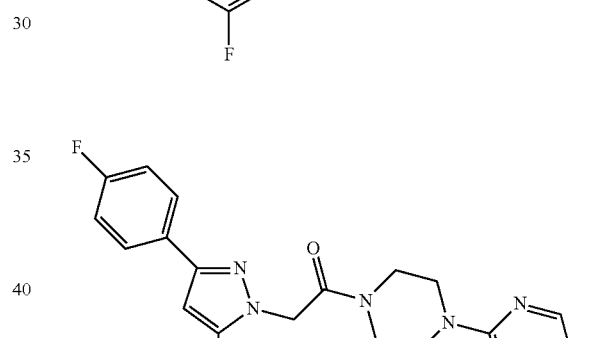
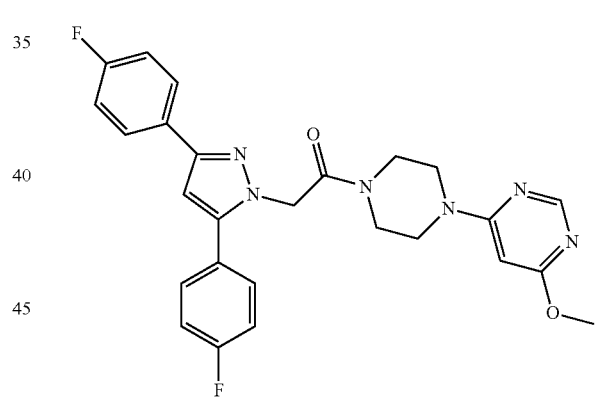
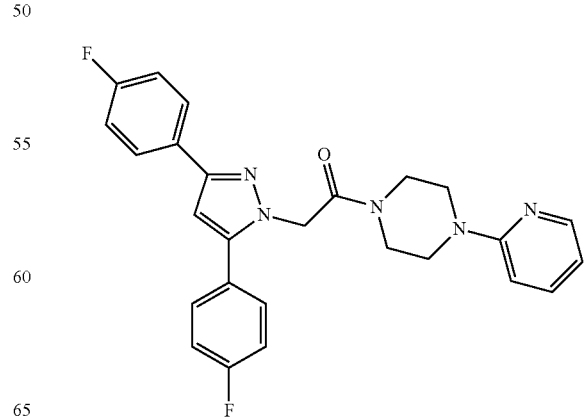

211
-continued
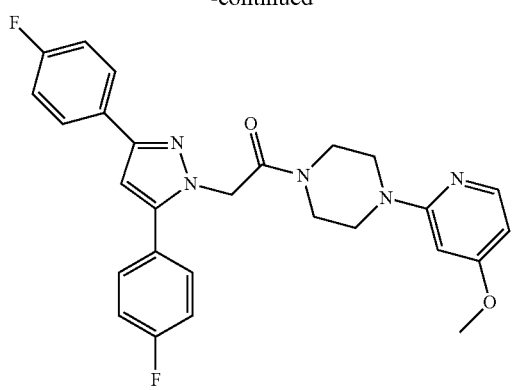
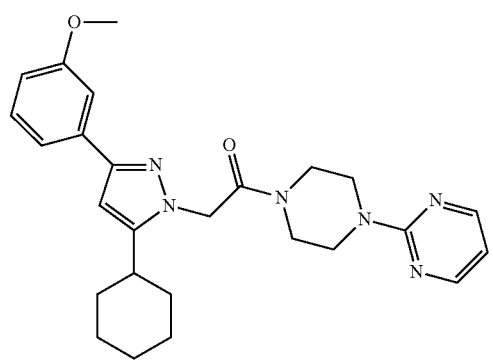
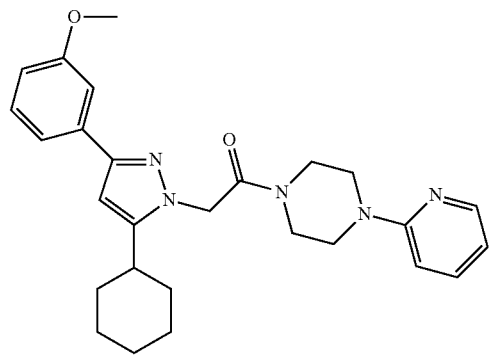
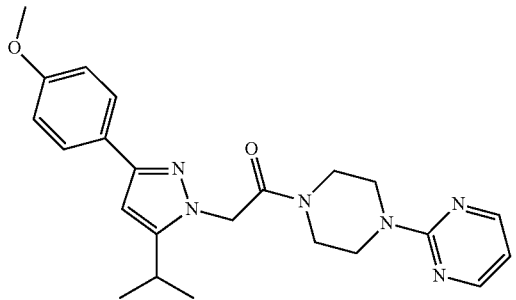
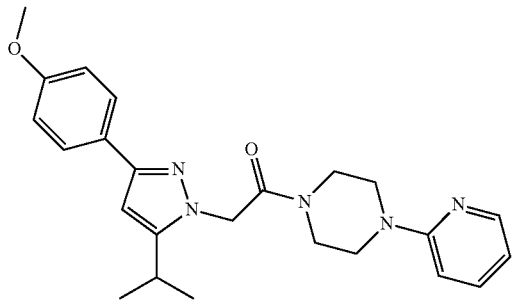
212
-continued
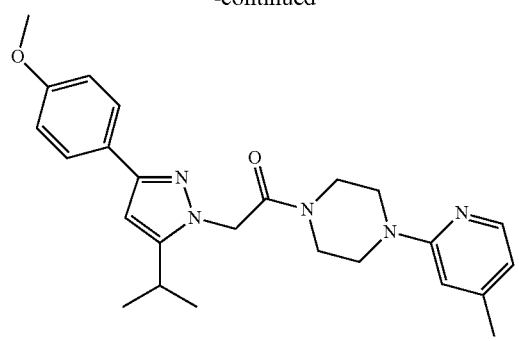
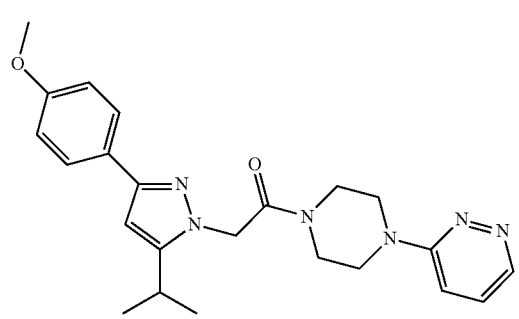
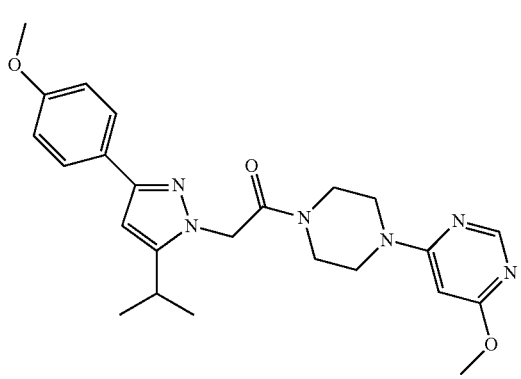
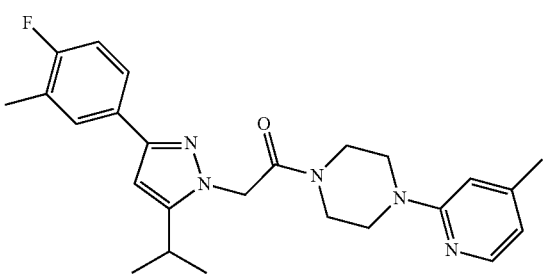
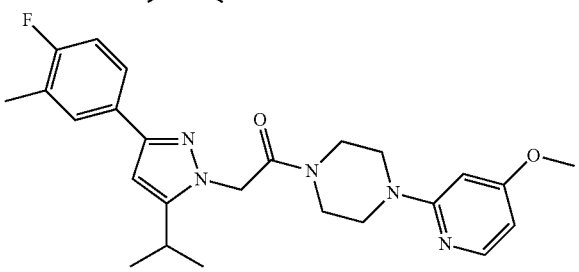

213
-continued
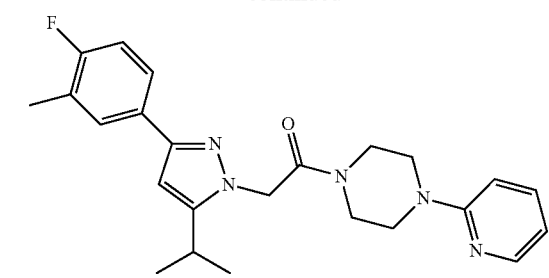
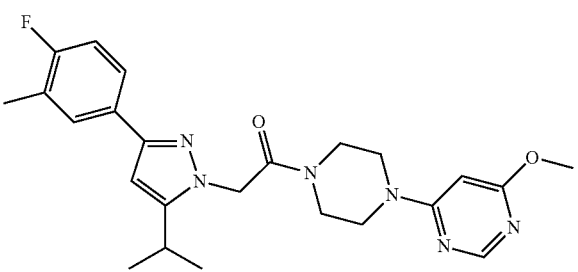
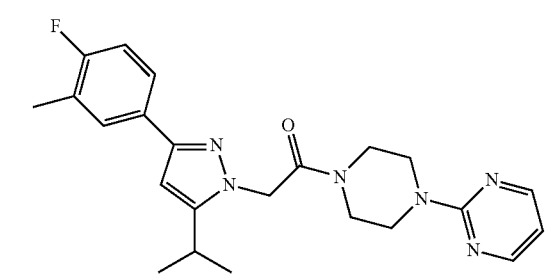
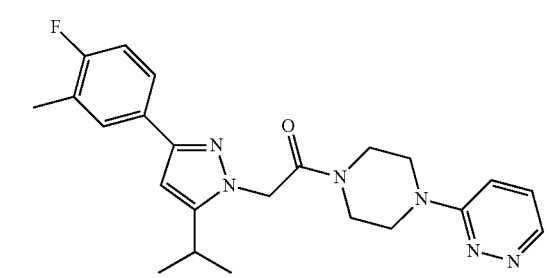
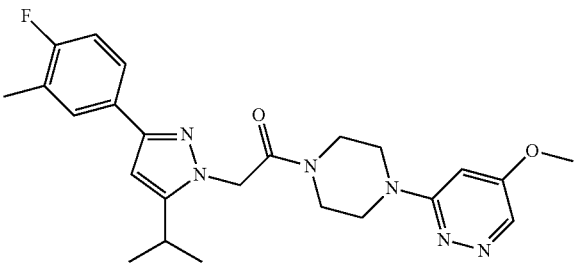
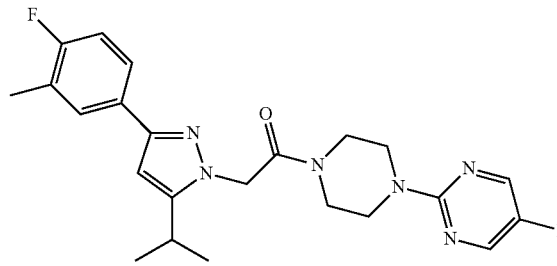
214
-continued
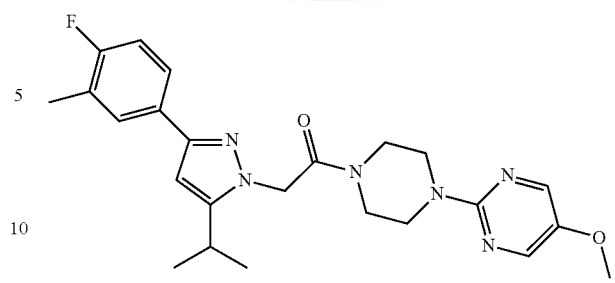
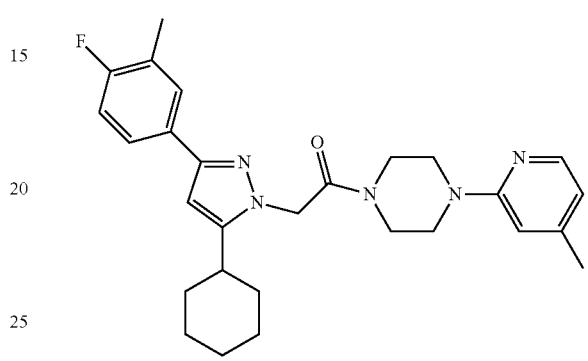
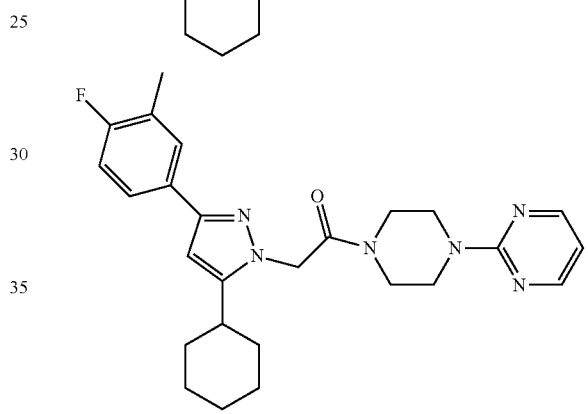
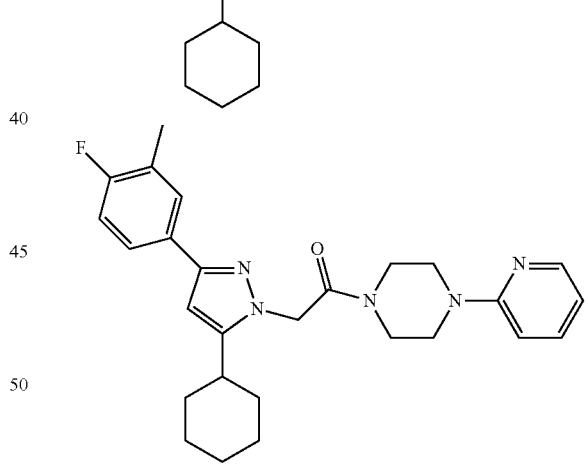
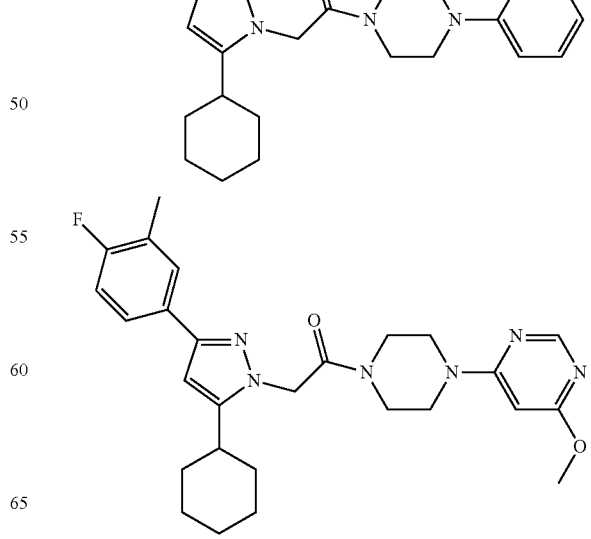

215
-continued
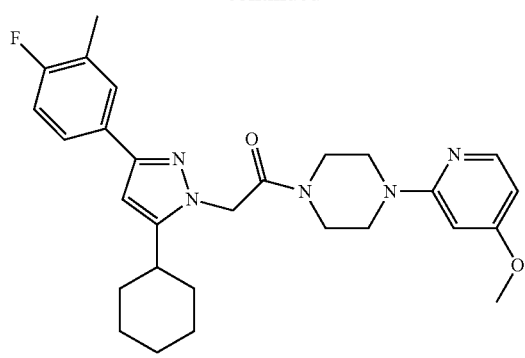
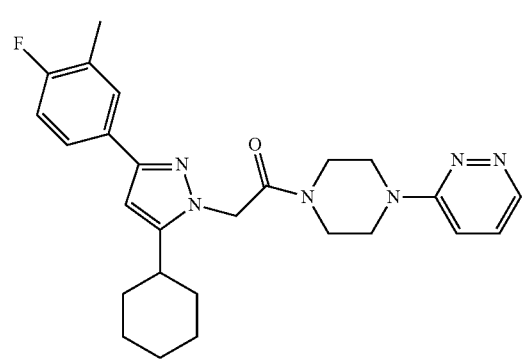
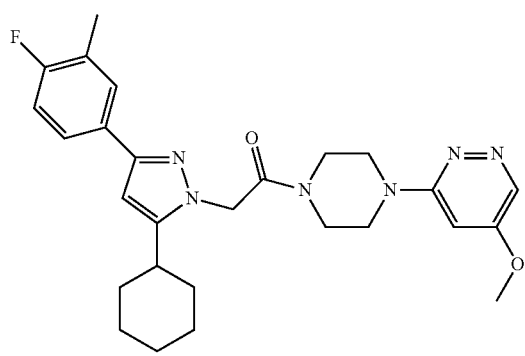
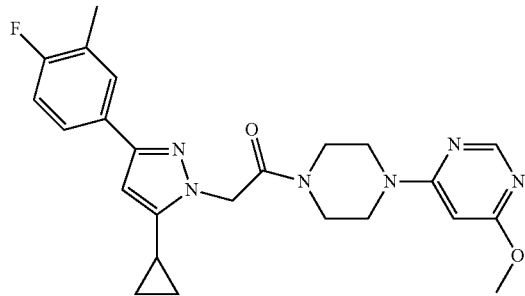
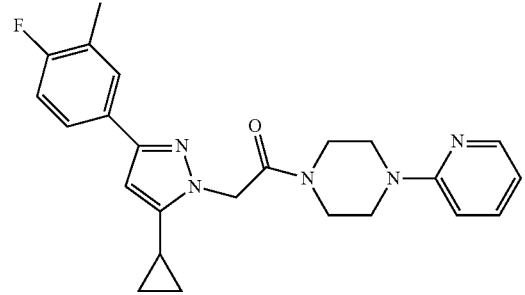
216
-continued
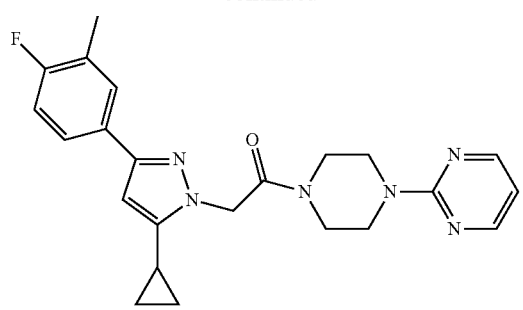
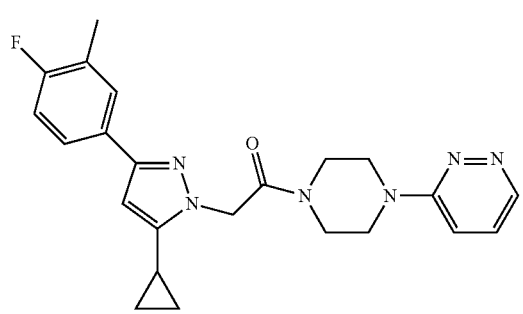
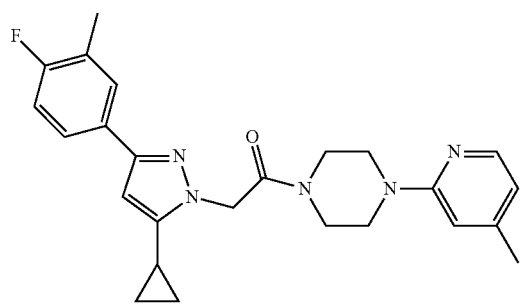
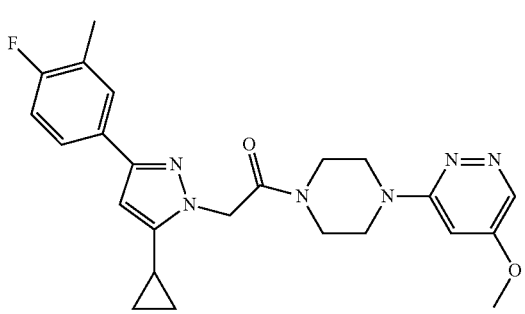
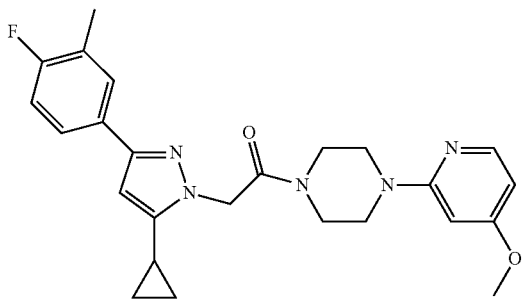

217
-continued
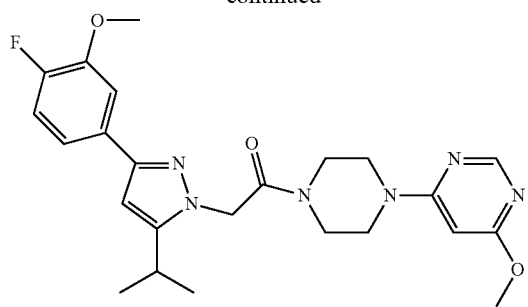
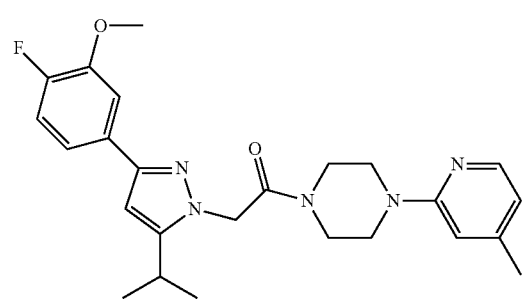
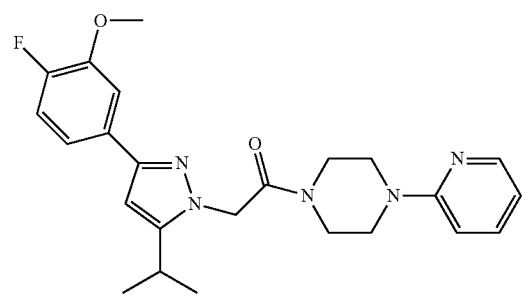
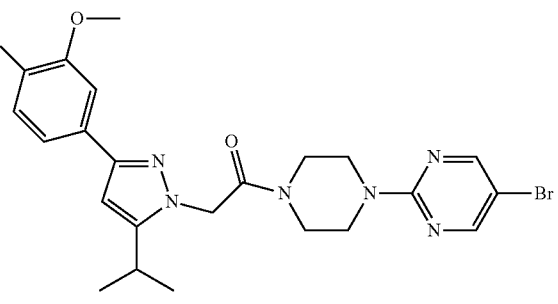
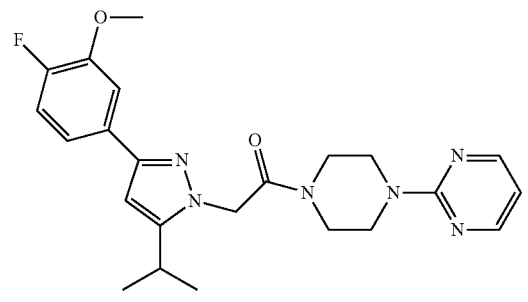
218
-continued
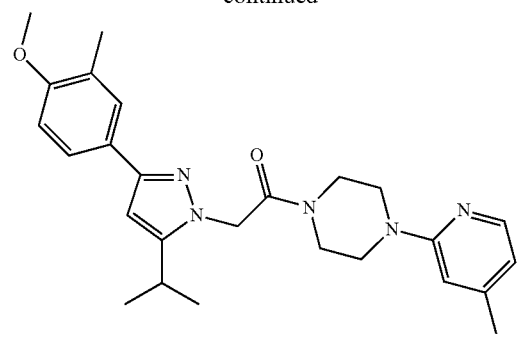
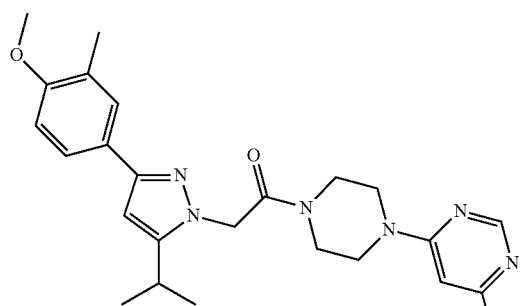
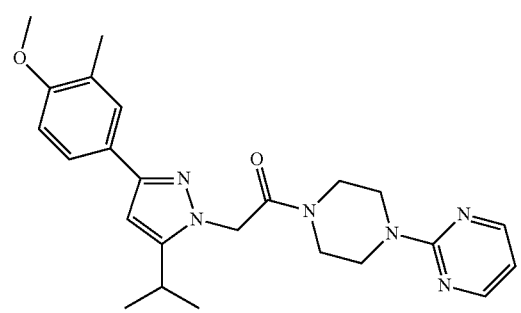
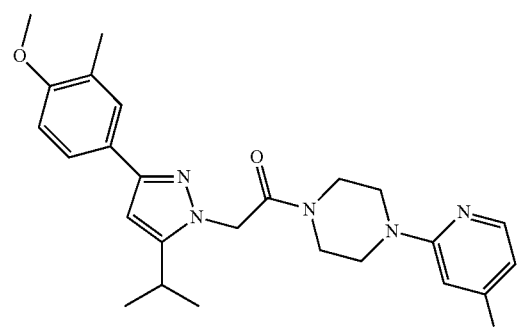
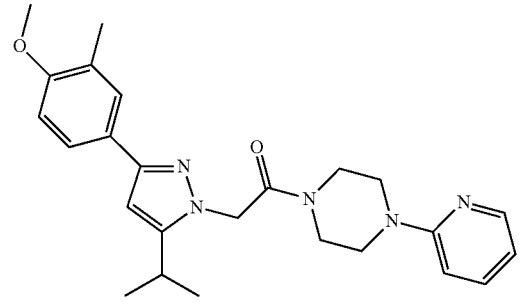

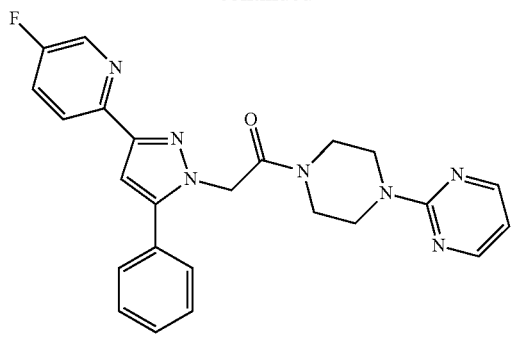
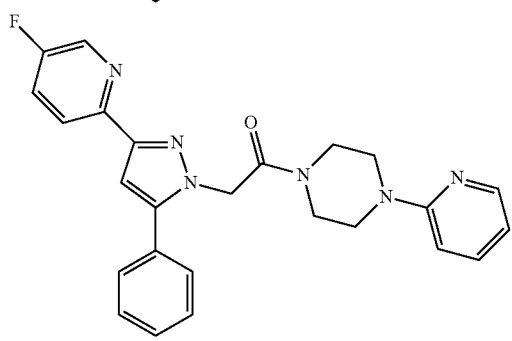
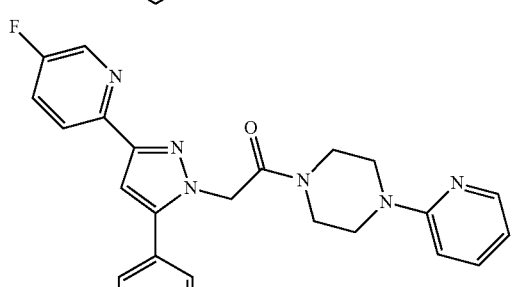
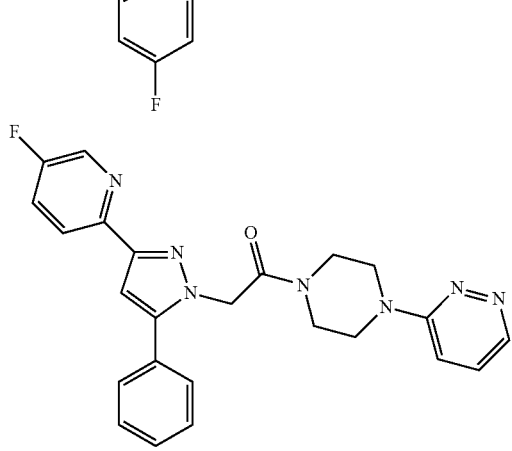
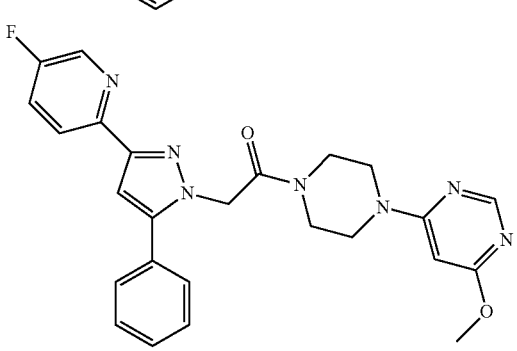
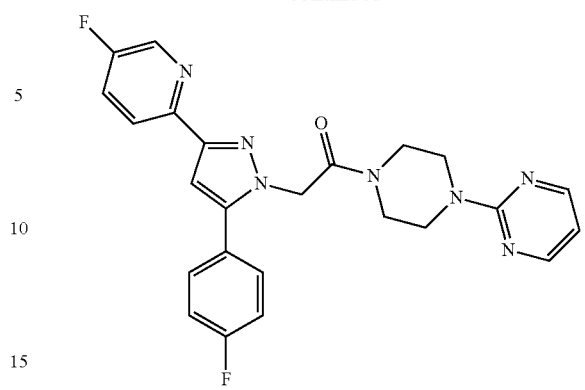
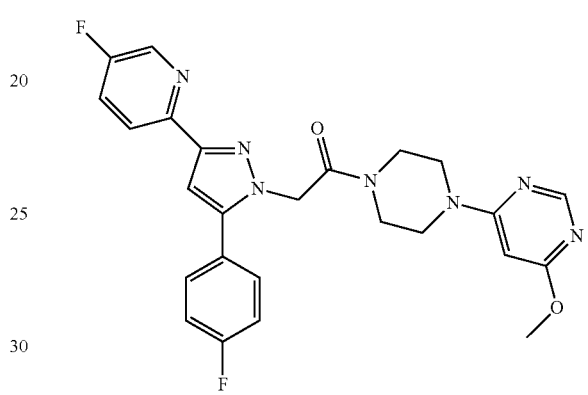
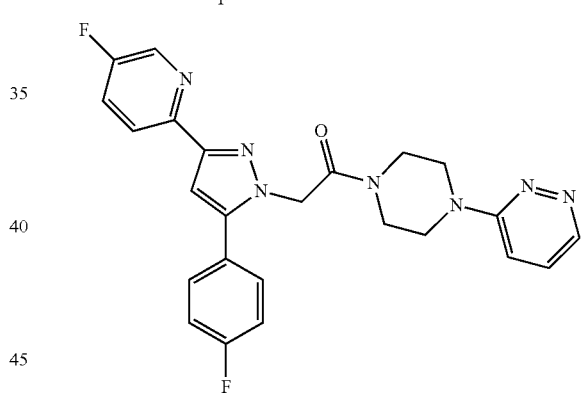
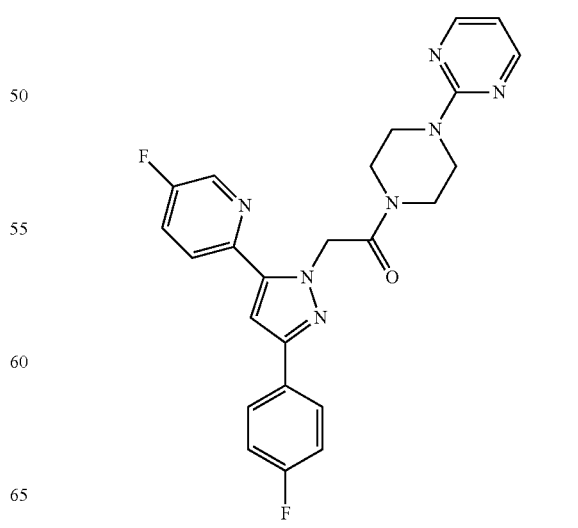

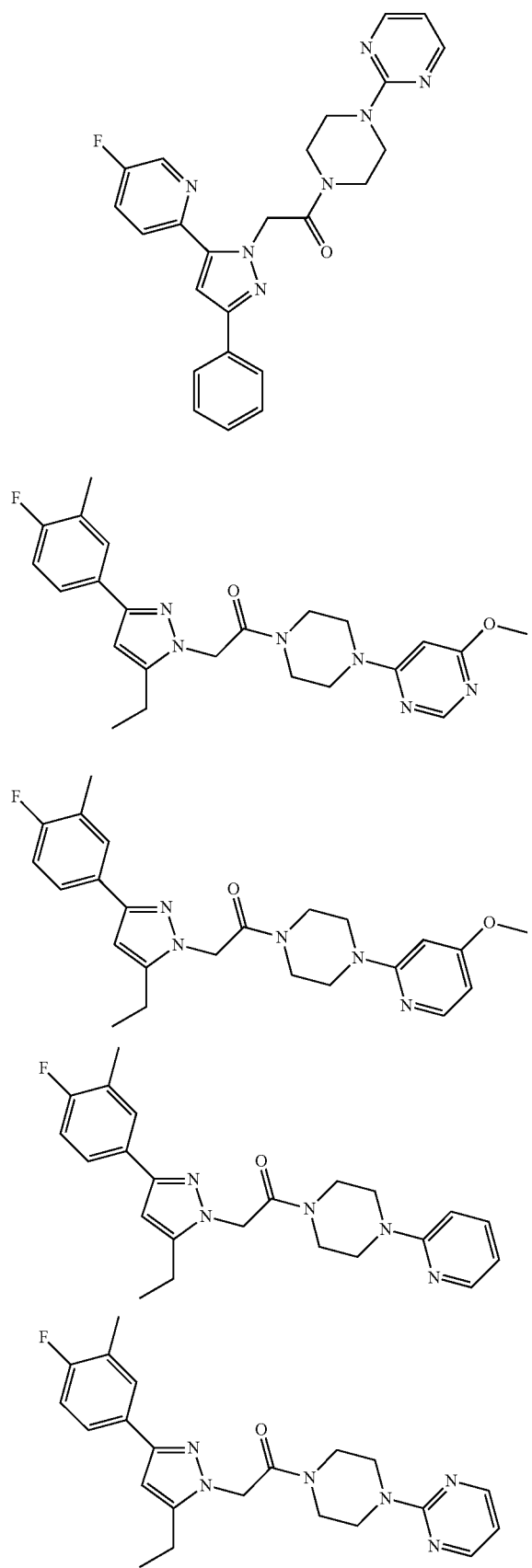
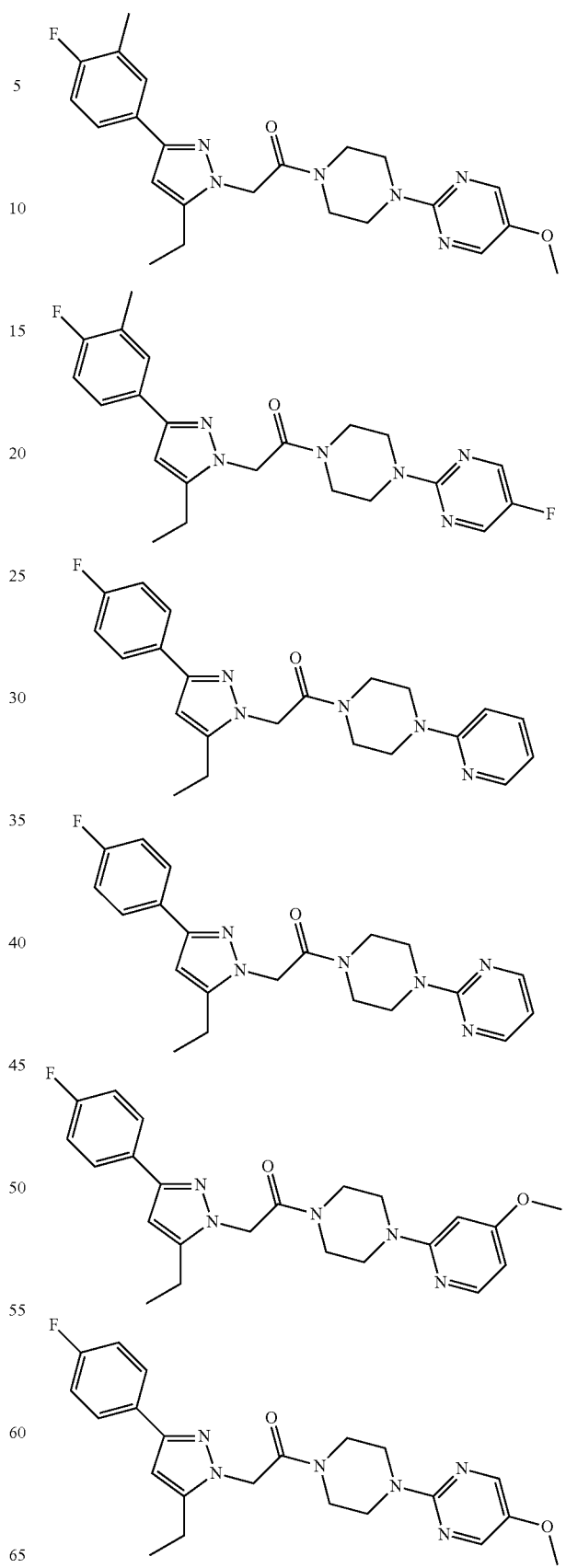

223
-continued
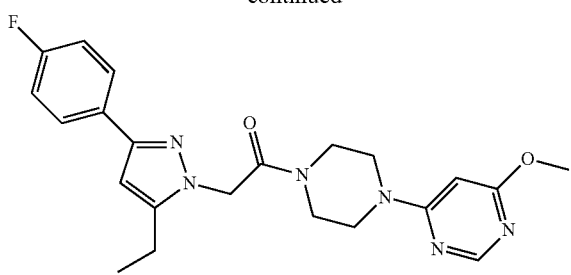
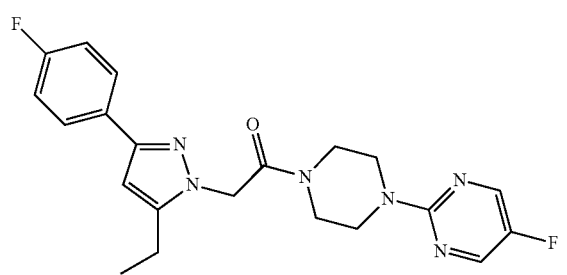
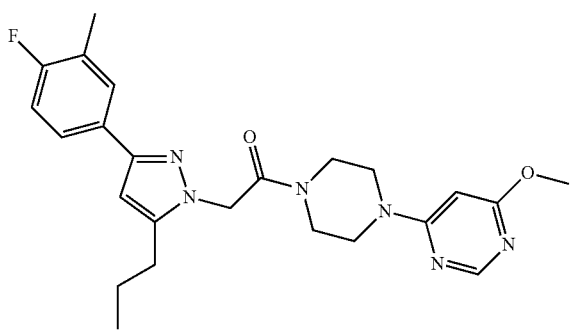
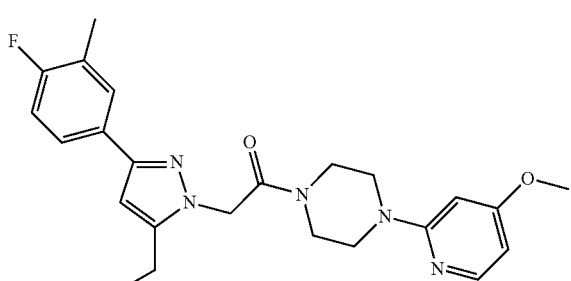
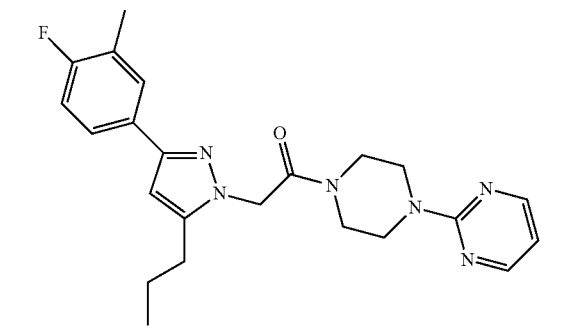
224
-continued
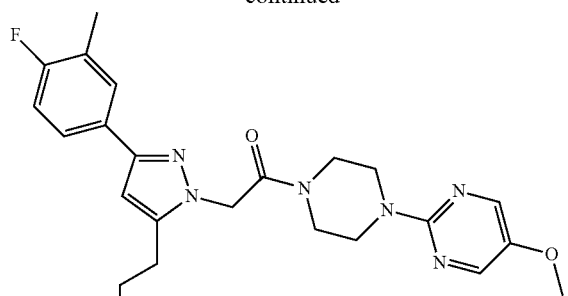
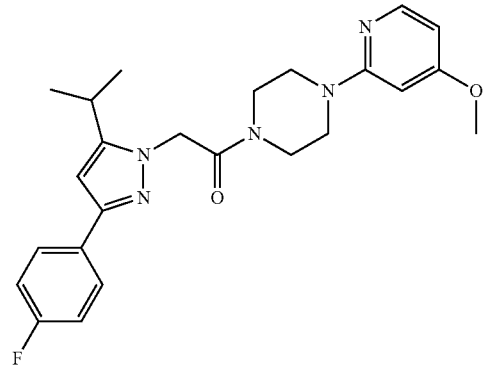
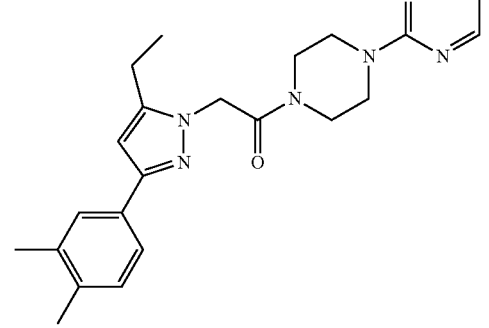

225
-continued
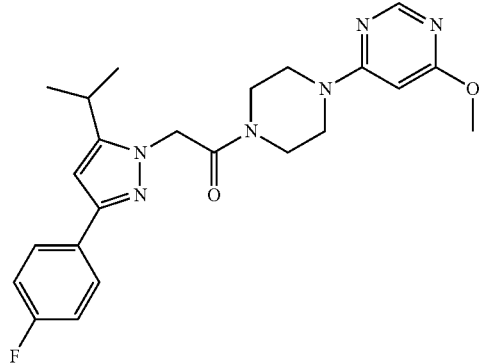
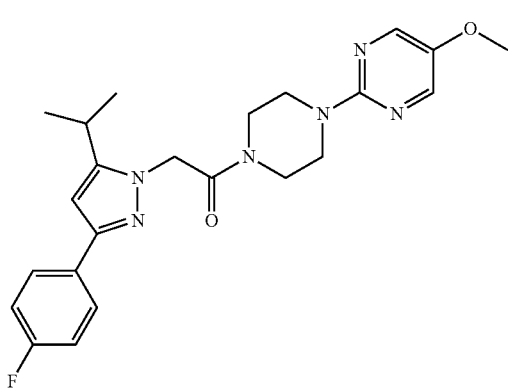
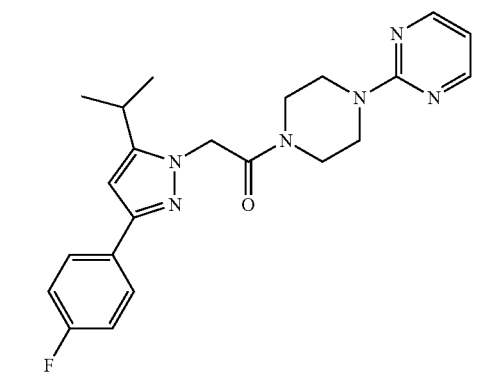
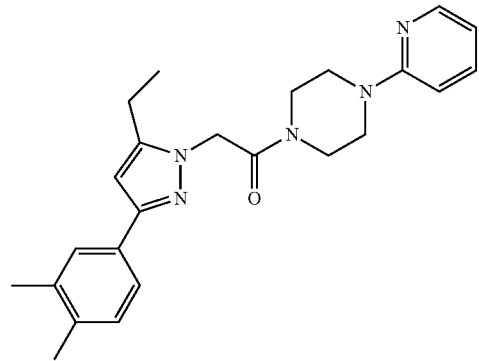
226
-continued
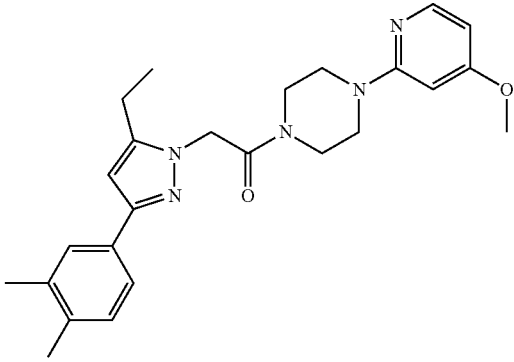
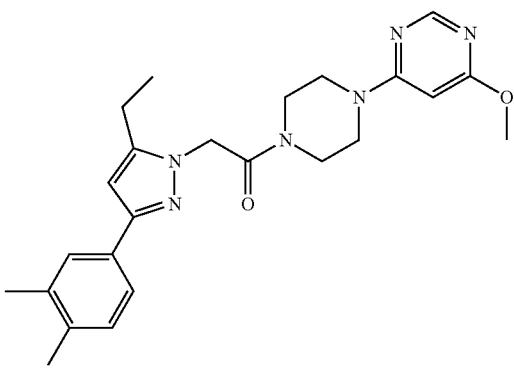
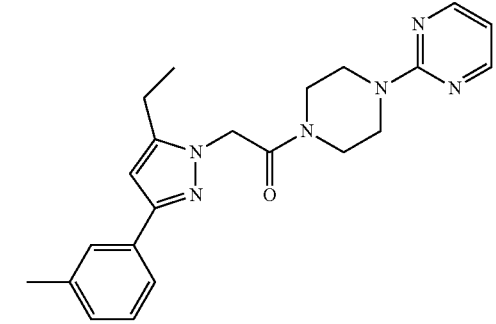
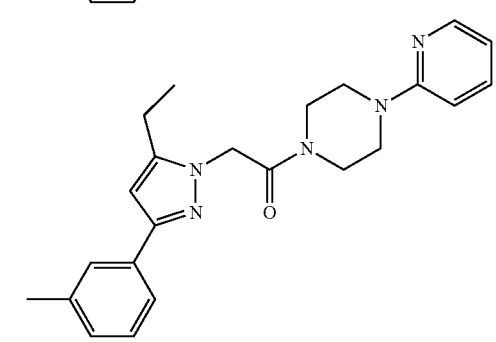
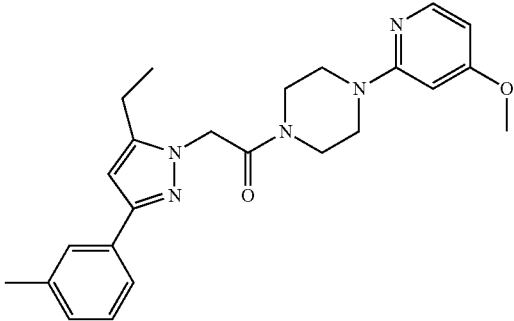

227
-continued
228
-continued
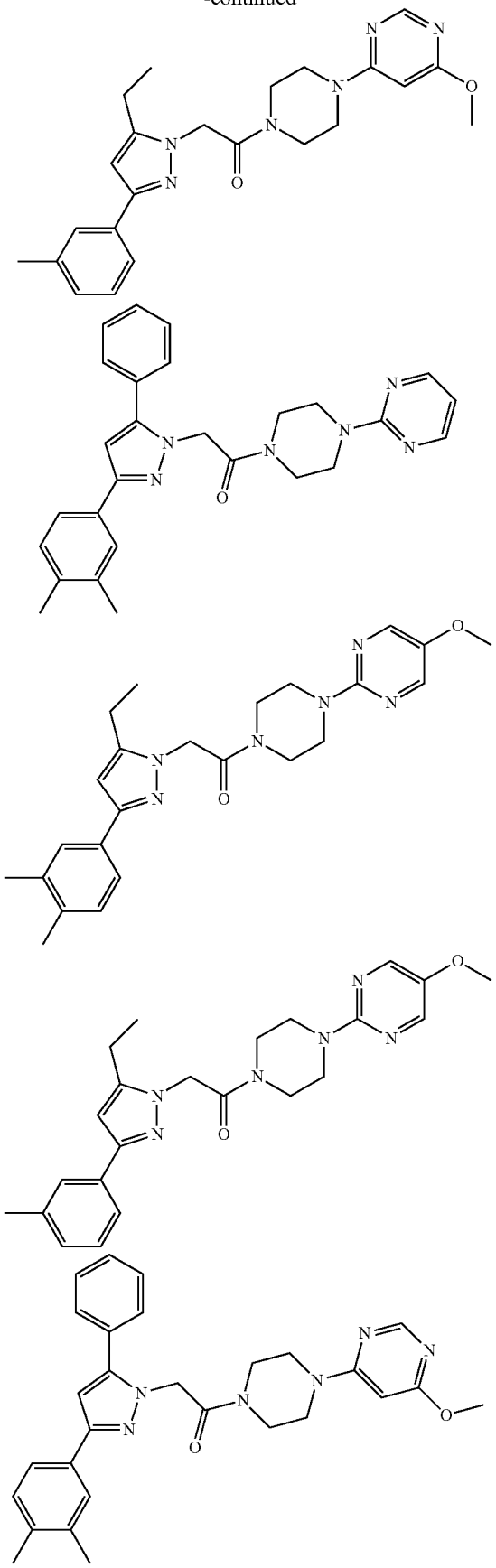
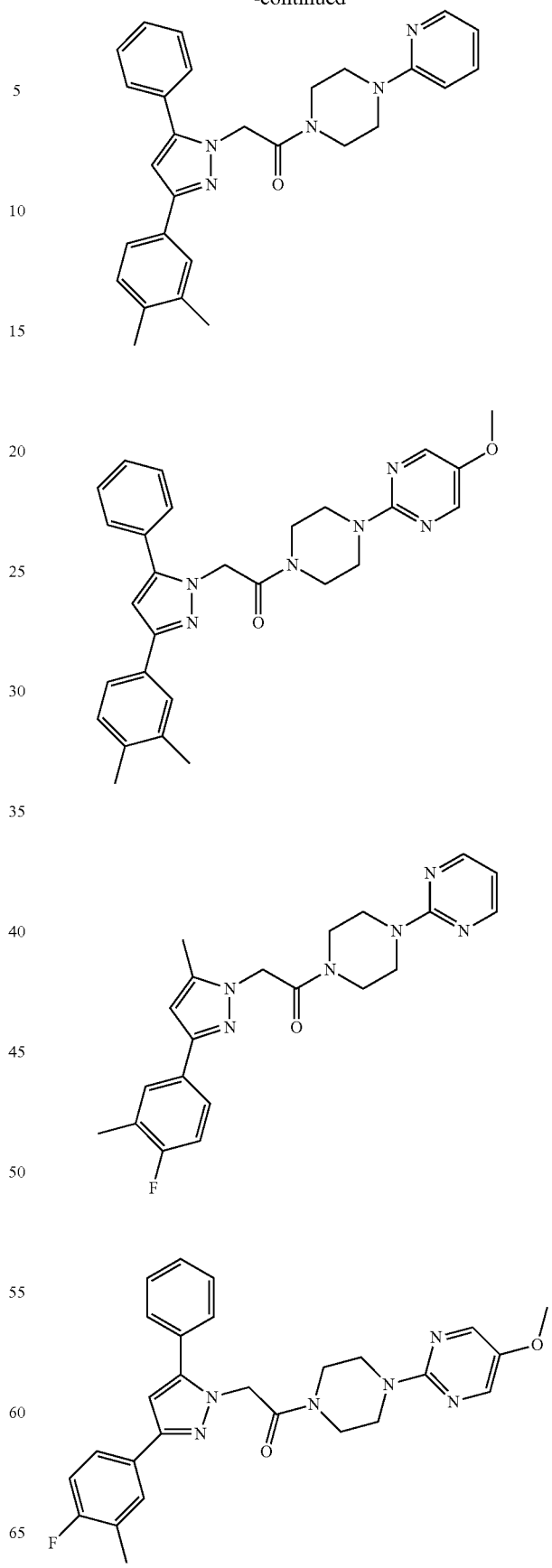

229
-continued
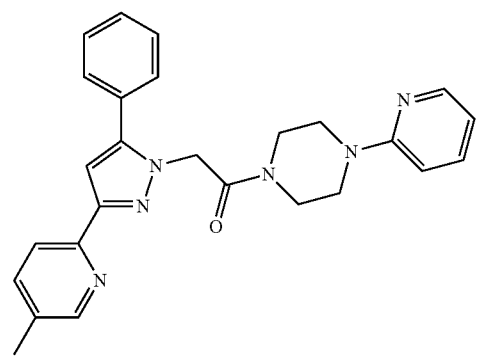
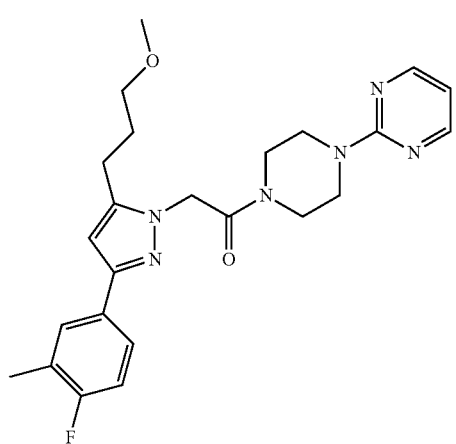
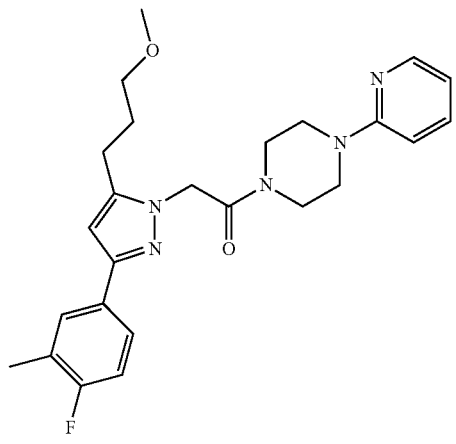
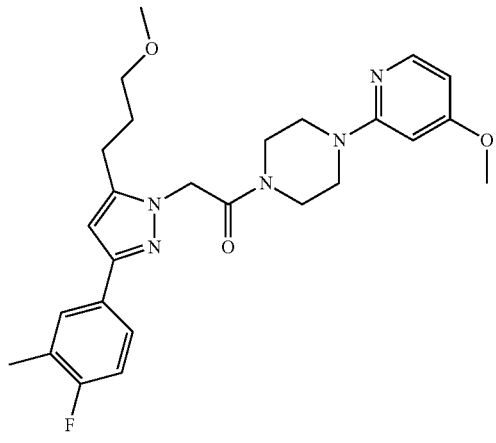
230
-continued
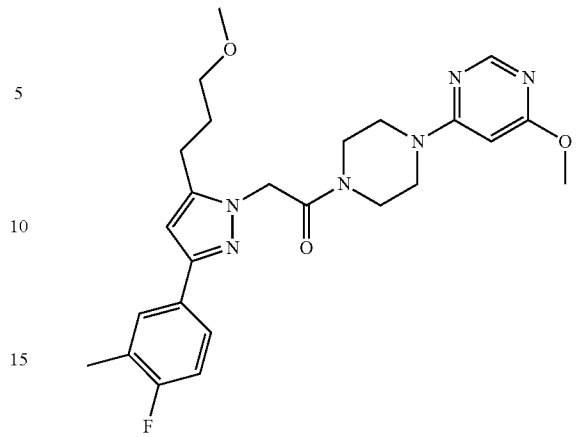
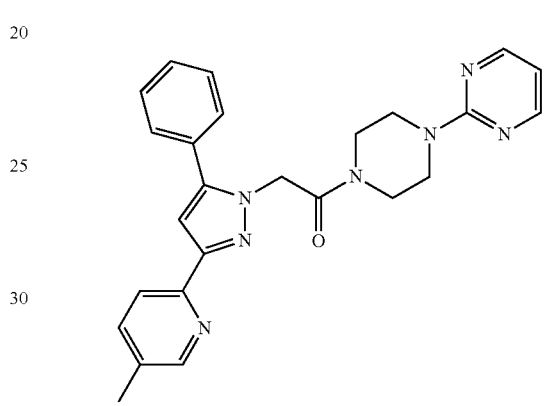
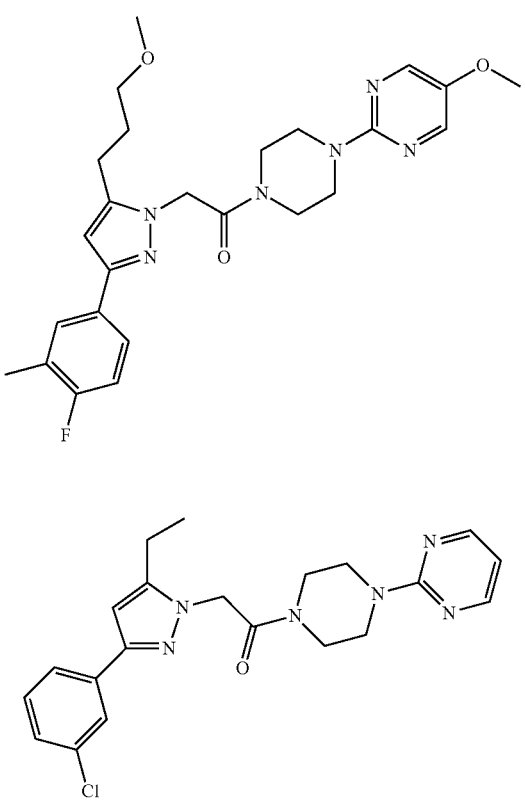

231
-continued
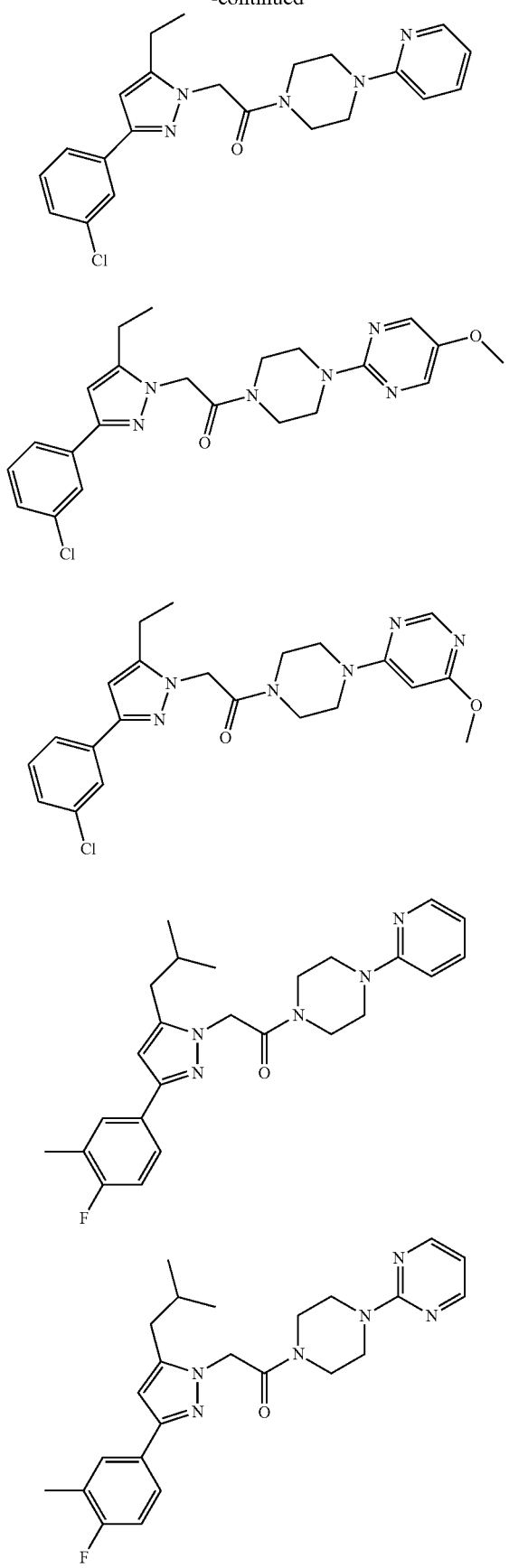
232
-continued
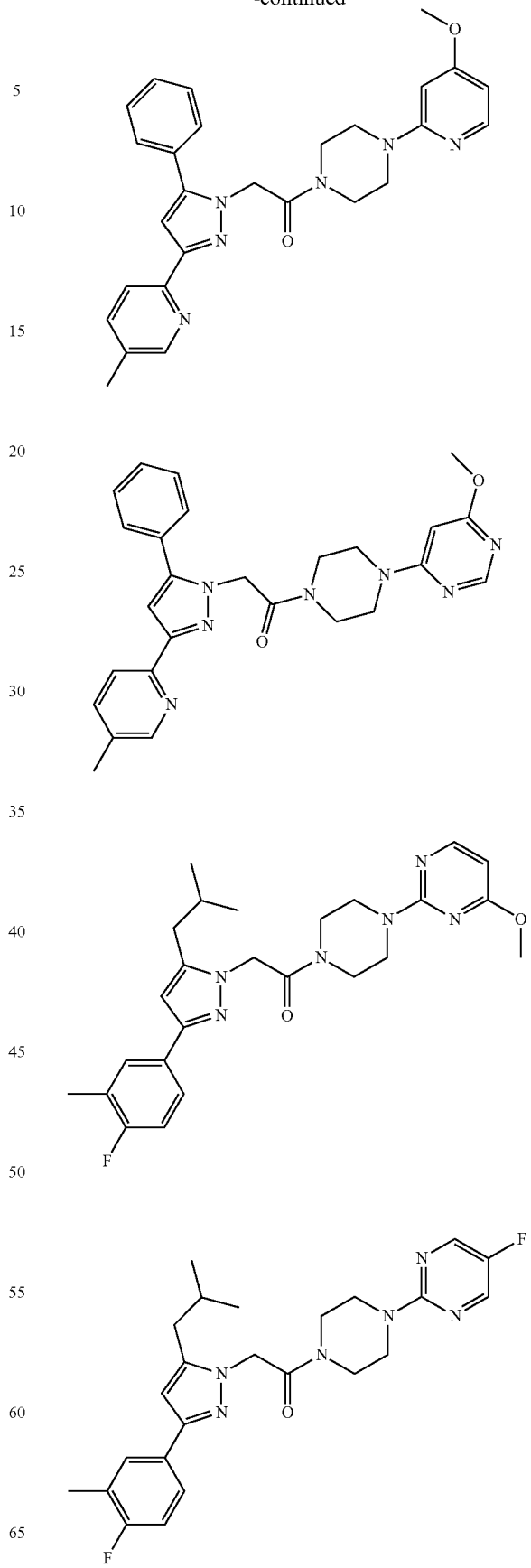

233
-continued
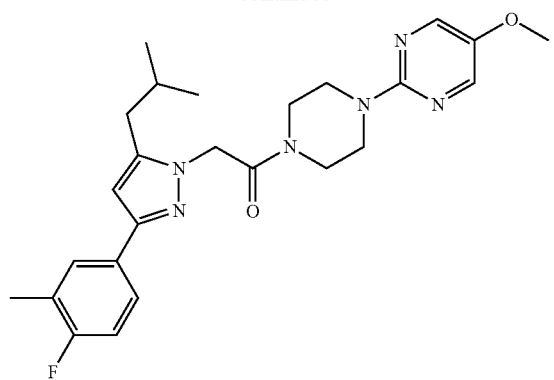
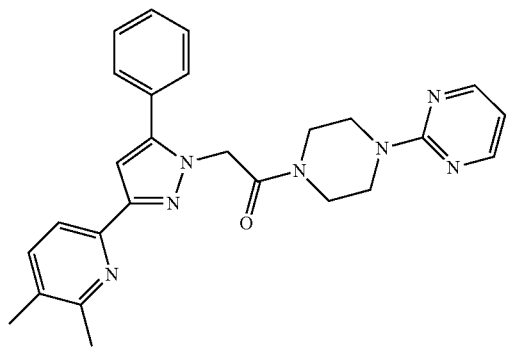
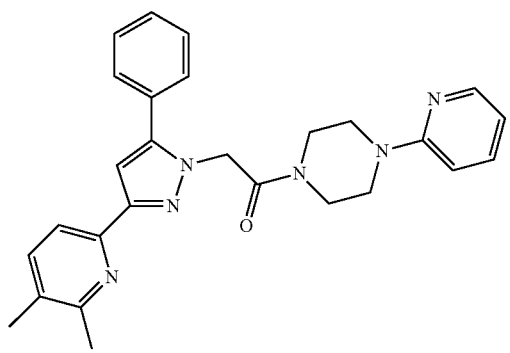
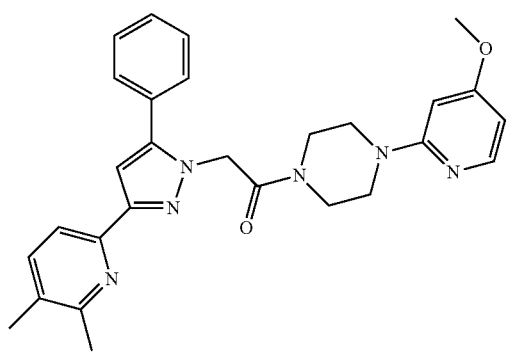
234
-continued
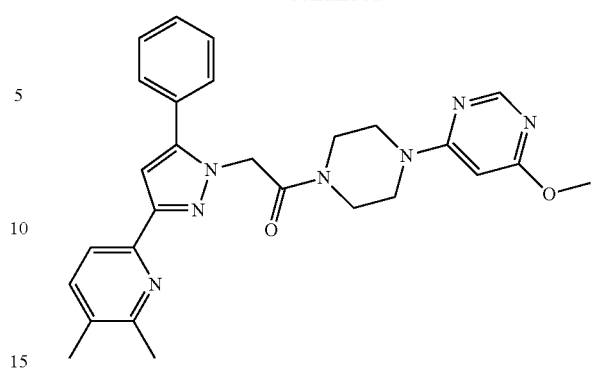
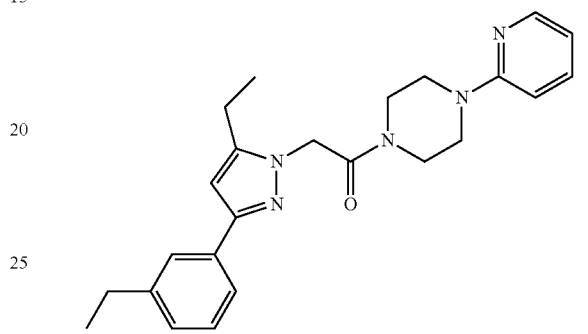
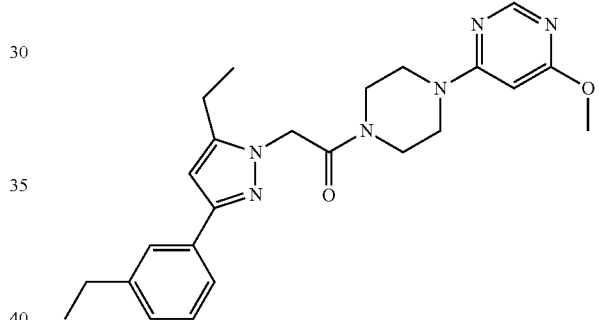
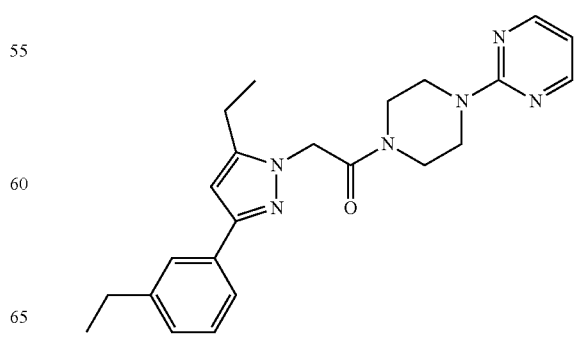

235

237
-continued
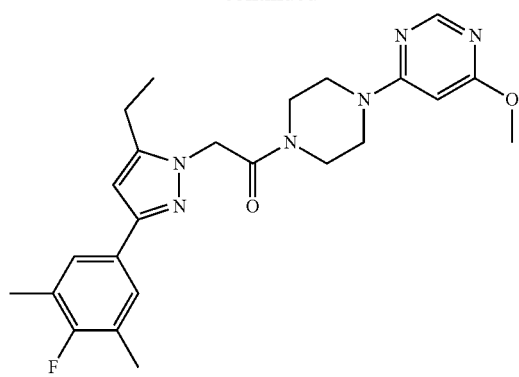
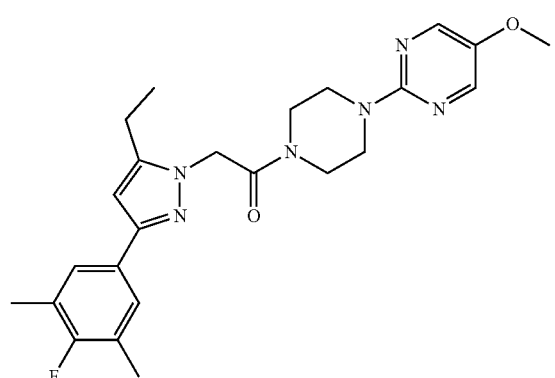
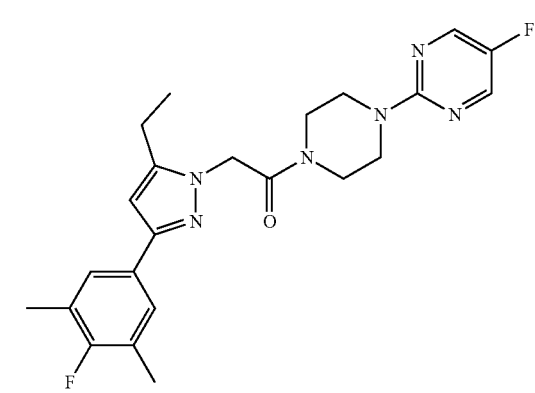
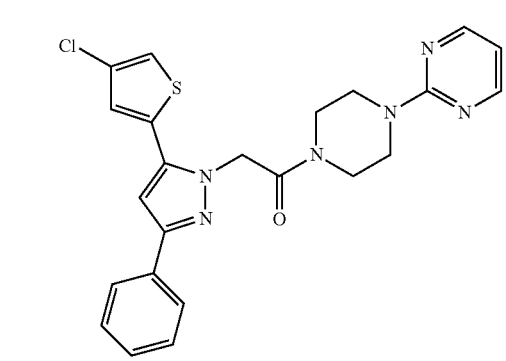
238
-continued
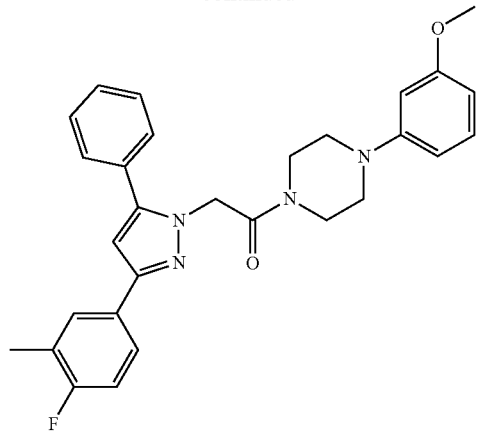
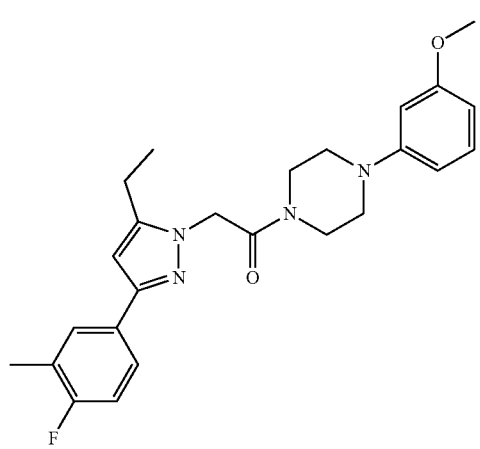
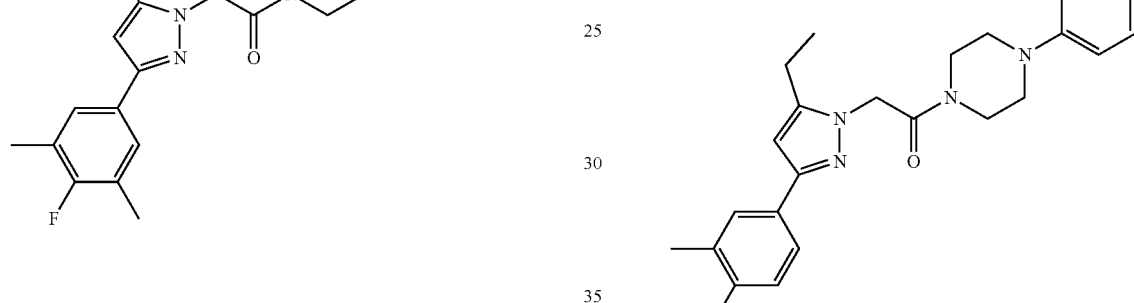
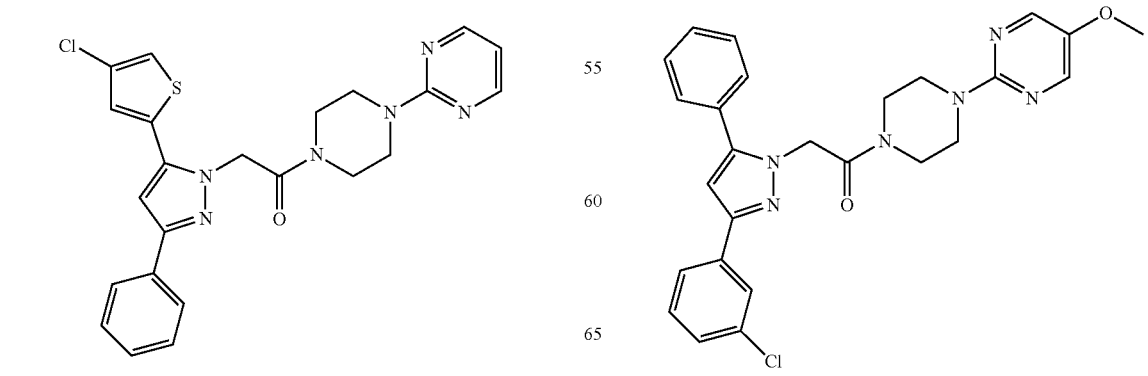

239
-continued
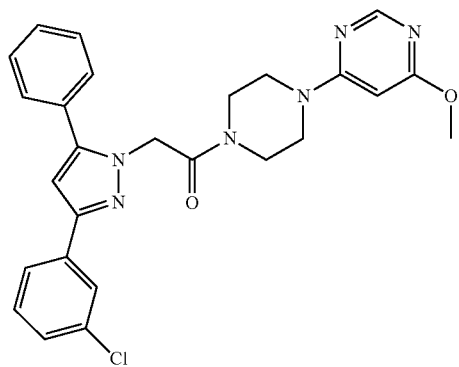
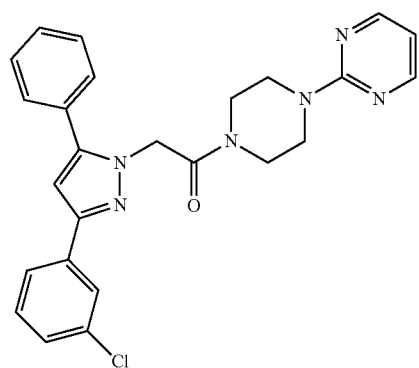
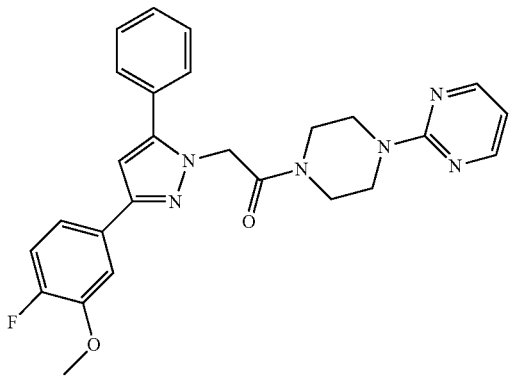
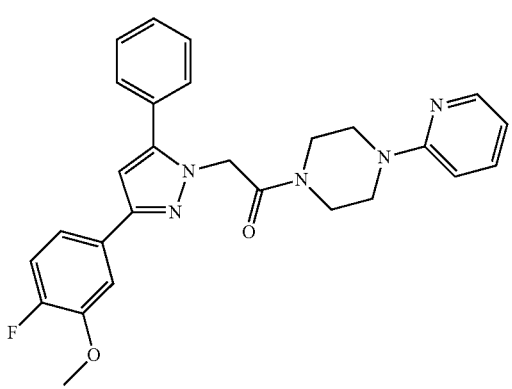
240
-continued
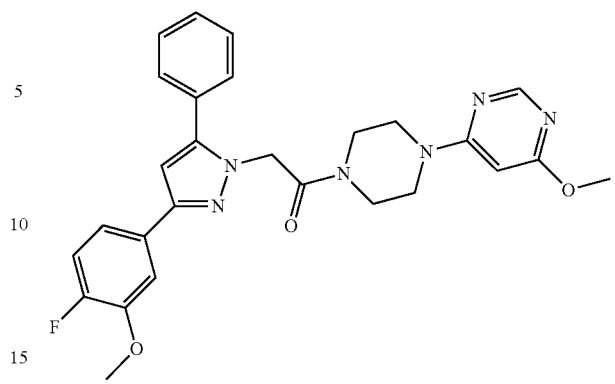
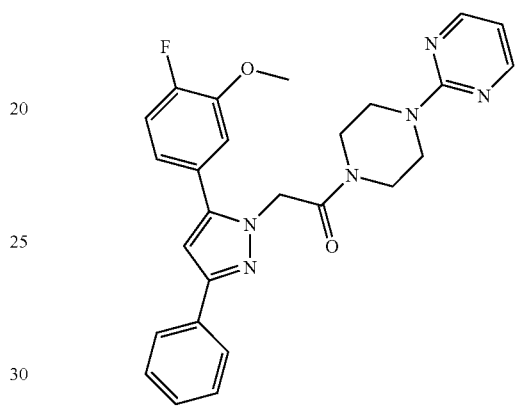
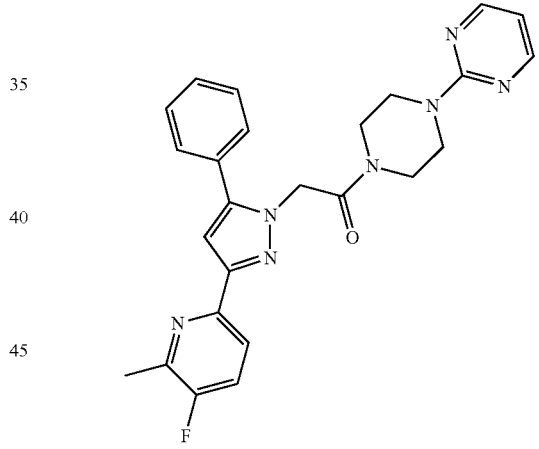
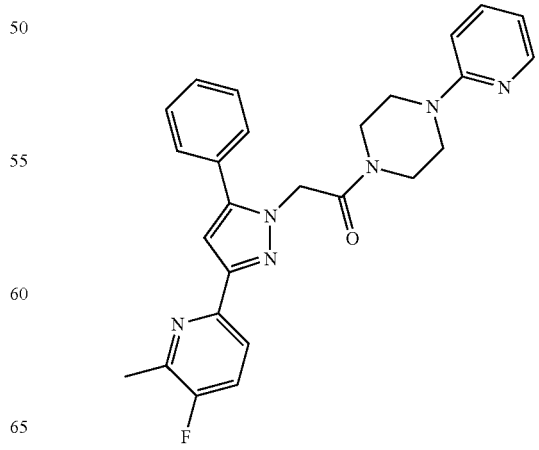

| 241 | 242 |
|---|---|
| -continued | -continued |
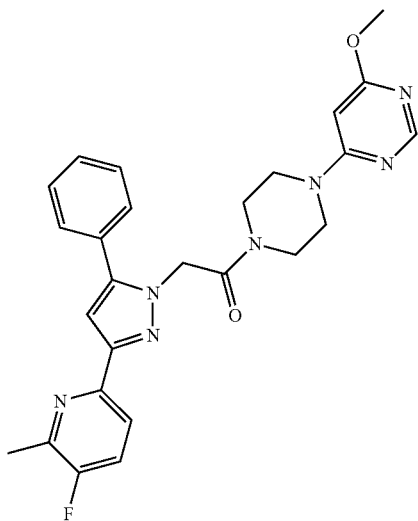
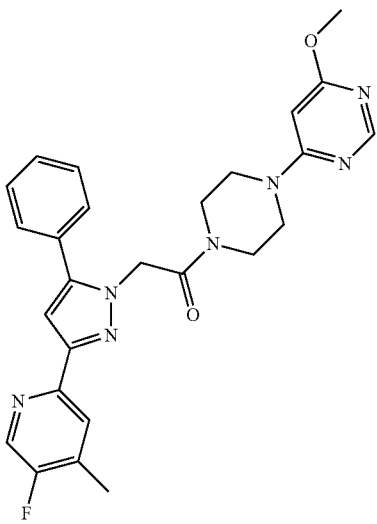
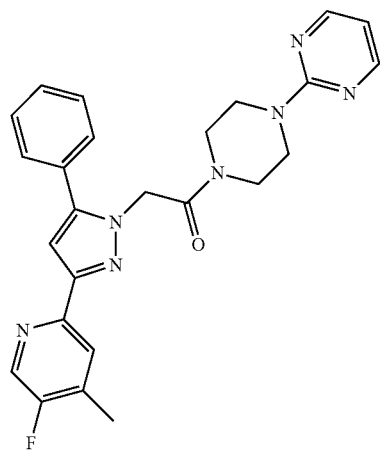
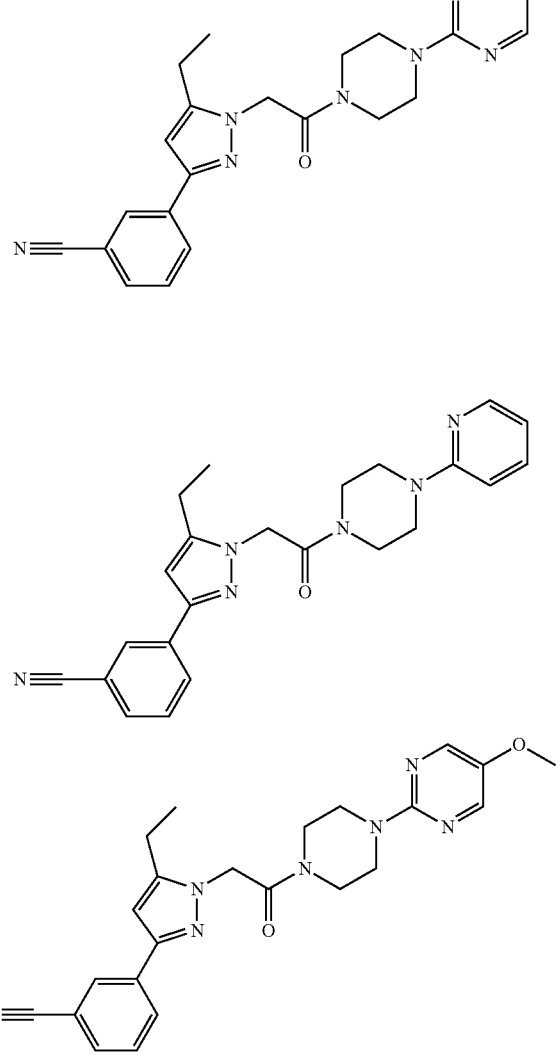
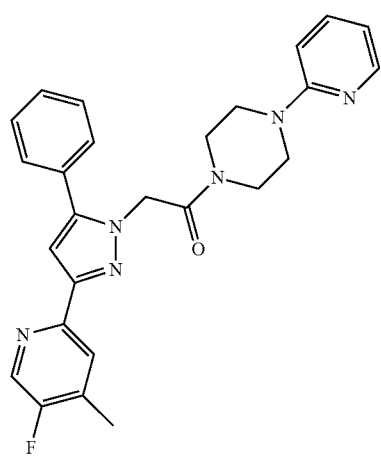

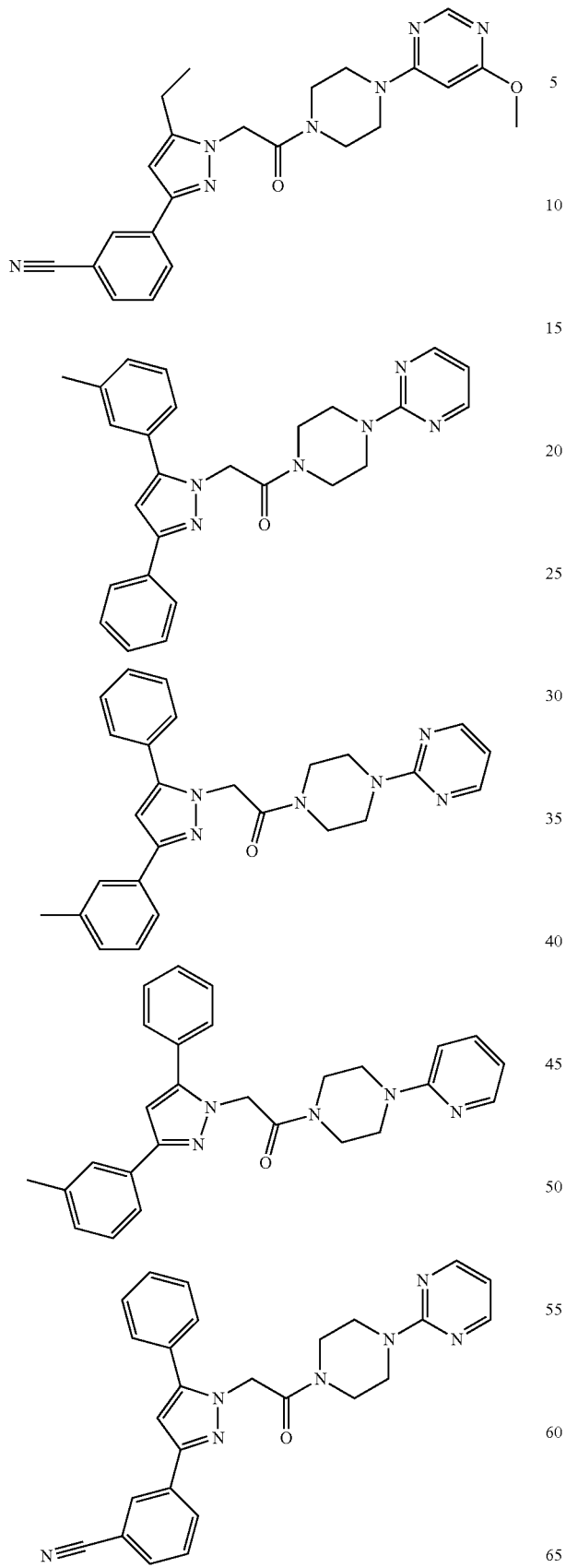
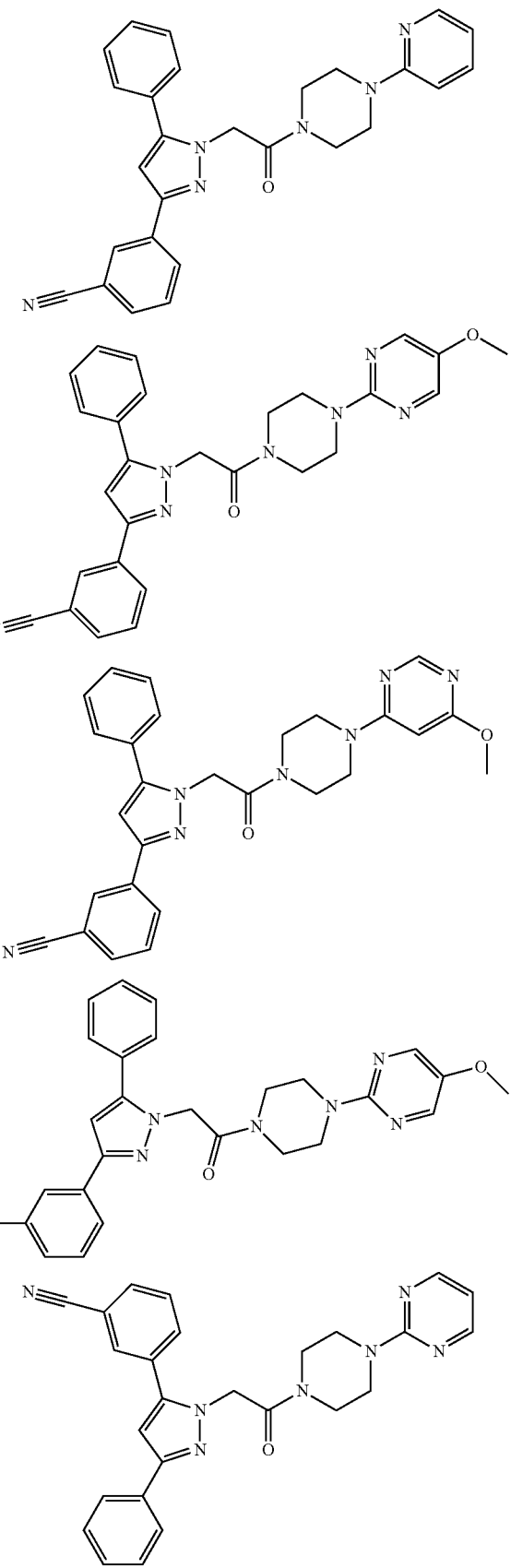

245
-continued
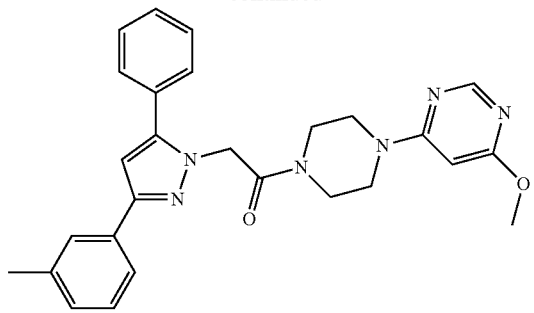
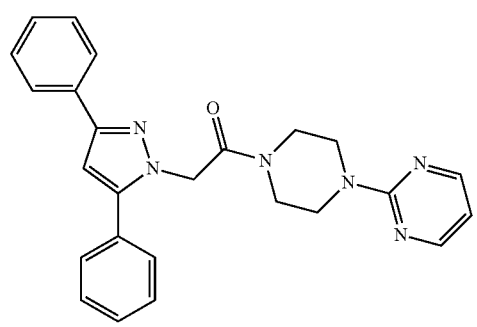
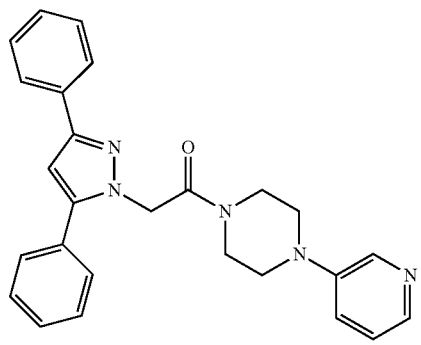
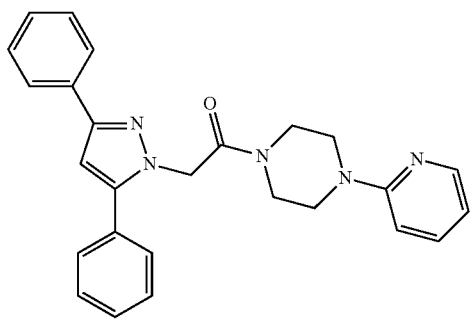
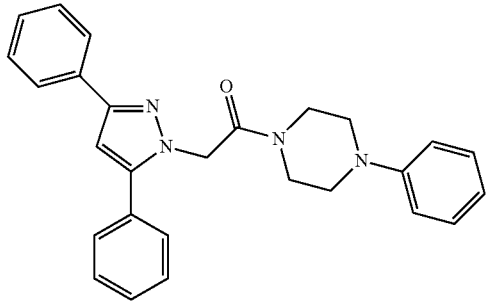
246
-continued
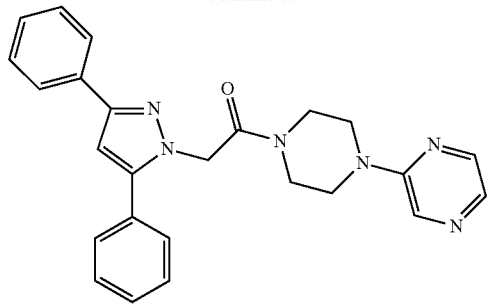
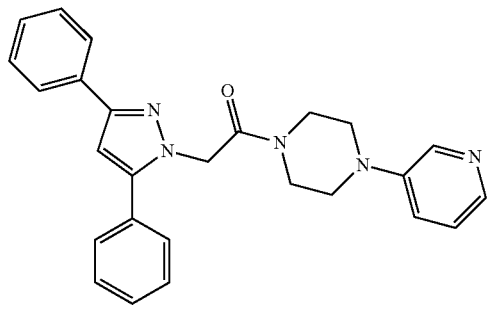
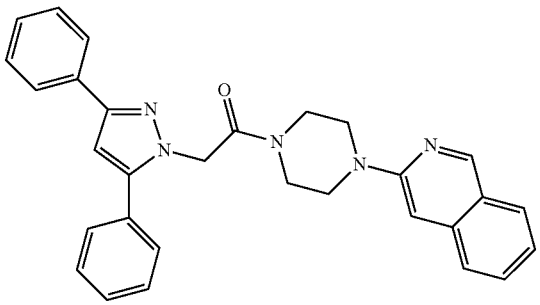
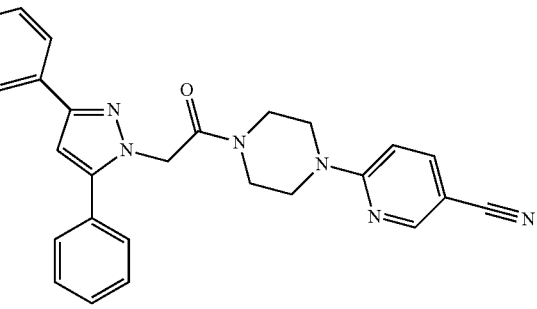
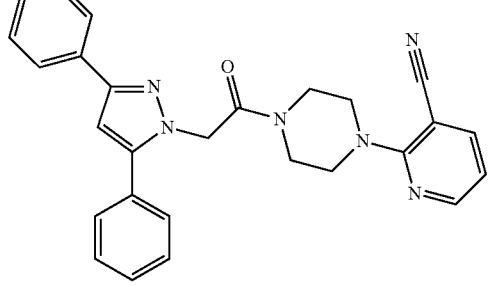

247
-continued
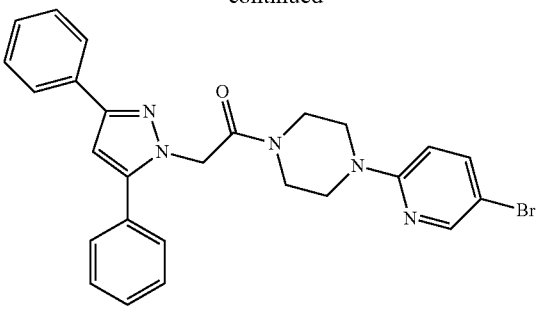
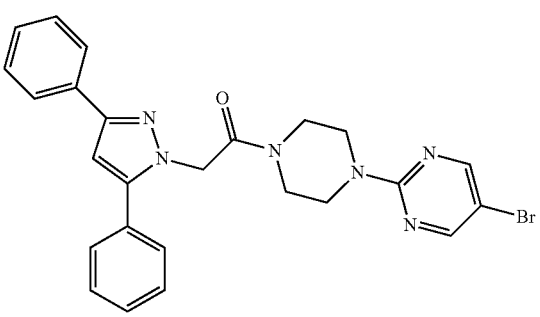
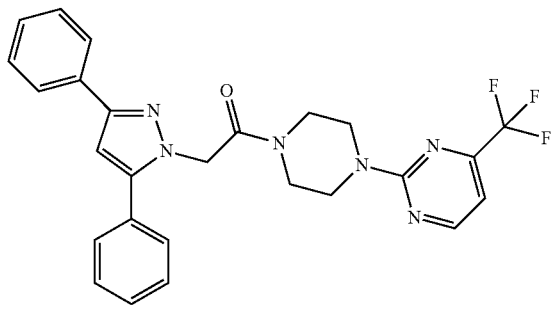
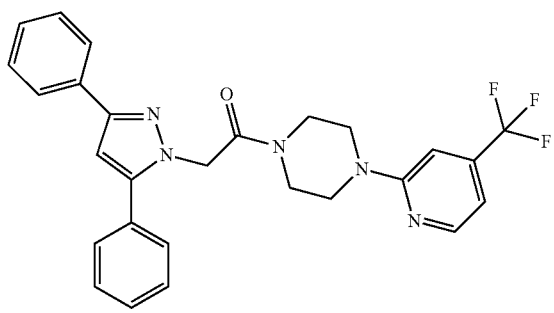
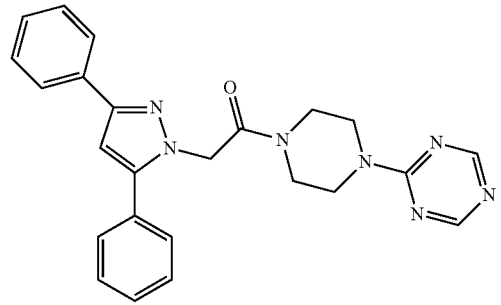
248
-continued
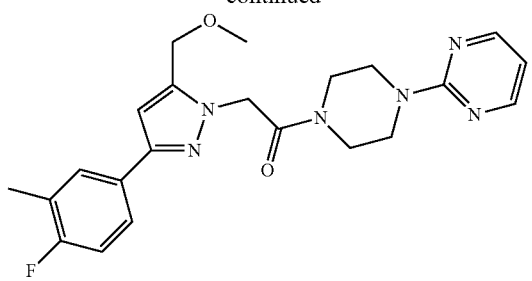
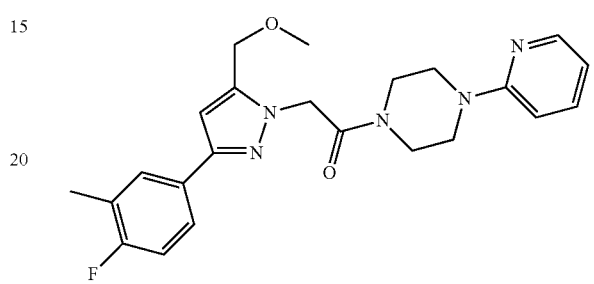
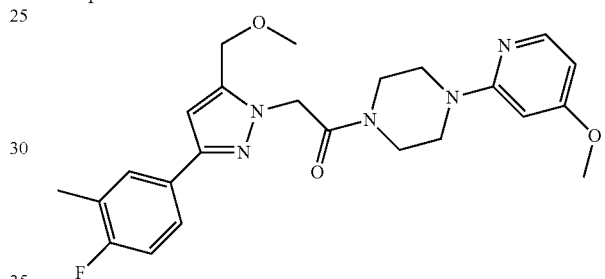
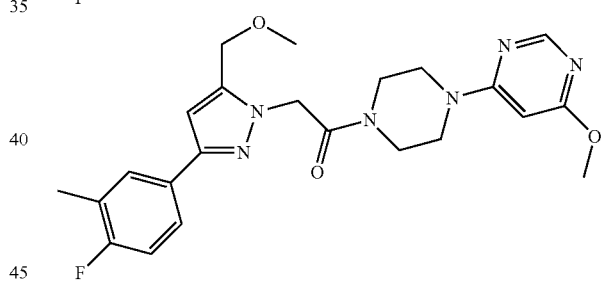
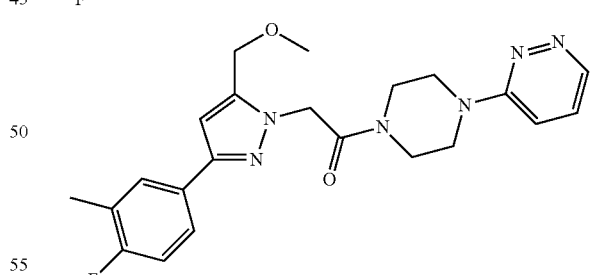
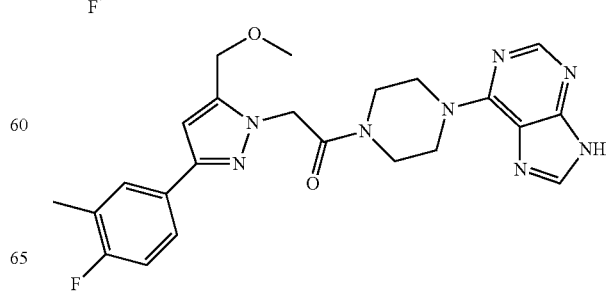

249
-continued
250
-continued
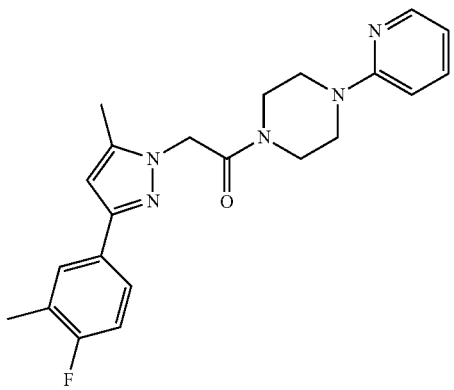
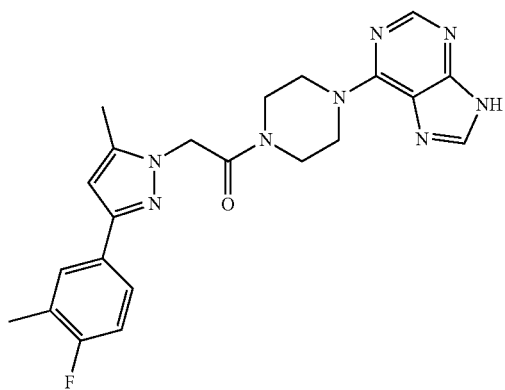
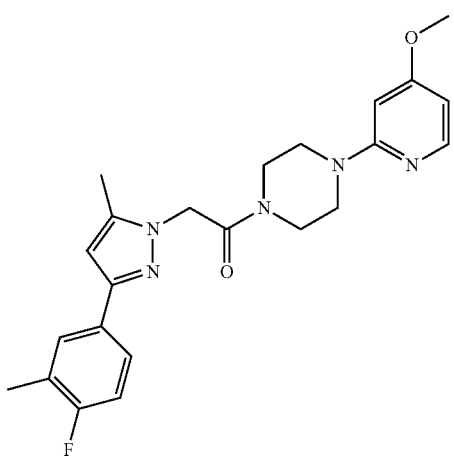
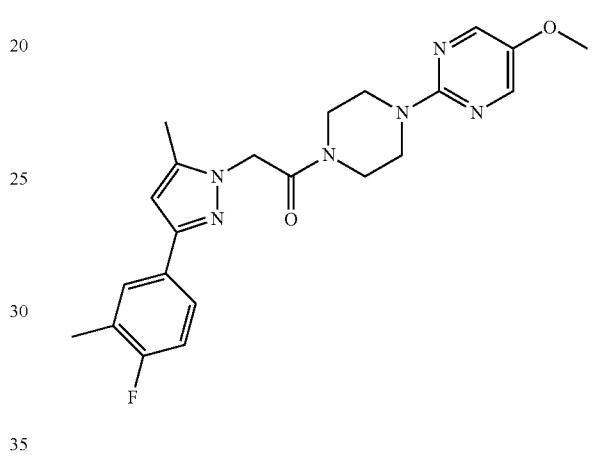
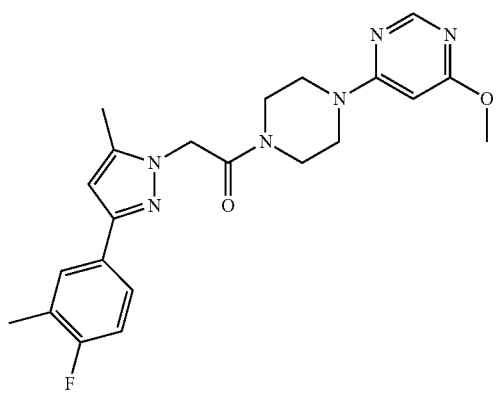
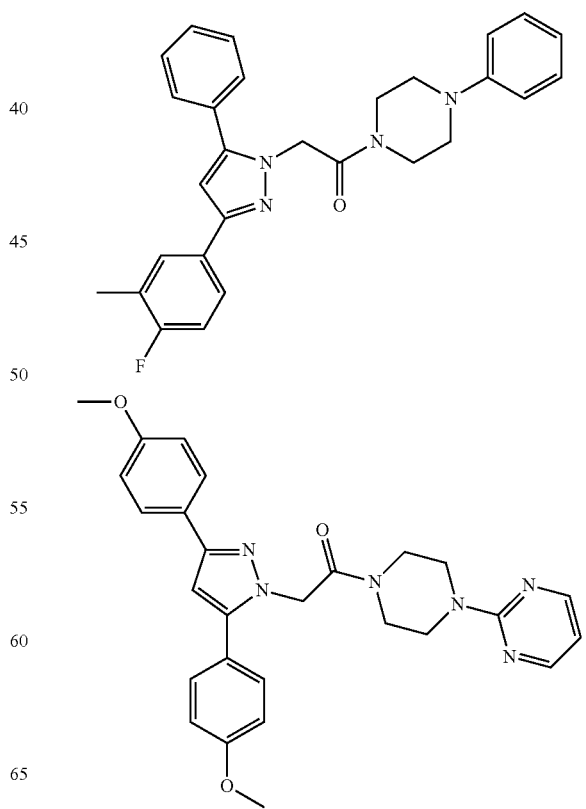
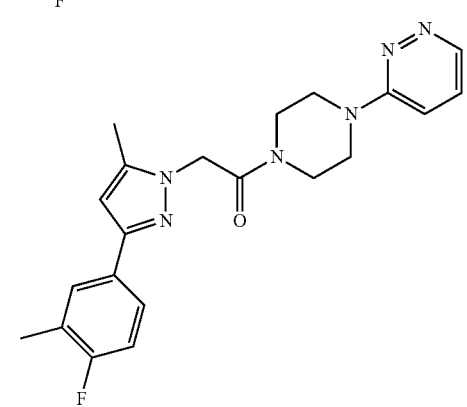

251
-continued
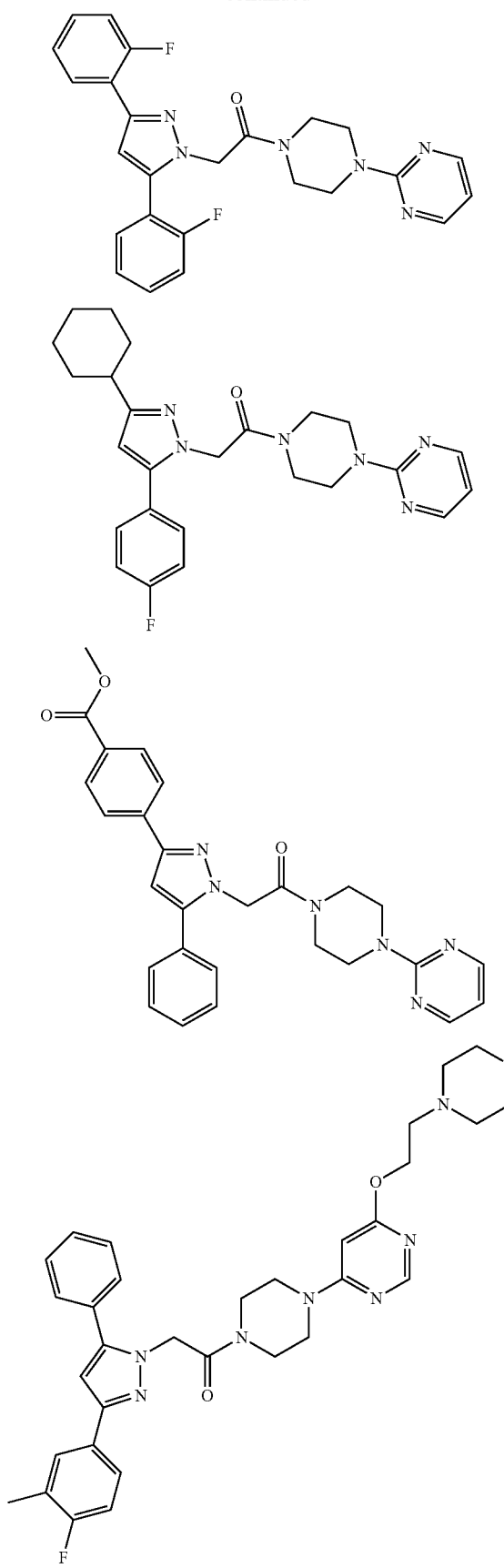
252
-continued
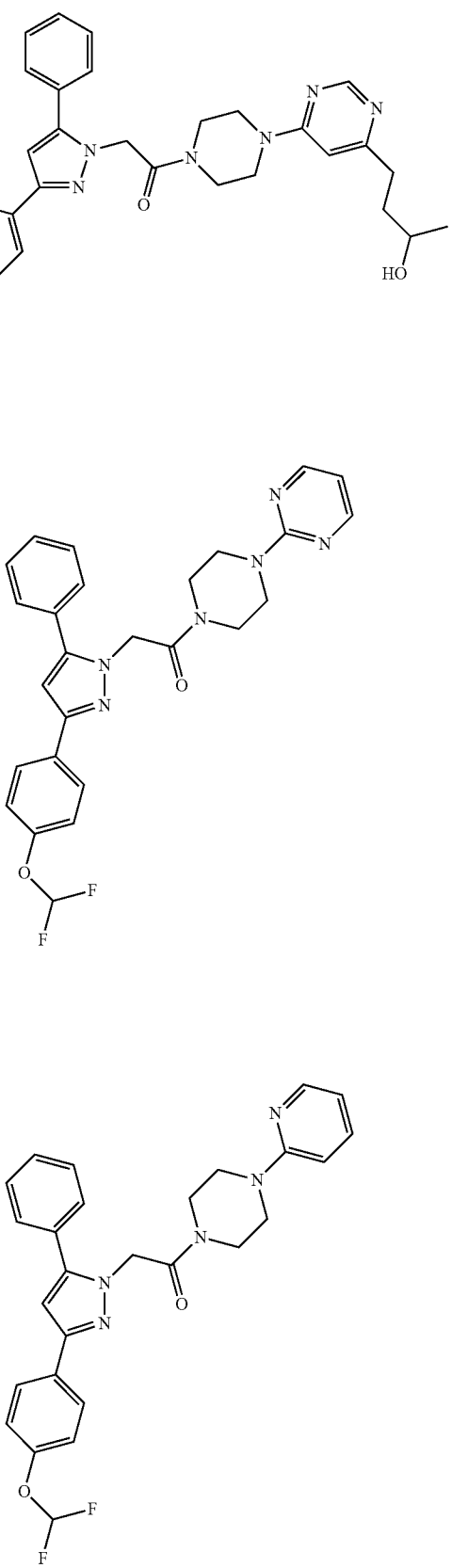

253
-continued
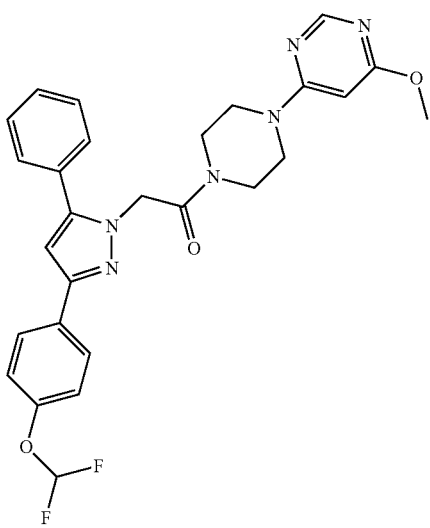
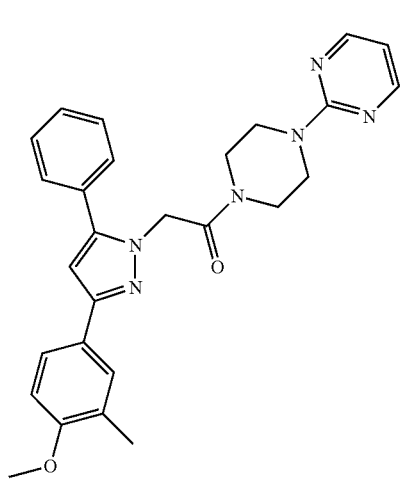
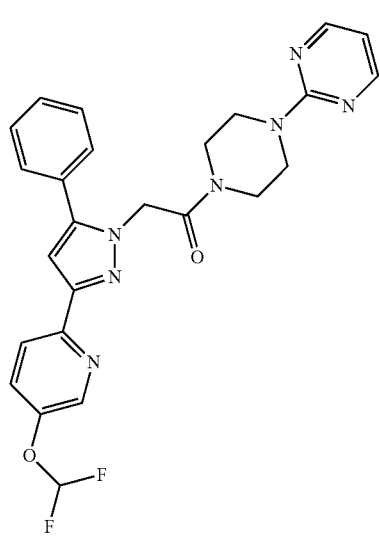
254
-continued
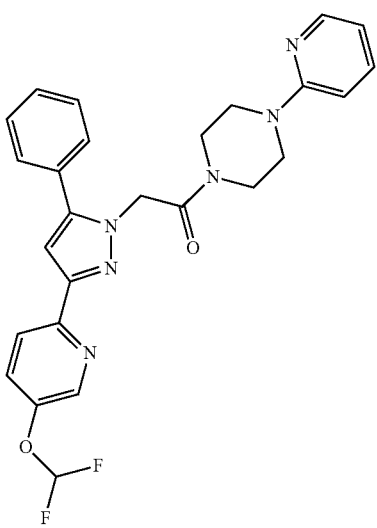
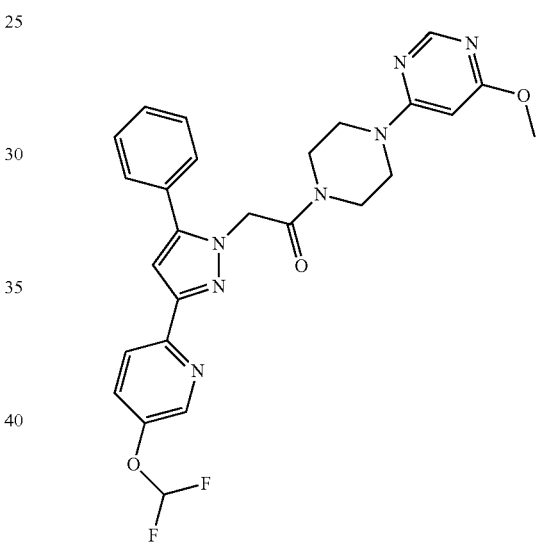
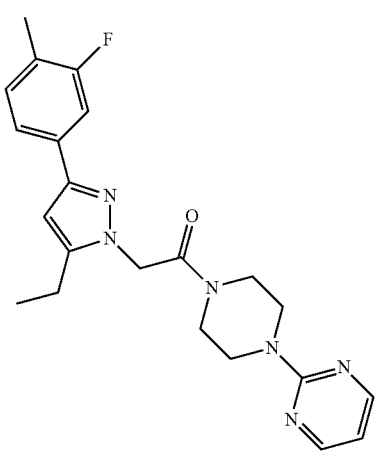

255
-continued
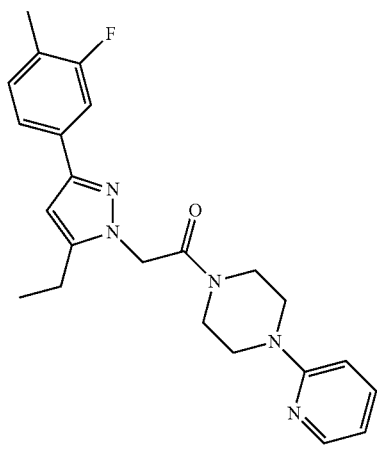
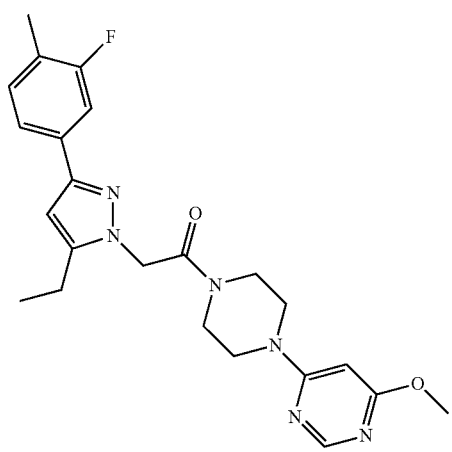
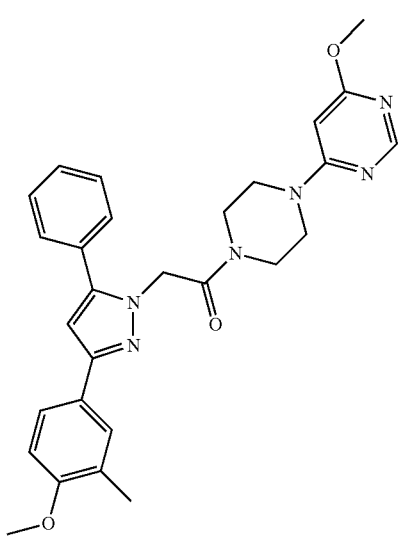
256
-continued
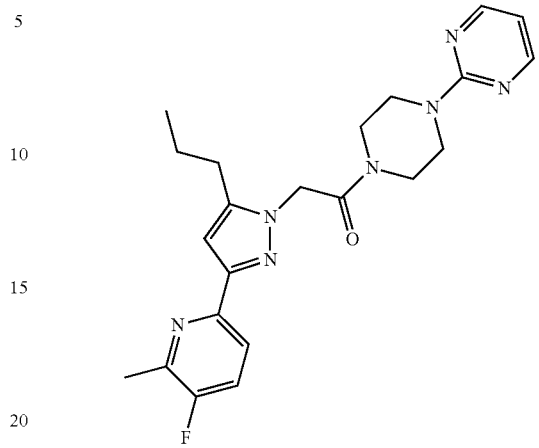
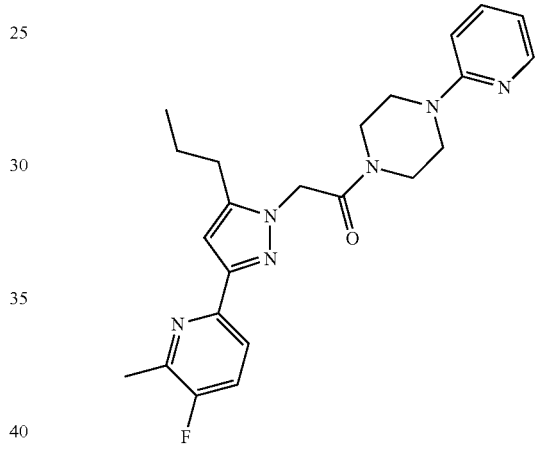
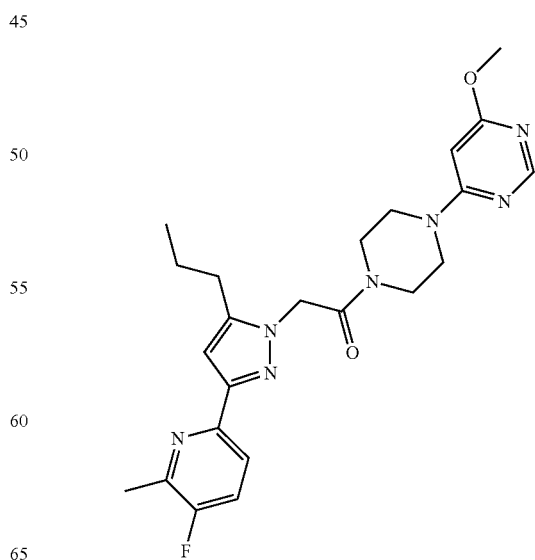

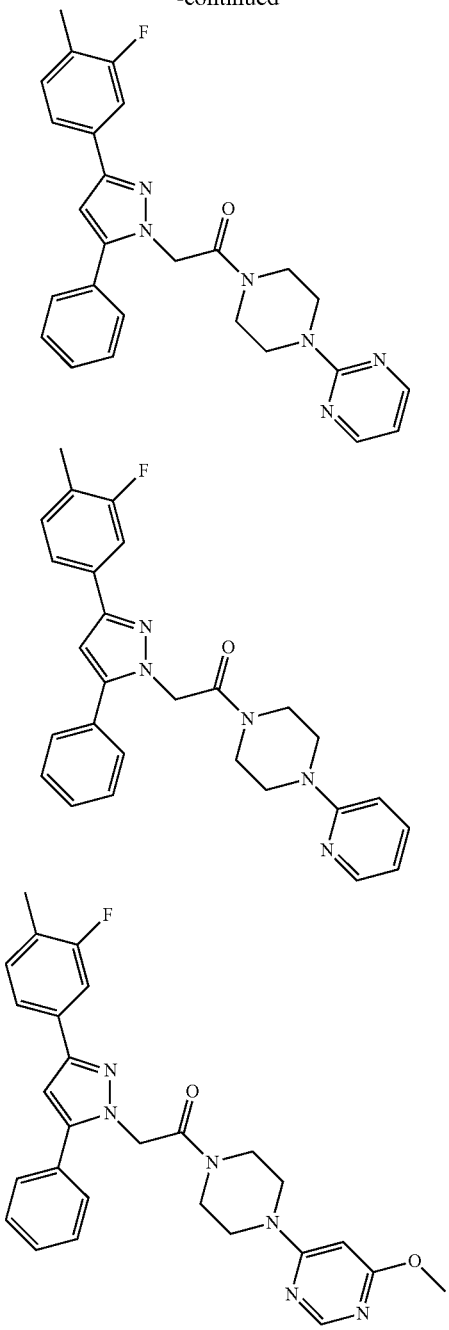
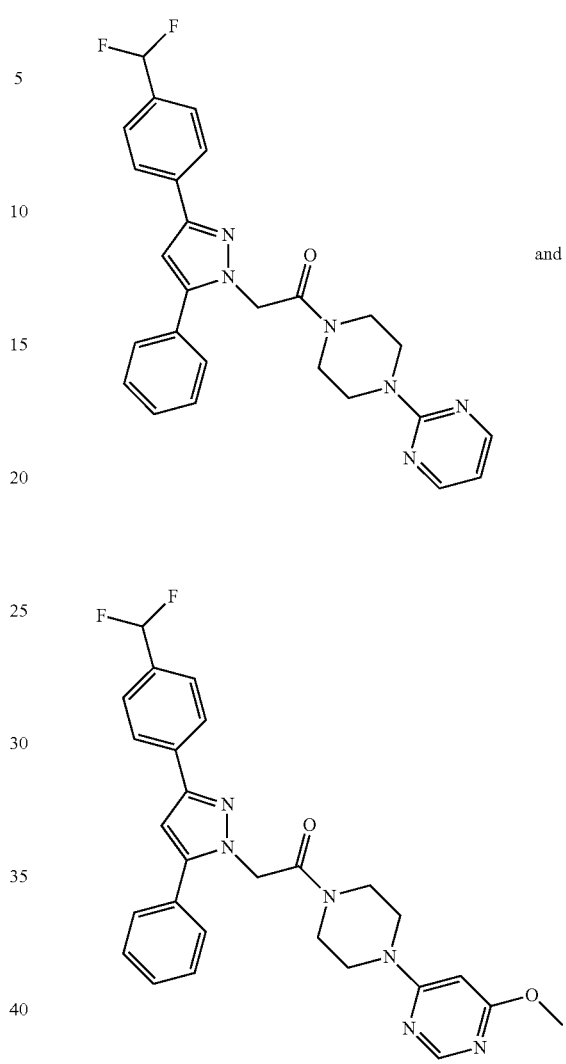
or a physiologically acceptable salt thereof.
2. A pharmaceutical composition comprising a therapeutically effective amount of a compound according to claim 1 or a pharmaceutically acceptable salt thereof in admixture with a pharmaceutically acceptable adjuvant, diluent and/or carrier.
* * * * *